US012589159B2

(12) United States Patent
Addis et al.

(10) Patent No.: US 12,589,159 B2
(45) Date of Patent: *Mar. 31, 2026

(54) CD71 BINDING FIBRONECTIN TYPE III DOMAINS

(71) Applicant: Aro Biotherapeutics Company, Philadelphia, PA (US)

(72) Inventors: Russell C. Addis, Philadelphia, PA (US); Zhanna Druzina, Philadelphia, PA (US); Robert Kolakowski, Philadelphia, PA (US); Swapnil Kulkarni, Philadelphia, PA (US); Steven G. Nadler, Philadelphia, PA (US); Karyn O'Neil, Philadelphia, PA (US); Yao Xin, Philadelphia, PA (US)

(73) Assignee: ARO Biotherapeutics Company, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/174,751

(22) Filed: Feb. 27, 2023

(65) Prior Publication Data

US 2024/0277858 A1      Aug. 22, 2024

Related U.S. Application Data

(62) Division of application No. 17/070,020, filed on Oct. 14, 2020, now Pat. No. 11,628,222.

(60) Provisional application No. 62/949,020, filed on Dec. 17, 2019, provisional application No. 62/914,643, filed on Oct. 14, 2019.

(51) Int. Cl.
| | |
|---|---|
| *A61K 47/64* | (2017.01) |
| *A61K 31/7088* | (2006.01) |
| *C07K 14/435* | (2006.01) |
| *C12N 15/113* | (2010.01) |

(52) U.S. Cl.
CPC ...... *A61K 47/6435* (2017.08); *A61K 31/7088* (2013.01); *C07K 14/435* (2013.01); *C12N 15/113* (2013.01); *C12N 2310/11* (2013.01); *C12N 2310/14* (2013.01); *C12N 2310/3513* (2013.01); *C12N 2320/32* (2013.01)

(58) Field of Classification Search
CPC ............ C12N 2320/32; C12N 2310/14; C12N 2310/3513; C12N 2310/11; C12N 15/113; A61K 47/6435; A61K 31/7088; C07K 14/435
See application file for complete search history.

(56) References Cited

U.S. PATENT DOCUMENTS

| | | | |
|---|---|---|---|
| 4,281,061 A | 7/1981 | Zuk et al. | |
| 5,223,409 A | 6/1993 | Ladner et al. | |
| 5,643,763 A | 7/1997 | Dunn et al. | |
| 5,643,768 A | 7/1997 | Kawasaki | |
| 5,658,727 A | 8/1997 | Barbas et al. | |
| 5,691,157 A | 11/1997 | Gong et al. | |
| 5,846,456 A | 12/1998 | Liu | |
| 5,856,456 A | 1/1999 | Whitlow et al. | |
| 6,018,030 A | 1/2000 | Ferrari et al. | |
| 6,162,903 A | 12/2000 | Trowern et al. | |
| 6,172,197 B1 | 1/2001 | McCafferty et al. | |
| 6,355,776 B1 | 3/2002 | Ferrari et al. | |
| 6,462,189 B1 | 10/2002 | Koide | |
| 6,472,147 B1 | 10/2002 | Janda et al. | |
| 6,521,427 B1 | 2/2003 | Evans | |
| 6,582,915 B1 | 6/2003 | Griffiths et al. | |
| 6,670,127 B2 | 12/2003 | Evans | |
| 6,673,901 B2 | 1/2004 | Koide | |
| 6,703,199 B1 | 3/2004 | Koide | |
| 6,818,418 B1 | 11/2004 | Lipovsek et al. | |
| 6,846,655 B1 | 1/2005 | Wagner et al. | |
| 6,969,108 B2 | 11/2005 | Fukumoto et al. | |
| 7,078,490 B2 | 7/2006 | Koide | |
| 7,115,396 B2 | 10/2006 | Lipovsek et al. | |
| 7,119,171 B2 | 10/2006 | Koide | |
| 7,153,661 B2 | 12/2006 | Koide | |
| 7,288,638 B2 | 10/2007 | Jure-Kunkel et al. | |
| 7,427,672 B2 | 9/2008 | Imanishi et al. | |
| 7,709,214 B2 | 5/2010 | Freeman et al. | |
| 7,794,710 B2 | 9/2010 | Chen et al. | |
| 7,842,476 B2 | 11/2010 | McGregor et al. | |
| 7,943,743 B2 | 5/2011 | Korman et al. | |
| 8,217,149 B2 | 7/2012 | Irving et al. | |
| 8,278,419 B2 | 10/2012 | Jacobs et al. | |
| 8,293,482 B2 | 10/2012 | Jacobs et al. | |
| 8,552,154 B2 | 10/2013 | Freeman et al. | |

(Continued)

FOREIGN PATENT DOCUMENTS

| | | |
|---|---|---|
| CN | 102076713 A | 5/2011 |
| CN | 103827361 A | 5/2014 |

(Continued)

OTHER PUBLICATIONS

Drumm et al, Genetic Variation and Clinical Heterogeneity in Cystic Fibrosis, Annu. Rev. Pathol. Mech. Dis., 2012, 7, pp. 267-282.*
Yampolsky et al, The Exchangeability of Amino Acids in Proteins, Genetics, 2005, 170, pp. 1459-1472.*
Kontermann, Strategies for extended serum half-life of protein therapeutics, Current Opinion in Biotechnology, 2011, 22, pp. 868-876.*
Tenente et al, Myogenic regulatory transcription factors regulate growth in rhabdomyosarcoma, eLife, 2017, 6:e19214, pp. 1-24.*
Sugiura et al, Increased CD40 Expression on Muscle Cells of Polymyositis and Dermatomyositis: Role of CD40-CD40 Ligand Interaction in IL-6, IL-8, IL-15, and Monocyte Chemoattractant Protein-1 Production, The Journal of Immunology, 2000, 164, pp. 6593-6600.*

(Continued)

*Primary Examiner* — Li N Komatsu
(74) *Attorney, Agent, or Firm* — Goodwin Procter LLP

(57) ABSTRACT

The present disclosure relates to polypeptides, such as fibronectin type III (FN3) domains that can bind CD71, their conjugates, isolated nucleotides encoding the molecules, vectors, host-cells, as well as methods of making and using the same.

18 Claims, No Drawings

Specification includes a Sequence Listing.

(56)                  References Cited

U.S. PATENT DOCUMENTS

| | | |
|---|---|---|
| 8,569,227 B2 | 10/2013 | Jacobs |
| 8,741,295 B2 | 6/2014 | Olive |
| 8,779,108 B2 | 7/2014 | Queva et al. |
| 8,981,063 B2 | 3/2015 | Chen |
| 9,156,887 B2 | 10/2015 | Jacobs |
| 9,175,082 B2 | 11/2015 | Zhou et al. |
| 9,200,273 B2 | 12/2015 | Diem et al. |
| 9,212,224 B2 | 12/2015 | Cogswell et al. |
| 9,326,941 B2 | 5/2016 | Chae et al. |
| 9,546,368 B2 | 1/2017 | Bennett et al. |
| 9,644,023 B2 | 5/2017 | Torres et al. |
| 9,695,228 B2 | 7/2017 | Mark et al. |
| 9,897,612 B2 | 2/2018 | Diem et al. |
| 10,196,446 B2 | 2/2019 | Goldberg et al. |
| 10,233,448 B2 | 3/2019 | Maier et al. |
| 10,597,438 B2 | 3/2020 | Diem et al. |
| 10,611,823 B2 | 4/2020 | Diem et al. |
| 10,626,165 B2 | 4/2020 | Hawkins et al. |
| 10,781,246 B2 | 9/2020 | Brezki et al. |
| 10,925,932 B2 | 2/2021 | Diem et al. |
| 11,628,222 B2 | 4/2023 | Addis et al. |
| 11,781,138 B2 | 10/2023 | Addis et al. |
| 12,037,379 B2 * | 7/2024 | Addis ................ A61K 31/7125 |
| 12,239,710 B2 | 3/2025 | Kulkarni et al. |
| 2004/0197332 A1 | 10/2004 | Ullrich et al. |
| 2004/0259781 A1 | 12/2004 | Chiquet-Ehrismann et al. |
| 2005/0004029 A1 | 1/2005 | Garcia |
| 2005/0038229 A1 | 2/2005 | Lipovsek et al. |
| 2005/0255548 A1 | 11/2005 | Lipovsek et al. |
| 2005/0272083 A1 | 12/2005 | Seshagiri |
| 2006/0040278 A1 | 2/2006 | Cojocaru et al. |
| 2006/0246059 A1 | 11/2006 | Lipovsek et al. |
| 2006/0270604 A1 | 11/2006 | Lipovsek et al. |
| 2007/0148126 A1 | 6/2007 | Chen et al. |
| 2007/0160533 A1 | 7/2007 | Chen et al. |
| 2007/0184476 A1 | 8/2007 | Hsieh et al. |
| 2008/0015339 A1 | 1/2008 | Lipovsek et al. |
| 2008/0220049 A1 | 9/2008 | Chen et al. |
| 2008/0241159 A1 | 10/2008 | Gerritsen et al. |
| 2008/0287386 A1 | 11/2008 | Mor et al. |
| 2009/0042906 A1 | 2/2009 | Huang et al. |
| 2009/0176654 A1 | 7/2009 | Cappuccilli et al. |
| 2009/0274693 A1 | 11/2009 | Gilmer et al. |
| 2009/0299040 A1 | 12/2009 | Camphausen et al. |
| 2009/0311803 A1 | 12/2009 | Way et al. |
| 2010/0093662 A1 | 4/2010 | Defaye et al. |
| 2010/0136129 A1 | 6/2010 | Agueros Bazo et al. |
| 2010/0144601 A1 | 6/2010 | Jacobs et al. |
| 2010/0179094 A1 | 7/2010 | Emanuel et al. |
| 2010/0203142 A1 | 8/2010 | Zhang et al. |
| 2010/0216708 A1 | 8/2010 | Jacobs et al. |
| 2010/0221248 A1 | 9/2010 | Wittrup et al. |
| 2010/0254989 A1 | 10/2010 | Bossenmaier et al. |
| 2010/0255056 A1 | 10/2010 | Jacobs et al. |
| 2011/0021746 A1 | 1/2011 | Cappuccilli et al. |
| 2011/0038866 A1 | 2/2011 | Hastewell et al. |
| 2011/0053842 A1 | 3/2011 | Camphausen et al. |
| 2011/0081345 A1 | 4/2011 | Moore et al. |
| 2011/0118144 A1 | 5/2011 | Hyun et al. |
| 2011/0124527 A1 | 5/2011 | Cappuccilli et al. |
| 2011/0274623 A1 | 11/2011 | Jacobs |
| 2011/0287009 A1 | 11/2011 | Scheer et al. |
| 2012/0225870 A1 | 9/2012 | Janne et al. |
| 2012/0244164 A1 | 9/2012 | Beste et al. |
| 2012/0263723 A1 | 10/2012 | Davies et al. |
| 2012/0270797 A1 | 10/2012 | Wittrup et al. |
| 2012/0315639 A1 | 12/2012 | Deng et al. |
| 2012/0321666 A1 | 12/2012 | Cooper et al. |
| 2013/0012435 A1 | 1/2013 | Camphausen et al. |
| 2013/0039927 A1 | 2/2013 | Dewhurst et al. |
| 2013/0079243 A1 | 3/2013 | Diem et al. |
| 2013/0123342 A1 | 5/2013 | Brown |
| 2013/0130377 A1 | 5/2013 | Lee et al. |
| 2013/0184212 A1 | 7/2013 | Camphausen et al. |
| 2013/0226834 A1 | 8/2013 | Gannalo |

| | | |
|---|---|---|
| 2013/0273561 A1 | 10/2013 | Walker et al. |
| 2014/0141000 A1 | 5/2014 | Chiu et al. |
| 2014/0155325 A1 | 6/2014 | Mark et al. |
| 2014/0155326 A1 | 6/2014 | Mark et al. |
| 2014/0255408 A1 | 9/2014 | Chiu et al. |
| 2014/0271467 A1 | 9/2014 | Hackel et al. |
| 2014/0341917 A1 | 11/2014 | Nastri et al. |
| 2014/0349929 A1 | 11/2014 | Camphausen et al. |
| 2014/0371296 A1 | 12/2014 | Bennett et al. |
| 2015/0005364 A1 | 1/2015 | Chae et al. |
| 2015/0104808 A1 | 4/2015 | Goldberg et al. |
| 2015/0118288 A1 | 4/2015 | Lee |
| 2015/0191543 A1 | 7/2015 | Wu et al. |
| 2015/0197571 A1 | 7/2015 | Freeman et al. |
| 2015/0203580 A1 | 7/2015 | Papadopoulos et al. |
| 2015/0210756 A1 | 7/2015 | Torres et al. |
| 2015/0252097 A1 | 9/2015 | Camphausen et al. |
| 2015/0274835 A1 | 10/2015 | Marasco et al. |
| 2015/0346208 A1 | 12/2015 | Couto et al. |
| 2015/0355184 A1 | 12/2015 | Pierce et al. |
| 2016/0041182 A1 | 2/2016 | Diem et al. |
| 2016/0303256 A1 | 10/2016 | Liu |
| 2016/0326232 A1 | 11/2016 | Rosa et al. |
| 2016/0347840 A1 | 12/2016 | Anderson et al. |
| 2016/0355599 A1 | 12/2016 | Sagert et al. |
| 2017/0174748 A1 | 6/2017 | Mitchell et al. |
| 2017/0258948 A1 | 9/2017 | Morin et al. |
| 2017/0281795 A1 | 10/2017 | Geall et al. |
| 2017/0348397 A1 | 12/2017 | Diem et al. |
| 2017/0362301 A1 | 12/2017 | Anderson et al. |
| 2018/0127485 A1 | 5/2018 | Hastewell et al. |
| 2018/0162929 A1 | 6/2018 | Diem et al. |
| 2019/0070322 A1 | 3/2019 | Bander |
| 2019/0127444 A1 | 5/2019 | Brezski et al. |
| 2019/0175651 A1 | 6/2019 | Lee et al. |
| 2019/0184018 A1 | 6/2019 | Manoharan et al. |
| 2019/0184028 A1 | 6/2019 | Dudkin et al. |
| 2019/0202927 A1 | 7/2019 | Sagert et al. |
| 2019/0256575 A1 | 8/2019 | Chen et al. |
| 2019/0263915 A1 | 8/2019 | Goldberg et al. |
| 2019/0330361 A1 | 10/2019 | Chin et al. |
| 2021/0108201 A1 | 4/2021 | Addis et al. |
| 2021/0145976 A1 | 5/2021 | Addis et al. |
| 2022/0332795 A1 | 10/2022 | Addis et al. |
| 2022/0370626 A1 | 11/2022 | Kulkarni et al. |
| 2023/0330246 A1 | 10/2023 | Marelius et al. |
| 2024/0043844 A1 | 2/2024 | Kulkarni et al. |

FOREIGN PATENT DOCUMENTS

| | | |
|---|---|---|
| CN | 105907719 A | 8/2016 |
| EP | 0985039 A2 | 3/2000 |
| EP | 1137941 A1 | 10/2001 |
| EP | 1210428 A1 | 6/2002 |
| EP | 1266025 A1 | 12/2002 |
| EP | 2935329 A1 | 10/2015 |
| EP | 3473270 A1 | 4/2019 |
| EP | 4146229 A1 | 3/2023 |
| JP | 2011507543 A | 3/2011 |
| JP | 2011517314 A | 6/2011 |
| JP | 2011520961 A | 7/2011 |
| JP | 2011522517 A | 8/2011 |
| JP | 2012507295 A | 3/2012 |
| JP | 2014530014 A | 11/2014 |
| JP | 2016504291 A | 2/2016 |
| KR | 10-2016-0067966 A | 6/2016 |
| WO | 9638557 A1 | 12/1996 |
| WO | 2001014557 A1 | 3/2001 |
| WO | 0164942 A1 | 9/2001 |
| WO | 0232925 A2 | 4/2002 |
| WO | 03104418 A2 | 12/2003 |
| WO | 2004029224 A2 | 4/2004 |
| WO | 2004058821 A2 | 7/2004 |
| WO | 2005018534 A2 | 3/2005 |
| WO | 2005042708 A2 | 5/2005 |
| WO | 2007000671 A2 | 1/2007 |
| WO | 2007047796 A2 | 4/2007 |
| WO | 2007085815 A2 | 8/2007 |
| WO | 2008066752 A2 | 6/2008 |

(56) References Cited

FOREIGN PATENT DOCUMENTS

| WO | 2008079973 A2 | 7/2008 |
| WO | 2008127710 A2 | 10/2008 |
| WO | 2008156642 A1 | 12/2008 |
| WO | 2009023184 A2 | 2/2009 |
| WO | 2009058379 A2 | 5/2009 |
| WO | 2009083804 A2 | 7/2009 |
| WO | 2009085462 A1 | 7/2009 |
| WO | 2009086116 A2 | 7/2009 |
| WO | 2009102421 A2 | 8/2009 |
| WO | 2009111691 A2 | 9/2009 |
| WO | 2009126834 A2 | 10/2009 |
| WO | 2009133208 A1 | 11/2009 |
| WO | 2009142773 A2 | 11/2009 |
| WO | 2010037838 A2 | 4/2010 |
| WO | 2010039248 A1 | 4/2010 |
| WO | 2010051274 A2 | 5/2010 |
| WO | 2010051310 A2 | 5/2010 |
| WO | 2010060095 A1 | 5/2010 |
| WO | 2010093627 A2 | 8/2010 |
| WO | 2010115202 A2 | 10/2010 |
| WO | 2010115551 A1 | 10/2010 |
| WO | 2011005133 A1 | 1/2011 |
| WO | 2011110642 A2 | 9/2011 |
| WO | 2011130324 A1 | 10/2011 |
| WO | 2011131746 A2 | 10/2011 |
| WO | 2011137319 A2 | 11/2011 |
| WO | 2011151412 A1 | 12/2011 |
| WO | 2012016245 A2 | 2/2012 |
| WO | 2012162418 A1 | 11/2012 |
| WO | 2013049275 A1 | 4/2013 |
| WO | 2014081944 A2 | 5/2014 |
| WO | 2014081954 A1 | 5/2014 |
| WO | 2014100079 A1 | 6/2014 |
| WO | 2014165082 A2 | 10/2014 |
| WO | 2014165093 A2 | 10/2014 |
| WO | 2014189973 A2 | 11/2014 |
| WO | 2014209804 A1 | 12/2014 |
| WO | 2015057545 A2 | 4/2015 |
| WO | 2015061668 A1 | 4/2015 |
| WO | 2015089073 A2 | 6/2015 |
| WO | 2015092393 A2 | 6/2015 |
| WO | 2015109124 A2 | 7/2015 |
| WO | 2015143199 A1 | 9/2015 |
| WO | 2015195163 A1 | 12/2015 |
| WO | 2016000619 A1 | 1/2016 |
| WO | 2016004043 A1 | 1/2016 |
| WO | 2016086021 A1 | 6/2016 |
| WO | 2016086036 | 6/2016 |
| WO | 2016179534 | 11/2016 |
| WO | 2016197071 A1 | 12/2016 |
| WO | 2017011618 A1 | 1/2017 |
| WO | 2017223180 A2 | 12/2017 |
| WO | 2018148501 A1 | 8/2018 |
| WO | 2019217459 A1 | 11/2019 |
| WO | 2021030763 A1 | 2/2021 |
| WO | 2021030778 A1 | 2/2021 |
| WO | 2021076546 A1 | 4/2021 |
| WO | 2021076574 A2 | 4/2021 |
| WO | 2021226107 A1 | 11/2021 |
| WO | 2022198196 A1 | 9/2022 |
| WO | 2022213118 A1 | 10/2022 |
| WO | 2022221505 A2 | 10/2022 |
| WO | 2022221550 A1 | 10/2022 |
| WO | 2023201362 A2 | 10/2023 |
| WO | 2023215880 A2 | 11/2023 |

OTHER PUBLICATIONS

McCue et al., Glycogen synthase (GYS1) mutation causes a novel skeletal muscle glycogenosis, Genomics, 2008, 91, pp. 458-466.*
Siegfried et al., "The Clinical Significance of Hepatocyte Growth Factor for Non-Small Cell Lung Cancer," Annals of Thoracic Surgery, vol. 66, pp. 1915-1918 (1998).

Sierra et al., "c-MET as a potential therapeutic target and biomarker in cancer," Therapeutic Advances in Medical :: >ncology, vol. 3, No. 51, pp. 521-535 (2011).
Siggers et al. Conformational dynamics in loop swap mutants of homologous fibronectin type III domains. Biophys J. Oct. 1, 2007 ;93(7):2447-56.
Skerra, et al., "Engineered protein scaffolds for molecular recognition," Journal of Molecular Recognition, 13: 167-187 (2000).
Skolnick et al. From genes to protein structure and function: novel applications of computational approaches in the genomic era. Trends Biotechnol. 18(1 ):34-9, 2000.
Slonomics® Technology Website "https://www.morphosys.com/science/drug-development-capabilities/slonomics", accessed May 12, 2020.
Smith, "Filamentous fusion phage: novel expression vectors that display cloned antigens on the virion surface.", Association of Science (1985) vol. 228, pp. 1315(3).
Song et al. Cancer stem cells—an old idea that's new again: implications for the diagnosis and treatment of breast cancer. Expert Opin Biol Ther 7:4):431-438, 2007.
Stamos et al., "Crystal structure of the HGF b-chain in complex with the Serna domain of the Met receptor," The EMBO Journal, vol. 23, pp. 2325-2335 (2004).
Steiner, et al., "Efficient Selection of DARPins with Sub-nonomolar Affinities using SRP Phage Display," Journal of Molecular Biology, 382: 1211-1227 (2008).
Strand et al., "Site-Specific Radioiodination of HER2-Targeting Affibody Molecules using 4-Iodophenethylmaleimide Decreases Renal Uptake of Radioactivity"; Chemitry Open, vol. 4, pp. 174-182, 2015.
Strohl, William R., "Optimization of Fe-mediated effector functions of monoclonal antibodies," Current Opinion in Biotechnology, vol. 20, pp. 685-691 (2009).
SwissProt Accession No. P00533.2, "Epidermal Growth Factor Receptor," pp. 1-49 (Jun. 11, 2014).
Takahashi et al., "Cutting Edge: 4-1 BB Is a Bona Fide COB T Cell Survival Signal," J Immunol., vol. 162, pp. 0037-5040 (1999).
Tang et al, "Anti-Transferrin Receptor-Modified Amphotericin B-Loaded PLA-PEG Nanoparticles Cure Candidal Meningitis and Reduce Durg Toxicity," Oct. 5, 2015, International Journal of Medicine, 2015:10, pp. 6227-6241.
Tannock and Hill. The Basic Science of Oncology. 1998. New York: McGraw-Hill;; pp. 357-358.
Tie et al., "Safety and efficacy of nivolumab in the treatment of cancers: A meta-analysis of 27 prospective clinical rials," International Journal of Cancer, vol. 140, pp. 948-958, (2017).
Turke et al., "Preexistence and Clonal Selection of MET Amplification in EGFR Mutant NSCLC," Cancer Cell, vol. 17, pp. 77-88 (2010).
Ullrich et al., "Human epidermal growth factor receptor cDNA sequence and aberrant expression of the amplified Jene in A431 epiderrnoid carcinoma cells," Nature, vol. 309, pp. 418-425 (1984).
UniProt Accession No. P10039, accessed Mar. 30, 2023.
Vajdos et al., "Comprehensive funtional maps of the antigen-binding site of an anti-ErbB2 antibody obtained with shotgun scanning mutagenisis", J. Mol. Biol. (2002) 32(2): pp. 415-428.
Van den Burg et al., "Selection of mutations for increased protein stability", Curr. Opin. Biotech. 13:333-337 (2002).
Wang et al., "Vista, a novel mouse Ig superfamily ligand that negatively regulates T cell responses," Journal of Experimental Medicine, vol. 208, No. 3, pp. 577-592 (Mar. 14, 2011).
Watanabe et al., "Gene Cloning of Chitinase A1 from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).
Wattanachaisaereekul, "Production of Polyketides by *Saccharomyces cerevisiae*", Ph.D. Thesis (2007) Center for Microbial Biotechnology, BioCentrum-DTU Technical University of Denmark, pp. 1-187.
Wu, Xiaoqiu, et als, "Elucidation and Structural Modeling of CD71 as a Molecular Target for Cell-Specific Aptamer Binding," J Am Chem Soc , Jul. 10, 2020; 141(27): 10760-10769. doi: 10.1021/jacs.9b0370.

(56) References Cited

OTHER PUBLICATIONS

Xu, et al., "Directed Evolution of High-Affinity Antibody Mimics Using mRNA Display, "Chemistry & Biology, 9: 933-942 (2002).

Yuyu Tan et al., "Selection of Transferrin Receptor-Specific Peptide for Recognition of Cancer Cell," China Science and Technology Papers Online, Apr. 30, 2017, pp. 1-10, Abstract only.

Zhang et al., "Complete disulfide bond assignment of a recombinant immunoglobulin G4 monoclonal antibody," Analytical Biochemistry, vol. 311, pp. 1-9 (2002).

Zhou et al., Characterization of human homologue of 4-1 BB and its ligand, Immunology Letters, vol. 45, pp. p7-p73, 1995.

Zucali, et al., " Role of cMET expression in non-small-cell lung cancer patients treated with eGFR tyrosine kinase inhibitors", Annals of Anocology (2008) 19 :: 1605-1612.

Hackel et al., "Use of 64Cu-Labeled Fibronectin Domain with EGFR-Overexpressing Tumor Xenograft: Molecular Imaging1", Radiology (2012) vol. 263: No. 1 pp. 179-188.

Hackel, et al., "Picomolar Affinity Fibronectin Domains Engineered Utilizing Loop Length Diversity, Recursive Mutagenesis, and Loop Shuffling," Journal of Molecular Biology, 381: 1238-1252 (2008).

Hackel, et al., "Stability and CDR Composition Biases Enrich Binder Functionality Landscapes," Journal of Molecular Biology, 401: 84-96 (2010).

Hallewell et al., "Genetically Engineered Polymers of Human CuZN Superoxide Dismutase," The Journal of Biological Chemistry, vol. 264, No. 9, pp. 5260-5268 (1989).

Hamill et al., "The Effect of Boundary Selection on the Stability and Folding of the Third Fibronectin Type III Domain from Human Tenascin", Biochemistry, 37: 8071-8079 (1998).

Hanes et al, "In vitro selection and evolution of functional proteins by using ribosome display," Proceedings of the National Academy of Sciences USA, vol. 94, pp. 4937-4942 (1997).

Helms et al. Destabilizing loop swaps in the CDRs of an immunoglobulin VL domain. Protein Science 4:2073-2081, 1995.

Hirsch et al, "Combination of EGFR gene copy number and protein expression predicts outcome for advanced non- , mall-cell lung cancer patients treated with gefitnib," Annals of Oncology, vol. 18, pp. 752-760 (2007).

Hoogenboom et al., "Natural and designer binding sites made by phage display technology" Immunology Today (2000) vol. 21, No. 8, pp. 371-378.

Hurtado et al., "Potential role of 4-1 BB in T cell Activation Comparison with the Costimulatory Molecule CD28", Journal of Immunology, vol. 155, pp. 3360-3367, 1995.

Hurtado et al., "Signals through 4-1BB are Costimulatory to previously activated splenic T cells and inhibit activation-induced cell death", Journal of Immunology, vol. 158, pp. 2600-2609, 1997.

Hiylarides et al., "Preparation and in Vivo Evaluation of an N-9p-[125I]1odophenethyl) maleimide—Antibody Conjugate" Bioconjugate Chem., vol. 2, pp. 435-440, 1991.

Hynes et al., "ERBB Receptors and Cancer: the Complexity of Targeted Inhibitors," Nature Reviews, vol. 5, pp. 341-356 (2005).

Ichimura et al., "Expression of c-mel/HGF Receptor in Human Non-small Cell Lung Carcinomas in vitro and in vivo and its Prognostic Significance," Japan Journal of Cancer Research, vol. 87. pp. 1063-1069 (1996).

International Preliminary Report on Patentability dated Apr. 19, 2022 from International Application No. PCT/US2020/055470, International Filing Date Oct. 14, 2020.

International Preliminary Report on Patentability dated Apr. 19, 2022 from International Application No. PCT/US2020/055509, International Filing Date Oct. 14, 2020.

International Search Report and Written Opinion dated Mar. 22, 2021 from International Application No. PCT/US2020/055509, International Filing Date Oct. 14, 2020.

International Search Report and Written Opinion dated Mar. 29, 2021 from International Application No. PCT/US2020/055470, International Filing Date Oct. 14, 2020.

International Search Report and Written Opinion dated Oct. 7, 2022 from International Application No. PCT/US22/24773 (145965.002002), International Filing Date Apr. 14, 2022.

International Search Report and Written Opinion dated Sep. 12, 2022 from International Application No. PCT/US2022024846, International Filing Date Apr. 14, 2022.

International Search Report and Written Opinion from International Application No. PCT/US2021/030863 dated Oct. 29, 2021, International Filing Date May 5, 2021 (145965.002502).

International Search Report and Written Opinion from PCT/US2022/024846 dated Sep. 12, 2022.

Itoh, et al., "Application of Inverse Substrates to Trypsin-Catalyzed Peptid Synthesis", Bioorganic Chemistry (1996) 24, 0007, pp. 59-68.

Jacobs et al., "Design of novel FN3 domains with high stability by a consensus sequence approach," Protein Engineering, Design & Selection, vol. 25, No. 3, pp. 107-117 (2012).

Jacobs et al., "FN3 Domain Engineering", Protein Engineering, pp. 145-162, 2012.

Jacobs et al., "Fusion to a highly stable consensus albumin binding domain allows for tunable pharmacokinetics", Protein Engineering, Design & Selection, vol. 28, No. 10, pp. 385-393, 2015.

Jänne et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, vol. 12, No. 14 Suppl, pP. 4416s-4420s (2006).

Karatan, et al., "Molecular Recognition Properties of FN3 Mono bodies that Bind the Src SH3 Domain," Chemistry & Biology, 11: 835-844 (2004).

Klein et al. "Abstract LB-312: Bispecific Centyrin Simultaneously targeting EGFR and c—Met demonstrates improved ô €?'ctivity compared to the mixture of single agents", Cancer Research, 73 (8 Supplement), Abstract LB-312, Apr. 2013.

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2002).

Koide et al., "High-affinity single-domain binding proteins with a binary-code interface," PNAS, vol. 104, No. 16, pp. 6632-6637(Apr. 17,2017).

Koide, et al., Teaching an Old Scaffold New Tricks: Monobodies Constructed Using Alternative Surfaces of the FN3 Scaffold, Journal of Molecular Biology, 415: 393-405 (2012).

Koide, et al., "The Fibronectin Type III Domain as a Scaffold for Novel Binding Proteins," Journal of Molecular Biology, 284: 1141-1151 (1998).

Koivunen et al. Identification of Receptor Ligands with Phage Display Peptide Libraries J Nucl Med; 40:883-888, 1999.

Kumaran et al., "Confirmationally driven protease-catalyzed splicing of peptide segments: V8 protease-mediated syntheses of fragments derived from thermolysin and ribonuclease A", Protein Science, (1997) 6: pp. 2233-2241.

Kunkel et al., "Rapid and Efficient Site-Specific Mutagenesis without Phenotypic Selection", Methods In Enzymology, (1987) vol. 154 pp. 367-375.

Kuntz. Structure-based strategies for drug design and discovery. Science. 1992 257(5073):1078-1082.

Kwon et al., cDNA sequences of two inducible T-cell genes, Proc. Natl. Acad. Sci., vol. 86, pp. 1963-1967, Mar. 1989.

Angstein et al., "CD137 (ILA/4-1 BB), a Member of the TNF Receptor Family, Induces Monocyte Activation via Bidirectional Signaling," The Journal of Immunology, vol. 160, pp. 2488-2494 (1998).

Langstein et al., "CD137 Induces Proliferation and Endomitosis in Monocytes," Blood, vol. 94, No. 9, pp. 3161-3168 1999).

Langstein et al., Identification of CD137 as a potent monocyte survival factor, Journal of Leukocyte Biology, vol. 65, pp. 829-833, Jun. 1999.

Lazar et al., "Transforming growth factor alpha: mutation of aspartic acid 47 and leucie 48 results in different biological activities", Mol Cell Biol. (1988) 8: pp. 1247-1252.

(56) References Cited

OTHER PUBLICATIONS

Lee et al., "4-1BB Promotes the Survival of COB+ T Lymphocytes by Increasing Expression of Bcl-xL and Bfl-11," The Journal of Immunol., vol. 169, pp. 4882-4888 (2002).

Lee et al., "A Glu-ruea-Lys Ligand-conjugated Lipid nanoparticle/ siRNA System Inhibits Androgen Receptor Expression In Vivo", Molecular Therapy-Nucleic Acids (2016) 5, e348: pp. 1-11.

Lehmann et al., Engineering proteins for thermostability the use of sequence alignments versus rational design and directed evolution, Current Opinion in Biotechnology, vol. 12, pp. 371-375 (2001).

Lejon et al., "Structural basis for the binding of naproxen to human serum albumin in the presence of fatty acids and the GA module", Acta Cryst. (2008) F pp. 64-69.

Lepenies et al., "The Role of Negative Costimulators Dunng Parasitic Infections," Endocrine, Metabolic & Immune Disorders— Drug Targets, vol. 8, pp. 279-288 (2008).

Li et al., "Skin toxicities associated with epidermal growth factor receptor inhibitors," Target Oncology, vol. 4, pp. 107-119 (2009).

Linardou et al., "Somatic EGFR mutations and efficacy of tyrosine kinase inhibitors in NSCLC," National Review of :; linical Oncology, vol. 6, pp. 352-366 (2009).

Lipovsek, et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, 368: 1024-1041 (2007).

Adjei et al., "Early Clinical Development of ARQ197, a Selective, Non-ADP-Competitive Inhibitor Targeting MET Tyrosine Kinase for the Treatment of Advanced Cancers," The Oncologist, vol. 16, pp. 788-799 {2011}.

Alderson et al., "Molecular and Biological Characterization of Human 4-1 BB and its Ligand", Eur. J_ Immunol., vol. N, pp. 2219-2227, 1994.

Alfthan et al., "Properties of a single-chain antibody containing different linker peptides," Protein Engineering, vol. B, No. 7, pp. 725-731 (1995).

Anderson et al., "Towards next generation antisense oligonucleotides: mesylphosphoramidate modification improves therapeutic index and duration of effect of gapmer antisense oligonucleotides," Nucleic Acids Research, 2021, vol. 49, No. 16, Published online Aug. 20, 2021, https://doi.org/10.1093/nar/gkab718, pp. 9026-9041.

Attwood TK. Genomics. The Babel of bioinformatics. Science. 290(5491 ):471-473, 2000.

Basel GA et al., "Critical Update and Emerging Trends in Epidermal Growth Factor Receptor Targeting in Cancer," Journal of Clinical Oncology, vol. 23, No. 11, pp. 2445-2459 (2005).

Bass, et al., "Hormone Phage: An Enrichment Method for Variant Proteins with Altered Binding Properties," Proteins: Structure, Function, and Genetics, 8: 309-314 (1990).

Batley et al., "Inhibition of FGF-1 Receptor Tyrosine Kinase Activity By PD 161570, a New Protein-Tyrosine Kinase nhibitor," Life Sciences, vol. 62, No. 20, pp. 143-150 (1998).

Bean et al., "MET amplification occurs with or without T790M mutations in EGFR mutant lung tumors with acquired esistance to gefilinib or erlotinib," Proceedings of the National Academy of Science, vol. 104, No. 52, pp. 0932-20937 (2007).

Binz et al., "High-affinity binders selected from designed ankyrin repeat protein libraries," Nature Biotechnology, vol. e2, No. 5, pp. 575-582 (May 2004).

Binz, et al., "Engineered proteins as specific binding reagents," Current Opinion in Biotechnology, 16: 459-469 (2005).

Birtalan et al., "The Intrinsic Contributions of Tyrosine, Serine, Glycine and Arginine to the Affinity and Specificity of Antibodies," Journal of Molecular Biology, vol. 377, pp. 1518-1528 (2008).

Bork et al., "Proposed acquisition of an animal protein domain by bacteria," Proceedings of the National Academy of Science, USA, vol. 89, pp. 8990-8994 (1992).

Brown et al., "Tolerance of single, but not multiple, amino acid replacements in antibody VH CDR 2: a means of minimizing B cell wastage from somatic hypermutation", J. Immuno. (1996) pp. 3285-3291.

Burgess et al., "Possible dissociation of the heparin-binding and mitogenic activities of heparin-binding (acidic fibroblast) growth factor-1 from its receptor-binding activities by site-directed mutagenesis of a single lysine residue" J Cell Biol (1990) 111:pp. 2129-2138.

Burton Earle Barnett et al: "Disclosures", Blood, vol. 128, No. 22, Dec. 2, 2016 (Dec. 2, 2016), pp. 4557-4557, KP055711182, US ISSN: 0006-4971, doi: 10.1182/blood.V128.22.4557.4557 *abstract*.

C.N. Pace, "Determination and Analysis of Urea and Guanidine Hydrochloride Denaturation Curves," Methods in Enzymology, 131: 266-280 (1986).

Candelaria, Pierre V. , et al, "Antibodies Targeting the Transferrin Receptor 1 (TfR1) as Direct Anti-Cancer Agents," Frontiers in Immunology (www.frontiersin.org), Mar. 2021, vol. 12, Article 607692.

Capellas, "Enzymatic Condensation of Cholecystokinin CCK-8 (4-6) and CCK-8 (7-8) Peptide Fragments in Organic Media", Biotechnology and Bioengineering (1997) vol. 56, No. 4, pp. 456-463.

Cappuzzo et al., "Epidermal Growth Factor Receptor Gene and Protein and Gefilinib Sensitivity in Non-small-Cell lung Cancer," Journal of the National Cancer Institute, vol. 97, pp. 643-655 (2005).

Chen et al., "Cell-Surface Display of Heterologous Proteins: From High-Throughput Screening to Environmental Applications", Biotechnology and Bioengineering, (2002) vol. 79, No. 5, pp. 496-503.

Chiba et al., Amyloid Fibril Formation in the Context of Full-length Protein Effects of Praline mutations on the Amyloid fibril formation of b2-Microglobulin, Journal of Biological Chemistry, vol. 278, No. 47, pp. 47016-47024, Nov. 2003.

Christensen et al., "c-Met as a target for human cancer and characterization of inhibitors for therapeutic ntervention," Cancer Letters, vol. 225, pp. 1-26 (2005).

Clarke, et al., "Folding and Stability of a Fibronectin Type III Domain of Human Tenascin," Journal of Molecular Biology, 270: 771-778 (1997).

Cooper et al., "4-1 BB (CD 137) controls the clonal expansion and survival of COB T cells in vivo but does not t: ntribute the development of cytotoxicity", Eur. J_ Immunol., vol. 32, pp. 521-529, 2002.

Cooper et al., "Molecular cloning of a new transforming gene from a chemically transformed human cell line," Nature, vol. 311, pp. 29-33 (1984).

Cota, et al., "Two Proteins with the Same Structure Respond very Differently to Mutation: The Role of Plasticity in Protein Stability", Journal of Molecular Biology, 302, 713-725 (2000).

DeBenedette et al., "Role of 4-1BB Ligand in Costimulation of T Lymphocyte Growth and its Upregulation on M12 B rymphomas by cAMP," J_ Exp_ Med., vol. 181, pp. 985-992 (1995).

Dehouck, et al., "Fast and accurate predictions of protein stability changes upon mutations using statistical potentials and neural networks: PoPMuSiC-2.0," Bioinformatics, 25(19): 2537-2543 (2009).

DeRoock et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, vol. 11, pp. 753-762 (2010).

Diem et al., "Selection of high-affinity Centyrin FN3 domains from a simply library diversified at a combination of strand and loop positions." Protein Engin Design (2014) Selection 27(10): 419-429.

Dineen, et al., "The Adnectin CT-322 is a novel VEGF receptor 2 inhibitor that decreases tumor burden in an orthotopic mouse model of pancreatic cancer," BMC Cancer, 8: 352-361 (2008).

Downward et al., "Autophosphorylation sites on the epidermal growth factor receptor," Nature, vol. 311, pp. 183-485 ( 1984).

Dutta, et al., "High-affinity fragment complementation of a fibronectin type III domain and its application to stability enhancement," Protein Science, 14: 2838-2848 (2005).

(56)　　　　　References Cited

OTHER PUBLICATIONS

Engelman et al., "MET Amplification Leads to Gefitinib Resistance in Lung Cancer by Activating ERBB3 Signaling," Science, vol. 316, pp. 1039-1043 (2007).

Falvo, Elisabetta et al, "High Activity and Low Toxicity of a Novel CD71-Targetiong Nanotherapeutic Named The-0504 on Preclinical Models of Several Human Aggressive Tumors," Journal of Experimental Clinical Cancer Research, (2021) 40:63; https://doi.org/10.1186/s13046-021-01851-8, pp. 1-14.

Ferguson, Kathryn M., "Structure-Based View of Epidermal Growth Factor Receptor Regulation," Annual Review of Biophysics, vol. 37, pp. 535-373 (2008).

Final Office Action mailed on Jul. 10, 2020 in U.S. Appl. No. 15/637,276 (145965.00921).

Final Office Action mailed on Jul. 21, 2020 in U.S. Appl. No. 16/218,990 (145965.000701).

Garcia-Ibilcieta, et al., "Simple method for production of randomized human tenth fibronectin domain III libraries for use in combinatorial screening procedures," Bio Technologies, 44: 559-562 (2008).

Garon et al., "Pembrolizumab for the Treatment of Non-Small-Cell Lung Cancer," The New England Journal of Medicine, vol. 372, No. 21, pp. 2018-2028 (May 21, 2015).

Garrard, et al., "Selection of an anti-IGF-1 Fab from a Fab phage library created by mutagenesis of multiple CDR loops," Gene, 128: 103-109 (1993).

GenBank Accession No. NP 001120972, accessed May 12, 2020.

GenBank Accession No. NP_002151, accessed May 12, 2020.

Getmanova, et al., "Antagonists to Human and Mouse Vascular Endothelial Growth Factor Receptor 2 Generated by Directed Protein Evolution In Vitro," Chemistry & Biology, 13: 549-556 (2006).

Gill et al., "Monoclonal Anti-epidermal Growth Factor Receptor Antibodies Which Are Inhibitors of Epidermal Growth racier Binding and Antagonists of Epidermal Growth Factor-stimulated tyrosine Protein Kinase Activity," The Journal Jf Biological Chemistry, vol. 259, No. 12, pp. 7755-7760 (1984).

Goldberg et al., "Engineering a Targeted Delivery Platform using Centyrins" Protein Engineering, Design & selection, vol. 29, No. 12, pp. 563-572, 2016.

Goldstein et al., "Biological efficacy of a chimeric antibody to the epidermal growth factor receptor in a human umor kenografl model," Clinical Cancer Research, vol. 1, pp. 1311-1318 (1995).

Gramaglia et al., "Co-stimulation of antigen-specific CD4 T cells by 4-1BB ligand," Eur. J. Immunol., vol. 30, pp. 92-402 (2000).

Grünwald et al., "Developing Inhibitors of the Epidermal Growth Factor Receptor for Cancer Treatment," Journal of he National Cancer Institute, vol. 95, No. 12, pp. 851-867 (2003).

Non-Final Office Action mailed on Aug. 30, 2023 in U.S. Appl. No. 17/720,422 (10 pages).

Non-Final Office Action mailed on Oct. 18, 2023 in 17720996, 23 pages.

Lohse et al., Fluorescein-Conjugated Lysine monomers for Solid Phase Synthesis of Fluorescent Peptides and PNA Pligomers Bioconjugate Chem, vol. 8, pp. 503-509, 1997 .pdf.

Ma et al., "c-Met: Structure, functions and potential for therapeutic inhibition," Cancer and Metastasis Reviews, vol. 22 pp. 309-325 (2003).

Makkouk Amani et al: "Rationale for anti-CD137 cancer immunotherapy", European Journal of Cancer, Elsevier, Amsterdam, NL, vol. 54, Jan. 2, 2016 (Jan. 2, 2016), pp. 112-119, XP029401784, ISSN: 0959-8049, DOI: 10.1016/j.ejca.2015.09.026 *abstract p. 114, right-hand column, paragraph 4—p. 116, right-hand column paragraph 1table 1*.

Mamluk et al., "Anti-tumor effect of CT-322 as an Adnectin inhibitor of vascular endothelial growth factor receptor-2", mAbs, 2(2), pp. 199-208, 2010.

Mattheakis et al., "An in vitro polysome display system for identifying ligands from very large peptide libraries", Proc. Natl. Acad. Sci. (1994) Vo . . . 91, pp. 9022-9026.

Maus et al., Ex vivo expansion of polyclonal and antigen-specific cytotoxic T lymphocytes by artificial APCs Expressing ligands for the T-cell receptor, CD28 and 4-1BB Nature Biotechnology, vol. 20, pp. 143-148, Feb. 2002.

McCracken, "Non-invasive monitoring of hematopoietic reconstitution and immune cell function through Positron Emission Tomography" University of California, Los Angeles, Dissertaton ProQuest LLC (2014) pp. 1-202.

McLaughlin et al., "Quantitative Assessmenet of the Heterogeneity of PD-L 1 Expression in Non-small Cell Lung Cancer (NSCLC)," JAMA Oncol., vol. 2, No. 1, pp. 46-54, (Jan. 2016).

Meinke et al., "Cellulose-Binding Polypeptides from Cellulomonas fimi: Endoglucanase D (CenD), a Family A b-1,4-Glucanase," Journal of Bactenology, vol. 175, No. 7, pp. 1910-1918 (1993).

Mendelsohn et al., "Epidermal Growth Factor Receptor Targeting in Cancer," Seminars in Oncology, vol. 33, pp. 369-385 (2006).

Mendelsohn et al., "The EGF receptor family as targets for cancer therapy," Oncogene, vol. 19, pp. 6550-6565 2000).

Michel et al., "CD137-induced apoptosis is independent of CD95," Immunology, vol. 98, pp. 42-46 (1999).

Michel et al., "Expression of soluble CD137 correlates with activation-induced cell death of lymphocytes", Cytokine, vol. 12, No. 6, pp. 742-746, 2000.

Miller et al Ligand binding to proteins: the binding landscape model. Protein Sci. Oct. 1997;6(10):2166-79.

Määttä et al., "Proteolytic Cleavage and Phosphorylation of a Tumor-associated ErbB4 Isoform Promote Ligand-ndependent Survival and Cancer Cell Growth," Molecular Biology, vol. 17, pp. 67-79 (2006).

Natarajan, et al., "A Novel Engineered Anti-CD20 Tracer Enables Early Time PET Imaging in a Humanized Transgenic Mouse Model of B-cell Non-Hodgkins Lymphoma", Clin Cancer Res (2013) 19: pp. 6820-6829.

NCBI Reference Sequence NP _005219.2, "Epidermal Growth Factor Receptor Isoform a Precursor [Homo sapiens]," pp. 1-14 (May 18, 2014).

Non-Final Office Action dated Dec. 1, 2022, from U.S. Appl. No. 17/070,337 (145965.002301).

Non-Final Office Action dated Feb. 10, 2022 in U.S. Appl. No. 16/218,990 (145965.000701).

Non-Final Office Action for U.S. Appl. No. 17/070,337 dated Dec. 1, 2022.

Non-Final Office Action mailed on Feb. 3, 2021 in U.S. Appl. No. 16/218,990 (145965.00701).

Non-Final Office Action mailed on Jul. 9, 2021 in 16821064 (145965.001211).

Non-Final Office Action mailed on Aug. 18, 2021 in U.S. Appl. No. 16/801,787(145965.0001311).

Non-Final Office Action mailed on Sep. 24, 2021 in U.S. Appl. No. 16/820,844 (145965.001411).

Non-Final Office Action mailed on Feb. 4, 2022 in U.S. Appl. No. 16/801,787 (145965.001311).

Notice of Allowance dated Nov. 28, 2022 in U.S. Appl. No. 17/070,020 (145965.002101).

Notice of Allowance for U.S. Appl. No. 17/070,020 dated Nov. 28, 2022 and updated on Jan. 17, 2023 (145965.002101).

Notice of Allowance for U.S. Appl. No. 17/070,337 dated May 24, 2023.

Notice of Allowance mailed Mar. 3, 2020 in U.S. Appl. No. 15/840,303 (145965.01401).

Odegrip et al., "CIS display: In vitro selection of peptides from libraries of protein-DNA complexes," Proceedings of he National Academy of Science USA, vol. 101, No. 9, pp. 2806-2810 (2004).

Olson et al., "Design, expression, and stability of a diverse protein library based on the human fibronectin type III ô €,?omain," Protein Science, vol. 16, pp. 476-484 (2007).

Olson, William C. et al., "Antibody-drug Conjugates Targeing Prostate-Specific Membrane Antigen," Frontiers in Bioscience (Landmark Edition) 19: pp. 12-33, Jan. 1, 2014.

Pace, "Determination and Analysis of Urea and Guanidine Hydrochloride Denaturation Curves", Methods in Enzymology (1986) vol. 131, pp. 266-280.

(56)         References Cited

OTHER PUBLICATIONS

Panek et al.,"In Vitro Pharmacological Characterization of PD 166285, a New Nanomolar Potent and Broadly Active Protein Tyrosine Kinase Inhibitor," The Journal of Pharmacology and Experimental Therapeutics, vol. 283, No. 3, pp. 1433-1444 (1997).

Parker, et al., "Antibody mimics based on human fibronectin type three domain engineered for thermostability and high-affinity binding to vascular endothelial growth factor receptor two," Protein Engineering, Design & Selection, 18(9): 435-444 (2005).

Pauly et al., CD137 is expressed by follicular dendritic cells and costimulates B lymphocyte activation in germinal t; enters, Journal of Leukocyte Biology, vol. 72, pp. 35-42, Jul. 2002.

Peters et al., "MET: a promising anticancer therapeutic target," Nature Reviews Clinical Oncology, vol. 9, pp. 314-326 (2012).

Prewett et al., "Mouse-Human chimeric Anti-Epidermal Growth Factor Receptor Antibody C225 Inhibits the Growth Jf Human Renal Cell Carcinoma Xenografls in Nude Mice," Clinical Cancer Research, vol. 4, pp. 2957-2966 (1998).

Reiss et al. Inhibition of platelet aggregation by grafting RGD and KGD sequences on the structural scaffold of small disulfide-rich proteins. Platelets 17(3):153-157, 2006.

Riel Yet al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, vol. 12, No. 3, pp. g39-g844 (2006).

Roberts et al., "RNA-peptide fusions for the in vitro selection of peptides and proteins," Proceedings of the National Academy of Science USA, vol. 94, pp. 12297-12302 (1997).

Robinson et al., "Covalent Attachment of Arc Repressor Subunits by a Peptide Linker Enhances Affinity for Operator DNA," Biochemistry, vol. 35, pp. 109-116 (1996).

Rudikoff el al., "Single amino acid substitution altering antigen-binding specificity", Proc Natl Acad Sci (1982) 79(6): pp. 1979-1983.

Rybalov et al., "PSMA, EpCAM, VEGF and GRPR as Imaging Targets in Locally Recurrent Prostate Cancer after Radiotherapy", Int. J. Mol. Sci. (2014) 15, pp. 6046-6061.

Sakakura et al., "Gains, Losses, and Amplifications of Genomic Materials in Primary Gastric Cancers Analyzed by :; omparative Genomic Hybridization," Genes, Chromosomes & Cancer, vol. 24, pp. 299-305 (1999).

Schmidt et al., "Novel mutations of the MET proto-0ncogene in papillary rental carcinomas," Oncogene, vol. 18, pp. 343-2350 (1999).

Schwarz et al., "ILA, a Member of the Human Nerve Growth FactorfTumor Necrosis Factor Receptor Family, Regulates T-Lymphocyte Proliferation and Survival," Blood, vol. 87, No. 7, pp. 2839-2845 (Apr. 1, 1996).

Shalom D. Goldberg et al: "Engineering a targeted delivery platform using Centyrins", Protein Engineering, Design and Selection, Oct. 13, 2016 (Oct. 13, 2016), XP055384705, GB ISSN: 1741-0126, DOI: 10.1093/protein/gzw054 *abstract p. 564, left-hand column, paragraph 2—right-hand column line 3 p. 567, right-hand column, paragraph 2 p. 568, right-hand column paragraph 2—p. 569, left-hand column paragraph 2table I**figure 1a*.

Shuford et al., "4-18B Costimulatory Signals Preferentially Induce COB+ T Cell Proliferation and Lead to the amplification In Vivo of Cytotoxic T Cell Responses," J_ Exp_ Med., vol. 186, No. 1, pp. 47-55 (Jul. 7, 1997).

Brewer, et al., Cell Metabolism, "Targeting Pathogenic Lafora Bodies in Lafora Disease Using an Antibody-Enzyme Fusion", CellPress 30, 689-705, Oct. 1, 2019, https://doi.org/10.1016/j.cmet.2019.07.002.

Varea, et al., "Suppression of glycogen synthesis as a treatment for Lafora disease: Establishing the window of opportunity", Neurobiology of Disease 147 (2021) 105173, https://doi.org/10.1016/j.nbd.2020.105173!.

Nitschke, et al., "An inducible glycogen synthase-1 knockout halts but does not reverse Lafora disease progression in mice", https://doi.org/10.1074/jbc.RA120.015773; American Society for Biochemistry and Molecular Biology, J. Biol. Chem. (2021) 296 100150.

Duran, et al., "Glycogen accumulation underlies neurodegeneration and autophagy impairment in Lafora disease", Human Molecular Genetics, 2014, vol. 23, No. 12 3147-3156 doi:10.1093/hmg/ddu024; Advance Access published on Jan. 22, 2014.

Soudah et al., "AntimiR-155 Cyclic Peptide-PNA Conjugate: Synthesis, Cellular Uptake, and Biological Activity", ACS Omega, 2019, 4(9):13954-13961.

Coutinho, et al., "Genetic Substrate Reduction Therapy: A Promising Approach for Lysosomal Storge Disorders", Diseases 2016, vol. 4, Issue 33.

Almodovar-Paya, et al., "Preclinical Research in Glycogen Storage Diseases: A Comprehensive Review of Current Animal Models", Int. J. Mol. Sci. 2020, vol. 21, 9621.

Notification of Transmittal of International Preliminary Report of Patentability, PCT/US2023/065812, Sep. 16, 2024.

* cited by examiner

CD71 BINDING FIBRONECTIN TYPE III DOMAINS

CROSS-REFERENCE TO RELATED APPLICATIONS

The present application is a continuation of U.S. Non-Provisional application Ser. No. 17/070,020, filed Oct. 14, 2020, now U.S. Pat. No. 11,628,222, issued Apr. 18, 2023, which claims priority to U.S. Provisional Application No. 62/914,643, filed Oct. 14, 2019, and U.S. Provisional Application No. 62/949,020, filed on Dec. 17, 2019, each of which is hereby incorporated by reference in its entirety.

REFERENCE TO AN ELECTRONIC SEQUENCE LISTING

The application contains a Sequence Listing which has been submitted electronically in XML format and is hereby incorporated by reference in its entirety. The Sequence Listing is named "ROO-021USCI Sequence Listing.xml", was created on Jan. 7, 2025, and is 311,296 bytes in size.

FIELD

The present embodiments relate to fibronectin type III domains (FN3) that specifically bind cluster of differentiation 71 (CD71) and methods of making and using the molecules.

BACKGROUND

CD71, also known as transferrin receptor 1, is transmembrane that is essential for iron transport into cells. It is highly expressed on many tumor types and at the blood brain barrier, and has thus become an important target for drug delivery. Following binding to iron loaded transferrin, CD71 is rapidly endocytosed and efficiently recycled back to the cell surface. Studies with CD71 antibody drug conjugates suggest that targeting CD71 can improve specificity and selectivity of drug delivery and widen the therapeutic index. In addition, studies using anti-CD71 monoclonal antibodies indicate that binding affinity can play an important role in enabling blood brain barrier transcytosis. Antibodies with high affinity for CD71 are rapidly internalized and alter normal receptor trafficking so that instead of recycling, the receptor is targeted to the lysosome for degradation. In contrast, antibodies with low affinity for CD71 allow for receptor recycling and higher brain exposure.

While antibodies or antibody fragments are the most widely used class of therapeutic proteins when high affinity and specificity for a target molecule are desired, non-antibody proteins can be engineered to also bind such targets. These "alternative scaffold" proteins have advantages over traditional antibodies due to their small size, lack of disulphide bonds, high stability, ability to be expressed in prokaryotic hosts, easy purification, and they are easily conjugated to drugs/toxins, penetrate efficiently into tissues and are readily formatted into multispecific binders.

One such alternative scaffold is the immunoglobulin (Ig) fold. This fold is found in the variable regions of antibodies, as well as thousands of non-antibody proteins. It has been shown that one such Ig protein, the tenth fibronectin type III (FN3) repeat from human fibronectin, can tolerate a number of mutations in surface exposed loops while retaining the overall Ig-fold structure. Thus, what is needed is a FN3 domain that can specifically bind to CD71, and methods of using such molecules for cancer therapy.

SUMMARY

In some embodiments, FN3 domains (e.g. polypeptides) that specifically bind CD71 protein are provided. In some embodiments, the FN3 domains are isolated. In some embodiments, the FN3 domains are recombinant. In some embodiments, the FN3 domains are non-naturally occurring.

In some embodiments, FN3 domains are provided that comprise the amino acid sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61 or 62. In some embodiments, FN3 domains are provided that comprise the amino acid sequence of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149. In some embodiments, FN3 domains are provided that comprise the amino acid sequence of SEQ ID NOs: 81-309. In some embodiments, the FN3 domains bind to CD71. In some embodiments, the FN3 domain binds to human CD71 at a site on CD71 that does not compete with transferrin binding to CD71. In some embodiments, FN3 domains are provided that comprise the amino acid sequence of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149. In some embodiments, the FN3 domains specifically bind to CD71. In some embodiments, the polypeptide is provided that comprises more than one FN3 domains connected by a linker, such as a flexible linker. In some embodiments, the polypeptide comprises 2, 3, or 4 FN3 domains that are connected to one another by one or more linkers between the domains.

In some embodiments, isolated polynucleotides encoding the FN3 domains described herein are provided.

In some embodiments, a vector comprising the polynucleotides described herein are provided.

In some embodiments, a host cell comprising the vectors described herein are provided.

In some embodiments, methods of producing the FN3 domains are provided. In some embodiments, the method comprises culturing a host cell comprising a vector encoding or expressing the FN3 domain. In some embodiments, the method further comprises purifying the FN3 domain. In some embodiments, the FN3 domain specifically binds CD71.

In some embodiments, pharmaceutical compositions comprising a FN3 domain that binds to CD71 and a pharmaceutically acceptable carrier are provided.

In some embodiments, anti-idiotypic antibodies that binds a FN3 domain that binds to CD71 are provided.

In some embodiments, kits comprising one or more of the FN3 domains are provided.

In some embodiments, methods of detecting CD71-expressing cancer cells in a tumor tissue are provided. In some embodiments, the method comprises obtaining a sample of the tumor tissue from a subject and detecting whether CD71 protein is expressed in the tumor tissue by contacting the sample of the tumor tissue with the FN3 domain that binds CD71 protein comprising the amino acid sequence of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309 and detecting the binding between CD71 protein and the FN3 domain.

In some embodiments, methods of isolating CD71 expressing cells are provided. In some embodiments, the method comprises obtaining a sample from a subject; contacting the sample with the FN3 domain that binds CD71 protein comprising the amino acid sequence of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309 and isolating the cells bound to the FN3 domains.

In some embodiments, methods of detecting CD71-expressing cancer cells in a tumor tissue are provided. In some embodiments, the method comprises conjugating the FN3 domain that binds CD71 protein comprising the amino acid sequence of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309 to a detectable label to form a conjugate; administering the conjugate to a subject; and visualizing the CD71 expressing cancer cells to which the conjugate is bound.

In some embodiments, methods of treating cancer in a subject in need thereof are provided. In some embodiments, the method comprises administering a polypeptide that binds to CD71. In some embodiments, that the polypeptide is a FN3 domain that binds to CD71. In some embodiments, the polypeptide comprises a sequence such as SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, 149, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309, or a polypeptide as provided herein that is linked to or conjugated to a therapeutic agent.

In some embodiments, methods of treating a neurological condition and/or a brain tumor are provided. In some embodiments, the methods comprise administering to the subject a polypeptide or the pharmaceutical composition as provided herein. In some embodiments, the brain tumor is selected from the group consisting of nonmalignant, benign, and malignant brain tumors.

In some embodiments, methods of delivering an agent of interest to a CD71 positive cell are provided. In some embodiments, the methods comprise contacting a cell with the agent of interest coupled to a FN3 domain that binds to CD71, such as a polypeptide as provided herein. In some embodiments, the agent of interest is a chemotherapeutic agent, a drug, a growth inhibitory agent, a toxin, a radioactive isotope, an anti-tubulin agent, a polynucleotide, a siRNA molecule, an antisense molecule, a RNA molecule, a DNA molecule, DNA minor groove binders, DNA replication inhibitors, alkylating agents, antibiotics, antifolates, antimetabolites, chemotherapy sensitizers, topoisomerase inhibitors, or a *vinca* alkaloid.

In some embodiments, the polypeptide is a FN3 protein that binds to CD71 at a site that does not compete or inhibit transferrin binding to CD71.

In some embodiments, methods of identifying a FN3 protein that binds to CD71 at a site that does not compete or inhibit transferrin binding to CD71 are provided.

DETAILED DESCRIPTION OF THE DISCLOSURE

As used in this specification and the appended claims, the singular forms "a," "an," and "the" include plural referents unless the content clearly dictates otherwise. Thus, for example, reference to "a cell" includes a combination of two or more cells, and the like.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993: Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the 3rd FN3 domain of tenascin (TN3), or the 10th FN3 domain of fibronectin (FN10).

The term "capture agent" refers to substances that bind to a particular type of cells and enable the isolation of that cell from other cells. Exemplary capture agents are magnetic beads, ferrofluids, encapsulating reagents, molecules that bind the particular cell type and the like.

"Sample" refers to a collection of similar fluids, cells, or tissues isolated from a subject, as well as fluids, cells, or tissues present within a subject. Exemplary samples are tissue biopsies, fine needle aspirations, surgically resected tissue, organ cultures, cell cultures and biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium and lavage fluids and the like.

"Substituting" or "substituted" or 'mutating" or "mutated" refers to altering, deleting of inserting one or more amino acids or nucleotides in a polypeptide or polynucleotide sequence to generate a variant of that sequence.

"Variant" refers to a polypeptide or a polynucleotide that differs from a reference polypeptide or a reference polynucleotide by one or more modifications for example, substitutions, insertions or deletions. "Specifically binds" or "specific binding" refers to the ability of a FN3 domain to bind to its target, such as CD71, with a dissociation constant ($K_D$) of about $1\times10^{-6}$ M or less, for example about $1\times10^{-7}$ M or less, about $1\times10^{-8}$ M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. Alternatively, "specific binding" refers to the ability of a FN3 domain to bind to its target (e.g. CD71) at least 5-fold above a negative control in standard ELISA assay. In some embodiments, a negative control is an FN3 domain that does not bind CD71. In some embodiment, an FN3 domain that specifically binds CD71 may have cross-reactivity to other related antigens, for example to the same predetermined antigen from other species (homologs), such as *Macaca Fascicularis* (cynomolgous monkey, cyno) or *Pan troglodytes* (chimpanzee).

"Library" refers to a collection of variants. The library may be composed of polypeptide or polynucleotide variants.

"Stability" refers to the ability of a molecule to maintain a folded state under physiological conditions such that it retains at least one of its normal functional activities, for example, binding to a predetermined antigen such as CD71.

"CD71" refers to human CD71 protein having the amino acid sequence of SEQ ID NOs: 32 or 80. In some embodiments, SEQ ID NO: 32 is full length human CD71 protein. In some embodiments, SEQ ID NO: 80 is the extracellular domain of human CD71.

"Tencon" refers to the synthetic fibronectin type III (FN3) domain having the sequence shown in SEQ ID NO: 1 and described in U.S. Pat. Publ. No. 2010/0216708.

A "cancer cell" or a "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

"Vector" refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than about 50 amino acids may be referred to as "peptides".

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Subject" includes any human or nonhuman animal. "Nonhuman animal" includes all vertebrates, e.g., mammals and non-mammals, such as nonhuman primates, sheep, dogs, cats, horses, cows chickens, amphibians, reptiles, etc. Except when noted, the terms "patient" or "subject" are used interchangeably.

"Isolated" refers to a homogenous population of molecules (such as synthetic polynucleotides or a polypeptide such as FN3 domains) which have been substantially separated and/or purified away from other components of the system the molecules are produced in, such as a recombinant cell, as well as a protein that has been subjected to at least one purification or isolation step. "Isolated FN3 domain" refers to an FN3 domain that is substantially free of other cellular material and/or chemicals and encompasses FN3 domains that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

Compositions of Matter

In some embodiments, proteins comprising a polypeptide comprising an amino acid sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309 are provided. In some embodiments, proteins comprising a polypeptide comprising an amino acid sequence that is at least 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to a sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309. In some embodiments, the protein is at least 85%, 86%, 87%, 88%, 89%, 90%, 91%, 92%, 93%, 94%, 95%, 96%, 97%, 98% or 99% identical to a sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309. In some embodiments, the protein is at least 90%, 91%, 92%, 93%, 94%, 95%, 96%, 97%, 98% or 99% identical to a sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309. In some embodiments, the protein is at least 95%, 96%, 97%, 98% or 99% identical to a sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309.

The polypeptides provided herein can be part of a larger polypeptide and can be referred to as a domain. The homology or identity between two domains in different polypeptides is based on the domains that are similar as opposed to the overall polypeptide. For example, if a polypeptide comprises a polypeptide comprising a FN3 domain comprising SEQ ID NO: 81 and said domain is conjugated to a scFV antibody, another protein that has a domain that is similar but not identical to SEQ ID NO: 81 can be at least 90% identical even if the scFV shares no homology. Thus, the % identity can be based on the domain or on the entire length of the polypeptide. Methods of determining % identity are provided for herein or are known to one of skill in the art.

In some embodiments, fibronectin type III (FN3) domains that bind or specifically bind human CD71 protein (SEQ ID NOs: 32 or 80) are provided. As provided herein, the FN3 domains can bind to the CD71 protein. Also provided, even if not explicitly stated is that the domains can also specifically bind to the CD71 protein. Thus, for example, a FN3 domain that binds to CD71 would also encompass a FN3 domain protein that specifically binds to CD71. These molecules can be used, for example, in therapeutic and diagnostic applications and in imaging. In some embodiments, polynucleotides encoding the FN3 domains disclosed herein or complementary nucleic acids thereof, vectors, host cells, and methods of making and using them are provided.

In some embodiments, an isolated FN3 domain that binds or specifically binds CD71 is provided.

In some embodiments, the FN3 domain comprises two FN3 domains connected by a linker. The linker can be a flexible linker. The linker can be a short peptide sequence, such as those described herein. For example, the linker can be a G/S linker and the like.

In some embodiments, the FN3 domain may bind CD71 with a dissociation constant ($K_D$) of less than about $1 \times 10^{-7}$ M, for example less than about $1 \times 10^{-8}$ M, less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffers described herein. In some embodiments, the FN3 domain may bind CD71 at least 5-fold above the signal obtained for a negative control in a standard ELISA assay.

In some embodiments, the FN3 domain that binds or specifically binds CD71 comprises an initiator methionine (Met) linked to the N-terminus of the molecule. In some embodiments, the FN3 domain that binds or specifically binds CD71 comprises a cysteine (Cys) linked to a C-terminus of the FN3 domain. The addition of the N-terminal Met and/or the C-terminal Cys may facilitate expression and/or conjugation of half-life extending molecules.

The FN3 domain can also contain cysteine substitutions, such as those that are described in U.S. Pat. No. 10,196,446, which is hereby incorporated by reference in its entirety. Briefly, in some embodiments, the polypeptides provided herein can comprise at least one cysteine substitution at a position selected from the group consisting of residues 6, 8, 10, 11, 14, 15, 16, 20, 30, 34, 38, 40, 41, 45, 47, 48, 53, 54, 59, 60, 62, 64, 70, 88, 89, 90, 91, and 93 of the FN3 domain based on SEQ ID NO: 6 or SEQ ID NO: 1 of U.S. Pat. No. 10,196,446, and the equivalent positions in related FN3 domains. In some embodiments, the substitution is at residue 6. In some embodiments, the substitution is at residue 8. In some embodiments, the substitution is at residue 10. In some embodiments, the substitution is at residue 11. In some embodiments, the substitution is at residue 14. In some embodiments, the substitution is at residue 15. In some embodiments, the substitution is at residue 16. In some embodiments, the substitution is at residue 20. In some embodiments, the substitution is at residue 30. In some embodiments, the substitution is at residue 34. In some embodiments, the substitution is at residue 38. In some embodiments, the substitution is at residue 40. In some embodiments, the substitution is at residue 41. In some embodiments, the substitution is at residue 45. In some embodiments, the substitution is at residue 47. In some embodiments, the substitution is at residue 48. In some embodiments, the substitution is at residue 53. In some embodiments, the substitution is at residue 54. In some embodiments, the substitution is at residue 59. In some embodiments, the substitution is at residue 60. In some embodiments, the substitution is at residue 62. In some embodiments, the substitution is at residue 64. In some embodiments, the substitution is at residue 70. In some embodiments, the substitution is at residue 88. In some embodiments, the substitution is at residue 89. In some embodiments, the substitution is at residue 90. In some embodiments, the substitution is at residue 91. In some embodiments, the substitution is at residue 93.

A cysteine substitution at a position in the domain or protein comprises a replacement of the existing amino acid residue with a cysteine residue. Other examples of cysteine modifications can be found in, for example, U.S. Patent Application Publication No. 20170362301, which is hereby incorporated by reference in its entirety. The alignment of the sequences can be performed using BlastP using the default parameters at, for example, the NCBI website.

In some embodiments, the FN3 domain that binds CD71 is internalized into a cell. In some embodiments, internalization of the FN3 domain may facilitate delivery of a detectable label or therapeutic into a cell. In some embodiments, internalization of the FN3 domain may facilitate delivery of a cytotoxic agent into a cell. The cytotoxic agent can act as a therapeutic agent. In some embodiments, internalization of the FN3 domain may facilitate the delivery of any detectable label, therapeutic, and/or cytotoxic agent disclosed herein into a cell. In some embodiments, the cell is a tumor cell. In some embodiments, the cell is a liver cell.

In some embodiments, the FN3 domain that binds CD71 is based on Tencon sequence of SEQ ID NO: 1 or Tencon 27 sequence of SEQ ID NO: 4, optionally having substitutions at residues positions 11, 14, 17, 37, 46, 73, or 86 (residue numbering corresponding to SEQ ID NO: 4).

In some embodiments, an isolated FN3 domain that binds CD71 comprises the amino acid sequence of SEQ ID NOs: 33, 34, 35, 36, 37, 38, 39, 40, 41, 42, 43, 44, 45, 46, 47, 48, 49, or 50.

In some embodiments, an isolated FN3 domain that binds CD71 comprises the amino acid sequence of SEQ ID NOs: 51, 52, 53, 54, 55, 56, 57, 58, 59, 60, or 61.

In some embodiments, an isolated FN3 domain that binds CD71 comprises the amino acid sequence of SEQ ID NO: 33.

In some embodiments, an isolated FN3 domain that binds CD71 comprises the amino acid sequence of SEQ ID NO: 34.

In some embodiments, an isolated FN3 domain that binds CD71 comprises the amino acid sequence of SEQ ID NO: 35.

In some embodiments, an isolated FN3 domain that binds CD71 comprises the amino acid sequence of SEQ ID NO: 36.

In some embodiments, an isolated FN3 domain that binds CD71 comprises the amino acid sequence of SEQ ID NO: 37.

In some embodiments, an isolated FN3 domain that binds CD71 comprises the amino acid sequence of SEQ ID NO: 38.

In some embodiments, an isolated FN3 domain that binds CD71 comprises the amino acid sequence of SEQ ID NO: 39.

In some embodiments, an isolated FN3 domain that binds CD71 comprises the amino acid sequence of SEQ ID NO: 40.

In some embodiments, an isolated FN3 domain that binds CD71 comprises the amino acid sequence of SEQ ID NO: 41.

In some embodiments, an isolated FN3 domain that binds CD71 comprises the amino acid sequence of SEQ ID NO: 42.

In some embodiments, an isolated FN3 domain that binds CD71 comprises the amino acid sequence of SEQ ID NO: 43.

In some embodiments, an isolated FN3 domain that binds CD71 comprises the amino acid sequence of SEQ ID NO: 44.

In some embodiments, an isolated FN3 domain that binds CD71 comprises the amino acid sequence of SEQ ID NO: 45.

In some embodiments, an isolated FN3 domain that binds CD71 comprises the amino acid sequence of SEQ ID NO: 46.

In some embodiments, an isolated FN3 domain that binds CD71 comprises the amino acid sequence of SEQ ID NO: 47.

In some embodiments, an isolated FN3 domain that binds CD71 comprises the amino acid sequence of SEQ ID NO: 48.

In some embodiments, an isolated FN3 domain that binds CD71 comprises the amino acid sequence of SEQ ID NO: 49.

In some embodiments, an isolated FN3 domain that binds CD71 comprises the amino acid sequence of SEQ ID NO: 50.

In some embodiments, an isolated FN3 domain that binds CD71 comprises the amino acid sequence of SEQ ID NO: 51.

In some embodiments, an isolated FN3 domain that binds CD71 comprises the amino acid sequence of SEQ ID NO: 52.

In some embodiments, an isolated FN3 domain that binds CD71 comprises the amino acid sequence of SEQ ID NO: 53.

In some embodiments, an isolated FN3 domain that binds CD71 comprises the amino acid sequence of SEQ ID NO: 54.

In some embodiments, an isolated FN3 domain that binds CD71 comprises the amino acid sequence of SEQ ID NO: 55.

In some embodiments, an isolated FN3 domain that binds CD71 comprises the amino acid sequence of SEQ ID NO: 56.

In some embodiments, an isolated FN3 domain that binds CD71 comprises the amino acid sequence of SEQ ID NO: 57.

In some embodiments, an isolated FN3 domain that binds CD71 comprises the amino acid sequence of SEQ ID NO: 58.

In some embodiments, an isolated FN3 domain that binds CD71 comprises the amino acid sequence of SEQ ID NO: 59.

In some embodiments, an isolated FN3 domain that binds CD71 comprises the amino acid sequence of SEQ ID NO: 60.

In some embodiments, an isolated FN3 domain that binds CD71 comprises the amino acid sequence of SEQ ID NO: 61.

In some embodiments, an isolated FN3 domain that binds CD71 comprises the amino acid sequence of SEQ ID NO: 62.

In some embodiments, an isolated FN3 domain that binds CD71 comprises the amino acid sequence of SEQ ID NO: 81. In some embodiments, an isolated FN3 domain that binds CD71 comprises the amino acid sequence of SEQ ID NO: 82. In some embodiments, an isolated FN3 domain that binds CD71 comprises the amino acid sequence of SEQ ID NO: 83. In some embodiments, an isolated FN3 domain that binds CD71 comprises the amino acid sequence of SEQ ID NO: 84. In some embodiments, an isolated FN3 domain that binds CD71 comprises the amino acid sequence of SEQ ID NO: 85. In some embodiments, an isolated FN3 domain that binds CD71 comprises the amino acid sequence of SEQ ID NO: 86. In some embodiments, an isolated FN3 domain that binds CD71 comprises the amino acid sequence of SEQ ID NO: 87. In some embodiments, an isolated FN3 domain that binds CD71 comprises the amino acid sequence of SEQ ID NO: 88. In some embodiments, an isolated FN3 domain that binds CD71 comprises the amino acid sequence of SEQ ID NO: 89. In some embodiments, an isolated FN3 domain that binds CD71 comprises the amino acid sequence of SEQ ID NO: 90. In some embodiments, an isolated FN3 domain that binds CD71 comprises the amino acid sequence of SEQ ID NO: 91. In some embodiments, an isolated FN3 domain that binds CD71 comprises the amino acid sequence of SEQ ID NO: 92. In some embodiments, an isolated FN3 domain that binds CD71 comprises the amino acid sequence of SEQ ID NO: 93. In some embodiments, an isolated FN3 domain that binds CD71 comprises the amino acid sequence of SEQ ID NO: 94. In some embodiments, an isolated FN3 domain that binds CD71 comprises the amino acid sequence of SEQ ID NO: 95. In some embodiments, an isolated FN3 domain that binds CD71 comprises the amino acid sequence of SEQ ID NO: 96. In some embodiments, an isolated FN3 domain that binds CD71 comprises the amino acid sequence of SEQ ID NO: 97. In some embodiments, an isolated FN3 domain that binds CD71 comprises the amino acid sequence of SEQ ID NO: 98. In some embodiments, an isolated FN3 domain that binds CD71 comprises the amino acid sequence of SEQ ID NO: 99. In some embodiments, an isolated FN3 domain that binds CD71 comprises the amino acid sequence of SEQ ID NO: 100. In some embodiments, an isolated FN3 domain that binds CD71 comprises the amino acid sequence of SEQ ID NO: 101. In some embodiments, an isolated FN3 domain that binds CD71 comprises the amino acid sequence of SEQ ID NO: 102. In some embodiments, an isolated FN3 domain that binds CD71 comprises the amino acid sequence of SEQ ID NO: 103. In some embodiments, an isolated FN3 domain that binds CD71 comprises the amino acid sequence of SEQ ID NO: 104. In some embodiments, an isolated FN3 domain that binds CD71 comprises the amino acid sequence of SEQ ID NO: 105. In some embodiments, an isolated FN3 domain that binds CD71 comprises the amino acid sequence of SEQ ID NO: 106. In some embodiments, an isolated FN3 domain that binds CD71 comprises the amino acid sequence of SEQ ID NO: 107. In some embodiments, an isolated FN3 domain that binds CD71 comprises the amino acid sequence of SEQ ID NO: 108. In some embodiments, an isolated FN3 domain that binds CD71 comprises the amino acid sequence of SEQ ID NO: 109. In some embodiments, an isolated FN3 domain that binds CD71 comprises the amino acid sequence of SEQ ID NO: 110. In some embodiments, an isolated FN3 domain that binds CD71 comprises the amino acid sequence of SEQ ID NO: 111. In some embodiments, an isolated FN3 domain that binds CD71 comprises the amino acid sequence of SEQ ID NO: 112. In some embodiments, an isolated FN3 domain that binds CD71 comprises the amino acid sequence of SEQ ID NO: 113. In some embodiments, an isolated FN3 domain that binds CD71 comprises the amino acid sequence of SEQ ID NO: 114. In some embodiments, an isolated FN3 domain that binds CD71 comprises the amino acid sequence of SEQ ID NO: 115. In some embodiments, an isolated FN3 domain that binds CD71 comprises the amino acid sequence of SEQ ID NO: 116. In some embodiments, an isolated FN3 domain that binds CD71 comprises the amino acid sequence of SEQ ID NO: 117. In some embodiments, an isolated FN3 domain that binds CD71 comprises the amino acid sequence of SEQ ID NO: 118. In some embodiments, an isolated FN3 domain that binds CD71 comprises the amino acid sequence of SEQ ID NO: 119. In some embodiments, an isolated FN3 domain that binds CD71 comprises the amino acid sequence of SEQ ID NO: 120. In some embodiments, an isolated FN3 domain that binds CD71 comprises the amino acid sequence of SEQ ID NO: 121. In some embodiments, an isolated FN3 domain that binds CD71 comprises the amino acid sequence of SEQ ID NO: 122. In some embodiments, an isolated FN3 domain that binds CD71 comprises the amino acid sequence of SEQ ID NO: 123. In some embodiments, an isolated FN3 domain that binds CD71 comprises the amino acid sequence of SEQ ID NO: 124. In some embodiments, an isolated FN3 domain that binds CD71 comprises the amino acid sequence of SEQ ID NO: 125. In some embodiments, an isolated FN3 domain that binds CD71 comprises the amino acid sequence of SEQ ID NO: 126. In some embodiments, an isolated FN3 domain that binds CD71 comprises the amino acid sequence of SEQ ID NO: 127. In some embodiments, an isolated FN3 domain that binds CD71 comprises the amino acid sequence of SEQ ID NO: 128. In some embodiments, an isolated FN3 domain that binds CD71 comprises the amino acid sequence of SEQ ID NO: 129. In some embodiments, an isolated FN3 domain that binds CD71 comprises the amino acid sequence of SEQ ID NO: 130. In some embodiments, an isolated FN3 domain that binds CD71 comprises the amino acid sequence of SEQ ID NO: 131. In some embodiments, an isolated FN3 domain that binds CD71 comprises the amino acid sequence of SEQ ID NO: 132. In some embodiments, an isolated FN3 domain that binds CD71 comprises the amino acid sequence of SEQ ID NO: 133. In some embodiments, an isolated FN3 domain that binds CD71 comprises the amino acid sequence of SEQ ID NO: 134. In some embodiments, an isolated FN3 domain that binds CD71 comprises the amino acid sequence of SEQ ID NO: 135. In some embodiments, an isolated FN3 domain that binds CD71 comprises the amino acid sequence of SEQ ID NO: 136. In some embodiments, an isolated FN3 domain that binds CD71 comprises the amino acid sequence of SEQ ID NO: 137. In some embodiments, an isolated FN3 domain that binds CD71 comprises the amino acid 30) sequence of SEQ ID NO: 138. In some embodiments, an isolated FN3 domain that binds CD71 comprises the amino acid sequence of SEQ ID NO: 139. In some embodiments, an isolated FN3 domain that binds CD71 comprises the amino acid sequence of SEQ ID NO: 140. In some embodiments, an isolated FN3 domain that binds CD71 comprises the amino acid sequence of SEQ ID NO: 141. In some embodiments, an isolated FN3 domain that binds CD71 comprises the amino acid sequence of SEQ ID NO: 142. In some embodiments, an isolated FN3 domain that binds CD71 comprises the amino acid sequence of SEQ ID NO: 143. In some embodiments, an isolated FN3 domain that binds CD71 comprises the amino acid sequence of SEQ ID NO: 144. In some embodiments, an isolated FN3 domain that binds CD71 comprises the amino acid sequence of SEQ ID NO: 145. In some embodiments, an isolated FN3 domain that binds CD71 comprises the amino acid sequence of SEQ ID NO: 146. In some embodiments, an isolated FN3 domain that binds CD71 comprises the amino acid sequence of SEQ ID NO: 147. In some embodiments, an isolated FN3 domain that binds CD71 comprises the amino acid sequence of SEQ ID NO: 148. In some embodiments, an isolated FN3 domain that binds CD71 comprises the amino acid sequence of SEQ ID NO: 149. In some embodiments, an isolated FN3 domain that binds CD71 comprises the amino acid sequence of SEQ ID NO: 150. In some embodiments, an isolated FN3 domain that binds CD71 comprises the amino acid sequence of SEQ ID NO: 151. In some embodiments, an isolated FN3 domain that binds CD71 comprises the amino acid sequence of SEQ ID NO: 152. In some embodiments, an isolated FN3 domain that binds CD71 comprises the amino acid sequence of SEQ ID NO: 153. In some embodiments, an isolated FN3 domain that binds CD71 comprises the amino acid sequence of SEQ ID NO: 154. In some embodiments, an isolated FN3 domain that binds CD71 comprises the amino acid sequence of SEQ ID NO: 155. In some embodiments, an isolated FN3 domain that binds CD71 comprises the amino acid sequence of SEQ ID NO: 156. In some embodiments, an isolated FN3 domain that binds CD71 comprises the amino acid sequence of SEQ ID NO: 157. In some embodiments, an isolated FN3 domain that binds CD71 comprises the amino acid sequence of SEQ ID NO: 158. In some embodiments, an isolated FN3 domain that binds CD71 comprises the amino acid sequence of SEQ ID NO: 159. In some embodiments, an isolated FN3 domain that binds CD71 comprises the amino acid sequence of SEQ ID NO: 160. In some embodiments, an isolated FN3 domain that binds CD71 comprises the amino acid sequence of SEQ ID NO: 161. In some embodiments, an isolated FN3 domain that binds CD71 comprises the amino acid sequence of SEQ ID NO: 162. In some embodiments, an isolated FN3 domain that binds CD71 comprises the amino acid sequence of SEQ ID NO: 163. In some embodiments, an isolated FN3 domain that binds CD71 comprises the amino acid sequence of SEQ ID NO: 164. In some embodiments, an isolated FN3 domain that binds CD71 comprises the amino acid sequence of SEQ ID NO: 165. In some embodiments, an isolated FN3 domain that binds CD71 comprises the amino acid sequence of SEQ ID NO: 166. In some embodiments, an isolated FN3 domain that binds CD71 comprises the amino acid sequence of SEQ ID NO: 167. In some embodiments, an isolated FN3 domain that binds CD71 comprises the amino acid sequence of SEQ ID NO: 168. In some embodiments, an isolated FN3 domain that binds CD71 comprises the amino acid sequence of SEQ ID NO: 169. In some embodiments, an isolated FN3 domain that binds CD71 comprises the amino acid sequence of SEQ ID NO: 170. In some embodiments, an isolated FN3 domain that binds CD71 comprises the amino acid sequence of SEQ ID NO: 171. In some embodiments, an isolated FN3 domain that binds CD71 comprises the amino acid sequence of SEQ ID NO: 172. In some embodiments, an isolated FN3 domain that binds CD71 comprises the amino acid sequence of SEQ ID NO: 173. In some embodiments, an isolated FN3 domain that binds CD71 comprises the amino acid sequence of SEQ ID NO: 174. In some embodiments, an isolated FN3 domain that binds CD71 comprises the amino acid sequence of SEQ ID NO: 175. In some embodiments, an isolated FN3 domain that binds CD71 comprises the amino acid sequence of SEQ ID NO: 176. In some embodiments, an isolated FN3 domain that binds CD71 comprises the amino acid sequence of SEQ ID NO: 177. In some embodiments, an isolated FN3 domain that binds CD71 comprises the amino acid sequence of SEQ ID NO: 178. In some embodiments, an isolated FN3 domain that binds CD71 comprises the amino acid sequence of SEQ ID NO: 179. In some embodiments, an isolated FN3 domain that binds CD71 comprises the amino acid sequence of SEQ ID NO: 180. In some embodiments, an isolated FN3 domain that binds CD71 comprises the amino acid sequence of SEQ ID NO: 181. In some embodiments, an isolated FN3 domain that binds CD71 comprises the amino acid sequence of SEQ ID NO: 182. In some embodiments, an isolated FN3 domain that binds CD71 comprises the amino acid sequence of SEQ ID NO: 183. In some embodiments, an isolated FN3 domain that binds CD71 comprises the amino acid sequence of SEQ ID NO: 184. In some embodiments, an isolated FN3 domain that binds CD71 comprises the amino acid sequence of SEQ ID NO: 30) 185. In some embodiments, an isolated FN3 domain that binds CD71 comprises the amino acid sequence of SEQ ID NO: 186. In some embodiments, an isolated FN3 domain that binds CD71 comprises the amino acid sequence of SEQ ID NO: 187. In some embodiments, an isolated FN3 domain that binds CD71 comprises the amino acid sequence of SEQ ID NO: 188. In some embodiments, an isolated FN3 domain that binds CD71 comprises the amino acid sequence of SEQ ID NO: 189. In some embodiments, an isolated FN3 domain that binds CD71 comprises the amino acid sequence of SEQ ID NO: 190. In some embodiments, an isolated FN3 domain that binds CD71 comprises the amino acid sequence of SEQ ID NO: 191. In some embodiments, an isolated FN3 domain that binds CD71 comprises the amino acid sequence of SEQ ID NO: 192. In some embodiments, an isolated FN3 domain that binds CD71 comprises the amino acid sequence of SEQ ID NO: 193. In some embodiments, an isolated FN3 domain that binds CD71 comprises the amino acid sequence of SEQ ID NO: 194. In some embodiments, an isolated FN3 domain that binds CD71 comprises the amino acid sequence of SEQ ID NO: 195. In some embodiments, an isolated FN3 domain that binds CD71 comprises the amino acid sequence of SEQ ID NO: 196. In some embodiments, an isolated FN3 domain that binds CD71 comprises the amino acid sequence of SEQ ID NO: 197. In some embodiments, an isolated FN3 domain that binds CD71 comprises the amino acid sequence of SEQ ID NO: 198. In some embodiments, an isolated FN3 domain that binds CD71 comprises the amino acid sequence of SEQ ID NO: 199. In some embodiments, an isolated FN3 domain that binds CD71 comprises the amino acid sequence of SEQ ID NO: 200. In some embodiments, an isolated FN3 domain that binds CD71 comprises the amino acid sequence of SEQ ID NO: 201. In some embodiments, an isolated FN3 domain that binds CD71 comprises the amino acid sequence of SEQ ID NO: 202. In some embodiments, an isolated FN3 domain that binds CD71 comprises the amino acid sequence of SEQ ID NO: 203. In some embodiments, an isolated FN3 domain that binds CD71 comprises the amino acid sequence of SEQ ID NO: 204. In some embodiments, an isolated FN3 domain that binds CD71 comprises the amino acid sequence of SEQ ID NO: 205. In some embodiments, an isolated FN3 domain that binds CD71 comprises the amino acid sequence of SEQ ID NO: 206. In some embodiments, an isolated FN3 domain that binds CD71 comprises the amino acid sequence of SEQ ID NO: 207. In some embodiments, an isolated FN3 domain that binds CD71 comprises the amino acid sequence of SEQ ID NO: 208. In some embodiments, an isolated FN3 domain that binds CD71 comprises the amino acid sequence of SEQ ID NO: 209. In some embodiments, an isolated FN3 domain that binds CD71 comprises the amino acid sequence of SEQ ID NO: 210. In some embodiments, an isolated FN3 domain that binds CD71 comprises the amino acid sequence of SEQ ID NO: 211. In some embodiments, an isolated FN3 domain that binds CD71 comprises the amino acid sequence of SEQ ID NO: 212. In some embodiments, an isolated FN3 domain that binds CD71 comprises the amino acid sequence of SEQ ID NO: 213. In some embodiments, an isolated FN3 domain that binds CD71 comprises the amino acid sequence of SEQ ID NO: 214. In some embodiments, an isolated FN3 domain that binds CD71 comprises the amino acid sequence of SEQ ID NO: 215. In some embodiments, an isolated FN3 domain that binds CD71 comprises the amino acid sequence of SEQ ID NO: 216. In some embodiments, an isolated FN3 domain that binds CD71 comprises the amino acid sequence of SEQ ID NO: 217. In some embodiments, an isolated FN3 domain that binds CD71 comprises the amino acid sequence of SEQ ID NO: 218. In some embodiments, an isolated FN3 domain that binds CD71 comprises the amino acid sequence of SEQ ID NO: 219. In some embodiments, an isolated FN3 domain that binds CD71 comprises the amino acid sequence of SEQ ID NO: 220. In some embodiments, an isolated FN3 domain that binds CD71 comprises the amino acid sequence of SEQ ID NO: 221. In some embodiments, an isolated FN3 domain that binds CD71 comprises the amino acid sequence of SEQ ID NO: 222. In some embodiments, an isolated FN3 domain that binds CD71 comprises the amino acid sequence of SEQ ID NO: 223. In some embodiments, an isolated FN3 domain that binds CD71 comprises the amino acid sequence of SEQ ID NO: 224. In some embodiments, an isolated FN3 domain that binds CD71 comprises the amino acid sequence of SEQ ID NO: 225. In some embodiments, an isolated FN3 domain that binds CD71 comprises the amino acid sequence of SEQ ID NO: 226. In some embodiments, an isolated FN3 domain that binds CD71 comprises the amino acid sequence of SEQ ID NO: 227. In some embodiments, an isolated FN3 domain that binds CD71 comprises the amino acid sequence of SEQ ID NO: 228. In some embodiments, an isolated FN3 domain that binds CD71 comprises the amino acid sequence of SEQ ID NO: 229. In some embodiments, an isolated FN3 domain that binds CD71 comprises the amino acid sequence of SEQ ID NO: 230. In some embodiments, an isolated FN3 domain that binds CD71 comprises the amino acid sequence of SEQ ID NO: 231. In some embodiments, an isolated FN3 domain that binds CD71 comprises the amino acid sequence of SEQ ID NO: 232. In some embodiments, an isolated FN3 domain that binds CD71 comprises the amino acid sequence of SEQ ID NO: 233. In some embodiments, an isolated FN3 domain that binds CD71 comprises the amino acid sequence of SEQ ID NO: 234. In some embodiments, an isolated FN3 domain that binds CD71 comprises the amino acid sequence of SEQ ID NO: 235. In some embodiments, an isolated FN3 domain that binds CD71 comprises the amino acid sequence of SEQ ID NO: 236. In some embodiments, an isolated FN3 domain that binds CD71 comprises the amino acid sequence of SEQ ID NO: 237. In some embodiments, an isolated FN3 domain that binds CD71 comprises the amino acid sequence of SEQ ID NO: 238. In some embodiments, an isolated FN3 domain that binds CD71 comprises the amino acid sequence of SEQ ID NO: 239. In some embodiments, an isolated FN3 domain that binds CD71 comprises the amino acid sequence of SEQ ID NO: 240). In some embodiments, an isolated FN3 domain that binds CD71 comprises the amino acid sequence of SEQ ID NO: 241. In some embodiments, an isolated FN3 domain that binds CD71 comprises the amino acid sequence of SEQ ID NO: 242. In some embodiments, an isolated FN3 domain that binds CD71 comprises the amino acid sequence of SEQ ID NO: 243. In some embodiments, an isolated FN3 domain that binds CD71 comprises the amino acid sequence of SEQ ID NO: 244. In some embodiments, an isolated FN3 domain that binds CD71 comprises the amino acid sequence of SEQ ID NO: 245. In some embodiments, an isolated FN3 domain that binds CD71 comprises the amino acid sequence of SEQ ID NO: 246. In some embodiments, an isolated FN3 domain that binds CD71 comprises the amino acid sequence of SEQ ID NO: 247. In some embodiments, an isolated FN3 domain that binds CD71 comprises the amino acid sequence of SEQ ID NO: 248. In some embodiments, an isolated FN3 domain that binds CD71 comprises the amino acid sequence of SEQ ID NO: 249. In some embodiments, an isolated FN3 domain that binds CD71 comprises the amino acid sequence of SEQ ID NO: 250. In some embodiments, an isolated FN3 domain that binds CD71 comprises the amino acid sequence of SEQ ID NO: 251. In some embodiments, an isolated FN3 domain that binds CD71 comprises the amino acid sequence of SEQ ID NO: 252. In some embodiments, an isolated FN3 domain that binds CD71 comprises the amino acid sequence of SEQ ID NO: 253. In some embodiments, an isolated FN3 domain that binds CD71 comprises the amino acid sequence of SEQ ID NO: 254. In some embodiments, an isolated FN3 domain that binds CD71 comprises the amino acid sequence of SEQ ID NO: 255. In some embodiments, an isolated FN3 domain that binds CD71 comprises the amino acid sequence of SEQ ID NO: 256. In some embodiments, an isolated FN3 domain that binds CD71 comprises the amino acid sequence of SEQ ID NO: 257. In some embodiments, an isolated FN3 domain that binds CD71 comprises the amino acid sequence of SEQ ID NO: 258. In some embodiments, an isolated FN3 domain that binds IPTS/128904106.1 20) CD71 comprises the amino acid sequence of SEQ ID NO: 259. In some embodiments, an isolated FN3 domain that binds CD71 comprises the amino acid sequence of SEQ ID NO: 260. In some embodiments, an isolated FN3 domain that binds CD71 comprises the amino acid sequence of SEQ ID NO: 261. In some embodiments, an isolated FN3 domain that binds CD71 comprises the amino acid sequence of SEQ ID NO: 262. In some embodiments, an isolated FN3 domain that binds CD71 comprises the amino acid sequence of SEQ ID NO: 263. In some embodiments, an isolated FN3 domain that binds CD71 comprises the amino acid sequence of SEQ ID NO: 264. In some embodiments, an isolated FN3 domain that binds CD71 comprises the amino acid sequence of SEQ ID NO: 265. In some embodiments, an isolated FN3 domain that binds CD71 comprises the amino acid sequence of SEQ ID NO: 266. In some embodiments, an isolated FN3 domain that binds CD71 comprises the amino acid sequence of SEQ ID NO: 267. In some embodiments, an isolated FN3 domain that binds CD71 comprises the amino acid sequence of SEQ ID NO: 268. In some embodiments, an isolated FN3 domain that binds CD71 comprises the amino acid sequence of SEQ ID NO: 269. In some embodiments, an isolated FN3 domain that binds CD71 comprises the amino acid sequence of SEQ ID NO: 270. In some embodiments, an isolated FN3 domain that binds CD71 comprises the amino acid sequence of SEQ ID NO: 271. In some embodiments, an isolated FN3 domain that binds CD71 comprises the amino acid sequence of SEQ ID NO: 272. In some embodiments, an isolated FN3 domain that binds CD71 comprises the amino acid sequence of SEQ ID NO: 273. In some embodiments, an isolated FN3 domain that binds CD71 comprises the amino acid sequence of SEQ ID NO: 274. In some embodiments, an isolated FN3 domain that binds CD71 comprises the amino acid sequence of SEQ ID NO: 275. In some embodiments, an isolated FN3 domain that binds CD71 comprises the amino acid sequence of SEQ ID NO: 276. In some embodiments, an isolated FN3 domain that binds CD71 comprises the amino acid sequence of SEQ ID NO: 277. In some embodiments, an isolated FN3 domain that binds CD71 comprises the amino acid sequence of SEQ ID NO: 278. In some embodiments, an isolated FN3 domain that binds CD71 comprises the amino acid sequence of SEQ ID NO: 279. In some embodiments, an 30) isolated FN3 domain that binds CD71 comprises the amino acid sequence of SEQ ID NO: 280. In some embodiments, an isolated FN3 domain that binds CD71 comprises the amino acid sequence of SEQ ID NO: 281. In some embodiments, an isolated FN3 domain that binds CD71 comprises the amino acid sequence of SEQ ID NO: 282. In some embodiments, an isolated FN3 domain that binds CD71 comprises the amino acid sequence of SEQ ID NO: 283. In some embodiments, an isolated FN3 domain that binds CD71 comprises the amino acid sequence of SEQ ID NO: 284. In some embodiments, an isolated FN3 domain that binds CD71 comprises the amino acid sequence of SEQ ID NO: 285. In some embodiments, an isolated FN3 domain that binds CD71 comprises the amino acid sequence of SEQ ID NO: 286. In some embodiments, an isolated FN3 domain that binds CD71 comprises the amino acid sequence of SEQ ID NO: 287. In some embodiments, an isolated FN3 domain that binds CD71 comprises the amino acid sequence of SEQ ID NO: 288. In some embodiments, an isolated FN3 domain that binds CD71 comprises the amino acid sequence of SEQ ID NO: 289. In some embodiments, an isolated FN3 domain that binds CD71 comprises the amino acid sequence of SEQ ID NO: 290. In some embodiments, an isolated FN3 domain that binds CD71 comprises the amino acid sequence of SEQ ID NO: 291. In some embodiments, an isolated FN3 domain that binds CD71 comprises the amino acid sequence of SEQ ID NO: 292. In some embodiments, an isolated FN3 domain that binds CD71 comprises the amino acid sequence of SEQ ID NO: 293. In some embodiments, an isolated FN3 domain that binds CD71 comprises the amino acid sequence of SEQ ID NO: 294. In some embodiments, an isolated FN3 domain that binds CD71 comprises the amino acid sequence of SEQ ID NO: 295. In some embodiments, an isolated FN3 domain that binds CD71 comprises the amino acid sequence of SEQ ID NO: 296. In some embodiments, an isolated FN3 domain that binds CD71 comprises the amino acid sequence of SEQ ID NO: 297. In some embodiments, an isolated FN3 domain that binds CD71 comprises the amino acid sequence of SEQ ID NO: 298. In some embodiments, an isolated FN3 domain that binds CD71 comprises the amino acid sequence of SEQ ID NO: 299. In some embodiments, an isolated FN3 domain that binds CD71 comprises the amino acid sequence of SEQ ID NO: 300. In some embodiments, an isolated FN3 domain that binds CD71 comprises the amino acid sequence of SEQ ID NO: 301. In some embodiments, an isolated FN3 domain that binds CD71 comprises the amino acid sequence of SEQ ID NO: 302. In some embodiments, an isolated FN3 domain that binds CD71 comprises the amino acid sequence of SEQ ID NO: 303. In some embodiments, an isolated FN3 domain that binds CD71 comprises the amino acid sequence of SEQ ID NO: 304. In some embodiments, an isolated FN3 domain that binds CD71 comprises the amino acid sequence of SEQ ID NO: 305. In some embodiments, an isolated FN3 domain that binds CD71 comprises the amino acid sequence of SEQ ID NO: 306. In some embodiments, an isolated FN3 domain that binds CD71 comprises the amino acid sequence of SEQ ID NO: 307. In some embodiments, an isolated FN3 domain that binds CD71 comprises the amino acid sequence of SEQ ID NO: 308. In some embodiments, an isolated FN3 domain that binds CD71 comprises the amino acid sequence of SEQ ID NO: 309.

In some embodiments, the FN3 domain binds to human CD71 at site on CD71 that does not compete with transferrin binding to CD71. In some embodiments, the FN3 domain comprises a sequence of SEQ ID NO: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149.

In some embodiments, the isolated FN3 domain that binds CD71 comprises an initiator methionine (Met) linked to the N-terminus of the molecule.

In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 33-50. In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 51-61 or 62. In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 81-309. In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149.

Percent identity can be determined using the default parameters to align two sequences using BlastP available through the NCBI website.

Conjugates of the FN3 Domains that Bind CD71 of the Disclosure

In some embodiments, an isolated FN3 domain that binds CD71 conjugated to a heterologous molecule(s) is provided.

In some embodiments, the FN3 domain is conjugated to an oligonucleotide. For example, the oligonucleotide can be used for inhibiting the expression of a gene or mRNA transcript. The oligonucleotide can be a siRNA, miRNA, antisense oligonucleotide, and the like.

In some embodiments, the peptide is conjugated to a lipid nanoparticle, which can be used, for example, for cell-specific targeting.

In some embodiments, the protein is conjugated to a binding moiety that targets CD71 or another protein for protein degradation. For example, the protein can be conjugated to a PROTACS (binding moieties for an E3 ubiquitin ligase) and thus deliver the protein to the E3 ligase. These can linked through a linker, such as a glycine-serine linker and the like.

The FN3 domain that binds to CD71 can also be conjugated or linked to another FN3 domain that binds to a different target, other than CD71. This would enable the peptide to be multi-specific (e.g. bi-specific, tri-specific, etc.,), such that it binds to CD71 and another, for example, protein. In some embodiments, the CD71 FN3 binding domain is linked to another FN3 domain that binds to an antigen expressed by a tumor cell (tumor antigen).

In some embodiments, FN3 domains can be linked together by a linker to form a bivalent FN3 domain. The linker can be a flexible linker. In some embodiments, the linker is a G/S linker. In some embodiments the linker has 1, 2, 3, or 4 G/S repeats. A G/S repeat unit is four glycines followed by a serine, e.g. GGGGS (SEQ ID NO: 310). In some embodiments, the heterologous molecule is a detectable label or a therapeutic agent, such as, but not limited to a cytotoxic agent.

In some embodiments, an FN3 domain that binds CD71 conjugated to a detectable label is provided. Non-limiting examples of detectable labels are provided for herein.

In some embodiments, an FN3 domain that binds CD71 conjugated to a therapeutic agent is provided. Non-limiting examples of therapeutic agents, such as, but not limited to, cytotoxic agents, are provided for herein.

The FN3 domains that bind CD71 conjugated to a detectable label can be used to evaluate expression of CD71 on samples such as tumor tissue in vivo or in vitro.

Detectable labels include compositions that when conjugated to the FN3 domains that bind CD71 renders CD71 detectable, via spectroscopic, photochemical, biochemical, immunochemical, or other chemical methods.

Exemplary detectable labels include, but are not limited to, radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, cintillants, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In some embodiments, the detectable label emits a signal as a result of being stimulated by an external stimulus, such as a magnetic or electric, or electromagnetic field.

Exemplary radioactive isotopes may be $\gamma$-emitting, Auger-emitting, $\beta$-emitting, an alpha-emitting or positron-emitting radioactive isotope. Exemplary radioactive isotopes include $^3$H, $^{11}$C, $^{13}$C, $^{15}$N, $^{18}$F, $^{19}$F, $^{55}$Co, $^{57}$Co, $^{60}$Co, $^{61}$Cu, $^{62}$Cu, $^{64}$Cu, $^{67}$Cu, $^{68}$Ga, $^{72}$As, $^{75}$Br, $^{86}$Y, $^{89}$Zr, $^{90}$Sr, $^{94}$mTc, $^{99}$mTc, $^{115}$In, $^{123}$I, $^{124}$I, $^{125}$I, $^{131}$I, $^{211}$At, $^{212}$Bi, $^{213}$Bi, $^{223}$Ra, $^{226}$Ra, $^{225}$Ac and $^{227}$Ac.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, *neptunium* atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e., iodine) to 83 (i.e., bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, Cut, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5 (6)-carboxyfluorescein, IRDye 680RD maleimide or IRDye 800CW, ruthenium polypyridyl dyes, and the like.

Suitable fluorophores are fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The FN3 domains that specifically bind CD71 conjugated to a detectable label may be used, for example, as an imaging agent to evaluate tumor distribution, diagnosis for the presence of tumor cells and/or, recurrence of tumor.

In some embodiments, the FN3 domains that specifically bind CD71 are conjugated to a therapeutic agent, such as, but not limited to, a cytotoxic agent.

In some embodiments, the therapeutic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The FN3 domains that bind CD71 conjugated to a therapeutic agent disclosed herein may be used in the targeted delivery of the therapeutic agent to CD71 expressing cells (e.g. tumor cells), and intracellular accumulation therein. Although not bound to any particular theory, this type of delivery can be helpful where systemic administration of these unconjugated agents may result in unacceptable levels of toxicity to normal cells.

In some embodiments, the therapeutic agent can elicit their cytotoxic and/or cytostatic effects by mechanisms such as, but not limited to, tubulin binding, DNA binding, topoisomerase inhibition, DNA cross linking, chelation, spliceosome inhibition, NAMPT inhibition, and HDAC inhibition.

In some embodiments, the therapeutic agent is a spliceosome inhibitor, a NAMPT inhibitor, or a HDAC inhibitor. In some embodiments, the agent is an immune system agonist, for example, TLR7,8,9, RIG-I (dsRNA), and STING (CpG) agonists. In some embodiments, the agent is daunomycin, doxorubicin, methotrexate, vindesine, bacterial toxins such as diphtheria toxin, ricin, geldanamycin, maytansinoids or calicheamicin.

In some embodiments, the therapeutic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, or the tricothecenes. In some embodiments, the therapeutic agent is a radionuclide, such as 212Bi, $^{131}$I, $^{131}$In, $^{90}$Y, or $^{186}$Re.

In some embodiments, the therapeutic agent is dolastatin or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45 (12): 3580-3584) and have anticancerand antifungal activity. The dolastatin or auristatin drug moiety may be attached to the FN3 domain through the N (amino) terminus or the C (carboxyl) terminus of the peptidic drug moiety (WO 02/088172), or via any cysteine engineered into the FN3 domain.

In some embodiments, therapeutic agent can be, for example, auristatins, camptothecins, duocarmycins, etoposides, maytansines and maytansinoids, taxanes, benzodiazepines or benzodiazepine containing drugs (e.g., pyrrolo[1, 41-benzodiazepines (PBDs), indolinobenzodiazepines, and oxazolidinobenzodiazepines) or *vinca* alkaloids.

The FN3 domains that specifically bind CD71 may be conjugated to a detectable label using known methods.

In some embodiments, the detectable label is complexed with a chelating agent.

In some embodiments, the detectable label is conjugated to the FN3 domain that binds CD71 via a linker.

The detectable label, therapeutic compound, or the cytotoxic compound may be linked directly, or indirectly, to the FN3 domain that binds CD71 using known methods. Suitable linkers are known in the art and include, for example, prosthetic groups, non-phenolic linkers (derivatives of N-succimidyl-benzoates: dodecaborate), chelating moieties of both macrocyclics and acyclic chelators, such as derivatives of 1,4,7,10-tetraazacyclododecane-1,4,7,10, tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis(p-diazoniumbenzoyl)ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

In some embodiment, the FN3 domain that binds CD71 is removed from the blood via renal clearance.

Isolation of CD71 Binding FN3 Domains from a Library Based on Tencon Sequence

Tencon (SEQ ID NO: 1) is a non-naturally occurring fibronectin type III (FN3) domain designed from a consensus sequence of fifteen FN3 domains from human tenascin-C(Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992: U.S. Pat. No. 6,673,901). These loops, or selected residues within each loop, may be randomized in order to construct libraries of fibronectin type III (FN3) domains that may be used to select novel molecules that bind CD71. Table I shows positions and sequences of each loop and beta-strand in Tencon (SEQ ID NO: 1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in U.S. Pat. Publ. No. 2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 4) having substitutions E11R, L17A, N46V and E86I when compared to Tencon of SEQ ID NO: 1.

TABLE 1

| Tencon topology | |
| --- | --- |
| FN3 domain | Tencon (SEQ ID NO: 1) |
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http://www_sloning_com). This technology uses a library of premade double stranded triplets that act as universal building blocks sufficient for thousands of gene synthesis processes. The triplet library represents all possible sequence combinations necessary to build any desired DNA molecule. The codon designations are according to the well-known IUB code.

The FN3 domains that specifically bind CD71 may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476: Odegrip et al., Proc Natl Acad Sci USA 101, 2806-2810, 2004), and assaying the library for specific binding to PSMA by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains that specifically bind CD71 are further characterized for their binding to CD71, modulation of CD71 activity, internalization, stability, and other desired characteristics.

The FN3 domains that specifically bind CD71 may be generated using any FN3 domain as a template to generate a library and screening the library for molecules specifically binding CD71 using methods provided within. Exemplar FN3 domains that may be used are the 3rd FN3 domain of tenascin C (TN3), Fibcon, and the 10th FN3 domain of fibronectin (FN10). Accordingly, PCT applications WO 2010/051274, WO 2011/137319, and WO 2013/049275 are incorporated herein in their entirety. Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak. Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144: Int. Pat. Publ. No. WO2009/085462: U.S. Pat. No. 6,969,108: U.S. Pat. Nos. 6,172,197; 5,223,409; 6,582,915; 6,472,147).

In some embodiments, the FN3 domain that binds CD71 is based on Tencon sequence of SEQ ID NO: 1 or Tencon27 sequence of SEQ ID NO: 4, the SEQ ID NO: 1 or the SEQ ID NO: 4, optionally having substitutions at residues positions 11, 14, 17, 37, 46, 73, and/or 86.

In some embodiments, the FN3 protein or polypeptide is one that binds to human CD71 at a site on CD71 that does not compete with transferrin binding to CD71. As used herein, a site on CD71 that does not compete with transferrin binding to CD71 refers to an epitope or part of CD71 where the binding of the FN3 protein does not compete or inhibit the binding of transferrin to CD71. The competition, or lack thereof, can be complete or partial. In some embodiments, the binding also does not inhibit the internalization of transferrin into the cell through its interaction with CD71.

In some embodiments, methods for identifying a FN3 protein that binds to CD71 at a site that does not compete or inhibit transferrin binding to CD71 are provided. In some embodiments, the methods comprise contacting CD71 in the presence of transferrin or an agent that binds to the CD71 transferrin binding site with a test FN3 protein; and identifying a test FN3 protein that binds to CD71 in the presence of transferrin or an agent that binds to the CD71 transferrin binding site. In some embodiments, the method comprises isolating the test FN3 protein that binds to CD71 in the presence of transferrin or an agent that binds to the CD71 transferrin binding site. In some embodiments, the methods comprise sequencing the test FN3 protein that binds to CD71 in the presence of transferrin or an agent that binds to the CD71 transferrin binding site. In some embodiments, the methods comprise preparing or obtaining a nucleic acid sequence encoding the test FN3 protein that binds to CD71 in the presence of transferrin or an agent that binds to the CD71 transferrin binding site. In some embodiments, the methods comprise expressing the test FN3 protein that binds to CD71 in the presence of transferrin or an agent that binds to the CD71 transferrin binding site from a nucleic acid sequence encoding the test FN3 protein that binds to CD71 in the presence of transferrin or an agent that binds to the CD71 transferrin binding site. In some embodiments, the test FN3 protein is expressed in a cell. In some embodiments, the methods comprise isolating and/or purifying the expressed test FN3 protein.

In some embodiments a FN3 protein is provided, wherein the FN3 protein is identified according to any method provided herein.

The FN3 domains that specifically bind CD71 may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr. Opin. Biotechnol., 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues may be incorporated to the FN3 domain containing molecules disclosed herein.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("Tm") temperature, the temperature in ° Celsius (° C.) at which half of the molecules become unfolded, using standard methods. Typically, the higher the Tm, the more stable the molecule. In addition to heat, the chemical environment also changes the ability of the protein to maintain a particular three dimensional structure.

In some embodiments, the FN3 domain that binds CD71 may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the Tm.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride): reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phospholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domain that binds CD71 may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO: 63), $(GGGS)_2$ (SEQ ID NO: 64), $(GGGGS)_5$ (SEQ ID NO: 65), $(AP)_2$ (SEQ ID NO: 66), $(AP)_5$ (SEQ ID NO: 67), $(AP)_{10}$ (SEQ ID NO: 68), $(AP)_{20}$ (SEQ ID NO: 69) and A (EAAAK); AAA (SEQ ID NO: 70). The dimers and multimers may be linked to each other in a N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Half-Life Extending Moieties

The FN3 domains that specifically bind CD71 may incorporate other subunits for example via covalent interaction. In some embodiments, the FN3 domains that specifically bind CD71 further comprise a half-life extending moiety. Exemplary half-life extending moieties are albumin, albumin variants, albumin-binding proteins and/or domains, transferrin and fragments and analogues thereof, and Fc regions. Amino acid sequences of the human Fc regions are well known, and include IgG1, IgG2, IgG3, IgG4, IgM, IgA and IgE Fc regions. In some embodiments, the FN3 domains that specifically bind CD71 may incorporate a second FN3 domain that binds to a molecule that extends the half-life of the entire molecule, such as, but not limited to, any of the half-life extending moieties described herein. In some embodiments, the second FN3 domain binds to albumin, albumin variants, albumin-binding proteins and/or domains, and fragments and analogues thereof.

All or a portion of an antibody constant region may be attached to the FN3 domain that binds CD71 to impart antibody-like properties, especially those properties associated with the Fc region, such as Fc effector functions such as Clq binding, complement dependent cytotoxicity (CDC), Fc receptor binding, antibody-dependent cell-mediated cytotoxicity (ADCC), phagocytosis, down regulation of cell surface receptors (e.g., B cell receptor: BCR), and may be further modified by modifying residues in the Fc responsible for these activities (for review: see Strohl, *Curr Opin Biotechnol.* 20, 685-691, 2009).

Additional moieties may be incorporated into the FN3 domains that specifically bind CD71 such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules disclosed herein.

A pegyl moiety may for example be added to the FN3 domain that binds CD71 by incorporating a cysteine residue to the C-terminus of the molecule, or engineering cysteines into residue positions that face away from the CD71 binding face of the molecule, and attaching a pegyl group to the cysteine using well known methods.

FN3 domains that specifically bind CD71 incorporating additional moieties may be compared for functionality by several well-known assays. For example, altered properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules disclosed herein in in vivo models.

Polynucleotides, Vectors, Host Cells

In some embodiments, nucleic acids encoding the FN3 domains specifically binding CD71 as isolated polynucle-otides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof are provided. Certain exemplary polynucleotides are disclosed herein, however, other poly-nucleotides which, given the degeneracy of the genetic code or codon preferences in a given expression system, encode the FN3 domains disclosed herein are also within the scope of the disclosure.

In some embodiments, an isolated polynucleotide encodes the FN3 domain specifically binding CD71 comprising the amino acid sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309.

The polynucleotides disclosed herein may be produced by chemical synthesis such as solid phase polynucleotide syn-thesis on an automated polynucleotide synthesizer and assembled into complete single or double stranded mol-ecules. Alternatively, the polynucleotides disclosed herein may be produced by other techniques such as PCR followed by routine cloning. Techniques for producing or obtaining polynucleotides of a given known sequence are well known in the art.

The polynucleotides disclosed herein may comprise at least one non-coding sequence, such as a promoter or enhancer sequence, intron, polyadenylation signal, a cis sequence facilitating RepA binding, and the like. The poly-nucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

In some embodiments, a vector comprising at least one polynucleotide disclosed herein is provided. Such vectors may be plasmid vectors, viral vectors, vectors for baculo-virus expression, transposon based vectors or any other vector suitable for introduction of the polynucleotides dis-closed herein into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

In some embodiments, a host cell comprising the vector is provided. The FN3 domain that specifically bind CD71 may be optionally produced by a cell line, a mixed cell line, an immortalized cell or clonal population of immortalized cells, as well known in the art. See, e.g., Ausubel, et al . . . ed., Current Protocols in Molecular Biology, John Wiley & Sons, Inc., NY, NY (1987-2001); Sambrook, et al., Molecu-lar Cloning: A Laboratory Manual, 2nd Edition, Cold Spring Harbor, NY (1989): Harlow and Lane, Antibodies, a Labo-ratory Manual, Cold Spring Harbor, NY (1989): Colligan, et al . . . eds., Current Protocols in Immunology, John Wiley & Sons, Inc., NY (1994-2001): Colligan et al., Current Proto-cols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21 (DE3), BL21-GOLD (DE3), XL1-Blue, JM109, HMS174, HMS174 (DE3), and any of the natural or engineered *E. coli* spp. *Klebsiella* spp., or *Pseudomonas* spp strains.

In some embodiments, a method of producing the isolated FN3 domain that binds CD71, comprising culturing the isolated host cell under conditions such that the isolated FN3 domain that binds CD71 is expressed, and purifying the FN3 domain.

The FN3 domains that bind CD71 may be purified from recombinant cell cultures by well-known methods, for example by protein A purification, ammonium sulfate or ethanol precipitation, acid extraction, anion or cation exchange chromatography, phosphocellulose chromatogra-phy, hydrophobic interaction chromatography, affinity chro-matography, hydroxyapatite chromatography and lectin chromatography, or high performance liquid chromatogra-phy (HPLC).

Anti-Idiotypic Antibodies

In some embodiments, an anti-idiotypic antibody binds to the FN3 domain.

In some embodiments, an anti-idiotypic antibody that binds the FN3 domain comprises the amino acid sequences of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309.

Kits

In some embodiments, a kit comprising the FN3 domain that binds CD71 is provided.

The kit may be used for therapeutic uses and as a diagnostic kit.

In some embodiments, the kit comprises the FN3 domain that binds CD71 and reagents for detecting the FN3 domain. In some embodiments, the kit comprises a bivalent FN3 domain. The kit can include one or more other elements including: instructions for use: other reagents, e.g., a label, an agent useful for chelating, or otherwise coupling, a radioprotective composition; devices or other materials for preparing the FN3 domain that binds CD71 for administration for imaging, diagnostic or therapeutic purpose: pharmaceutically acceptable carriers; and devices or other materials for administration to a subject.

In some embodiments, the kit comprises the FN3 domain that binds CD71 comprising the amino acid sequences of one of SEQ ID NOs: 33-50.

In some embodiments, the kit comprises the FN3 domain that binds CD71 comprising the amino acid sequences of one of SEQ ID NOs: 51-61.

In some embodiments, the kit comprises the FN3 domain that binds CD71 comprising the amino acid sequences of one of SEQ ID NOs: 81-309.

In some embodiments, the kit comprises the FN3 domain that binds CD71 comprising the amino acid sequences of one of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149.

Uses of CD71 Binding FN3 Domains

The FN3 domains that specifically bind CD71 or conjugates thereof may be used to diagnose, monitor, modulate, treat, alleviate, help prevent the incidence of, or reduce the symptoms of human disease or specific pathologies in cells, tissues, organs, fluid, or, generally, a host.

In some embodiments, the FN3 domains that specifically bind CD71 or conjugates thereof may also be used in imaging CD71 positive tumor tissue in a subject. The methods disclosed herein may be used with an animal patient belonging to any classification. Examples of such animals include mammals such as humans, rodents, dogs, cats and farm animals.

In some embodiments, a method of diagnosing a subject having, or who is likely to develop cancer of a tissue based on the expression of CD71 by cells of the cancer tissue, methods of predicting success of immunotherapy, methods of prognosis, and methods of treatment are provided.

In some embodiments, a method of detecting CD71-expressing cancer cells in a tumor tissue is provided, the method comprising: obtaining a sample of the tumor tissue from a subject: detecting whether CD71 is expressed in the tumor tissue by contacting toe sample of the tumor tissues with the FN3 domain that binds CD71 comprising the amino acid sequence of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309, and detecting the binding between CD71 and the FN3 domain.

In some embodiments, the CD71 cell is a cell involved in a CNS diseases, inflammatory/immune diseases, such as MS & infectious diseases of the brain.

In some embodiments, the tissue can be tissue of any organ or anatomical system, that expresses CD71.

In some embodiments, CD71 expression may be evaluated using known methods, such as immunohistochemistry or ELISA.

In some embodiments, a method of isolating CD71 expressing cells is provided, the method comprising: obtaining a sample from a subject: contacting the sample with the FN3 domain that binds CD71 comprising the amino acid sequence of one of SEQ ID NOs: 33-50, and isolating the cells bound to the FN3 domains.

In some embodiments, a method of isolating CD71 expressing cells is provided, the method comprising: obtaining a sample from a subject: contacting the sample with the FN3 domain that binds CD71 comprising the amino acid sequence of one of SEQ ID NOs: 51-61, and isolating the cells bound to the FN3 domains.

In some embodiments, a method of detecting CD71-expressing cancer cells in a tumor tissue is provided, the method comprising: conjugating the FN3 domain that binds CD71 comprising the amino acid sequence of one of SEQ ID NOs: 33-50 to a detectable label to form a conjugate: administering the conjugate to a subject; and visualizing the CD71 expressing cancer cells to which the conjugate is bound.

In some embodiments, a method of detecting CD71-expressing cancer cells in a tumor tissue is provided, the method comprising: conjugating the FN3 domain that binds CD71 comprising the amino acid sequence of one of SEQ ID NOs: 51-62 or 81-309 to a detectable label to form a conjugate: administering the conjugate to a subject; and visualizing the CD71 expressing cancer cells to which the conjugate is bound.

In some embodiments, a method of treating a subject having cancer is provided, the method comprising administering to the subject a FN3 domain that binds CD71. In some embodiments, the FN3 domain is conjugated to a therapeutic agent (e.g. cytotoxic agent, an oligonucleotide, a FN3 domain that binds to another target, and the like). In some embodiments, the subject has a solid tumor.

In some embodiments, the solid tumor is a melanoma.

In some embodiments, the solid tumor is a lung cancer. In some embodiments, the solid tumor is a non-small cell lung cancer (NSCLC). In some embodiments, the solid tumor is a squamous non-small cell lung cancer (NSCLC). In some embodiments, the solid tumor is a non-squamous NSCLC. In some embodiments, the solid tumor is a lung adenocarcinoma.

In some embodiments, the solid tumor is a renal cell carcinoma (RCC).

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer. In some embodiments, the solid tumor is castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the subject has a hematological malignancy.

In some embodiments, the hematological malignancy is a lymphoma, a myeloma or a leukemia. In some embodiments, the hematological malignancy is a B cell lymphoma. In some embodiments, the hematological malignancy is Burkitt's lymphoma. In some embodiments, the hematological malignancy is Hodgkin's lymphoma. In some embodiments, the hematological malignancy is a non-Hodgkin's lymphoma.

In some embodiments, the hematological malignancy is a myelodysplastic syndrome.

In some embodiments, the hematological malignancy is an acute myeloid leukemia (AML). In some embodiments, the hematological malignancy is a chronic myeloid leukemia (CML). In some embodiments, the hematological malignancy is a chronic myelomoncytic leukemia (CMML).

In some embodiments, the hematological malignancy is a multiple myeloma (MM).

In some embodiments, the hematological malignancy is a plasmacytoma.

In some embodiments, the compositions or pharmaceutical compositions provided herein may be administered alone or in combination with other therapeutics, that is, simultaneously or sequentially. In some embodiments, the other or additional therapeutics are other anti-tumor agent or therapeutics. Different tumor types and stages of tumors can require the use of various auxiliary compounds useful for treatment of cancer. For example, the compositions provided herein can be used in combination with various chemotherapeutics such as taxol, tyrosine kinase inhibitors, leucovorin, fluorouracil, irinotecan, phosphatase inhibitors, MEK inhibitors, among others. The composition may also be used in combination with drugs which modulate the immune response to the tumor such as anti-PD-1 or anti-CTLA-4, among others. Additional treatments can be agents that modulate the immune system, such antibodies that target PD-1 or PD-L1.

In some embodiments, the FN3 domains that specifically bind CD71 or conjugates thereof that may be used to diagnose, monitor, modulate, treat, alleviate, help prevent the incidence of, or reduce the symptoms of human disease or specific pathologies in cells, tissues, organs, fluid, or, generally, a host, also exhibit the property of being able to cross the blood brain barrier. The blood-brain barrier (BBB) prevents most macromolecules (e.g., DNA, RNA, and polypeptides) and many small molecules from entering the brain. The BBB is principally composed of specialized endothelial cells with highly restrictive tight junctions, consequently, passage of substances, small and large, from the blood into the central nervous system is controlled by the BBB. This structure makes treatment and management of patients with neurological diseases and disorders (e.g., brain cancer) difficult as many therapeutic agents cannot be delivered across the BBB with desirable efficiency. Additional conditions that involve disruptions of the BBB include: stroke, diabetes, seizures, hypertensive encephalopathy, acquired immunodeficiency syndrome, traumatic brain injuries, multiple sclerosis, Parkinson's disease (PD) and Alzheimer disease. This ability is especially useful for treating brain cancers including for example: astrocytoma, medulloblastoma, glioma, ependymoma, germinoma (pinealoma), glioblastoma multiform, oligodendroglioma, schwannoma, retinoblastoma, and congenital tumors: or a cancer of the spinal cord, e.g., neurofibroma, meningioma, glioma, and sarcoma. In certain embodiments, the FN3 domains that specifically bind CD71 comprising the amino acid sequence of one of SEQ ID NOs: 33-50 or conjugates thereof, are useful to deliver a therapeutic or cytotoxic agent, for example, across the blood brain barrier. In certain embodiments, the FN3 domains that specifically bind CD71 comprising the amino acid sequence of one of SEQ ID NOs: 51-61 or conjugates thereof, are useful to deliver a therapeutic or cytotoxic agent, for example, across the blood brain barrier. In some embodiments, the protein comprises a sequence of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, 149, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309.

In some embodiments, the polypeptide that can facilitates the transport of a therapeutic across the BBB is a protein comprising a sequence of SEQ ID NO: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149.

"Treat" or "treatment" refers to the therapeutic treatment and prophylactic measures, wherein the object is to prevent or slow down (lessen) an undesired physiological change or disorder, such as the development or spread of cancer. In some embodiments, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the FN3 domains that specifically bind CD71 may vary according to factors such as the disease state, age, sex, and weight of the individual. Exemplary indicators of an effective FN3 domain that binds CD71 is improved well-being of the patient, decrease or shrinkage of the size of a tumor, arrested or slowed growth of a tumor, and/or absence of metastasis of cancer cells to other locations in the body.

Administration/Pharmaceutical Compositions

In some embodiments, pharmaceutical compositions of the FN3 domains that specifically bind CD71, optionally conjugated to a detectable label, therapeutic, or a cytotoxic agent disclosed herein and a pharmaceutically acceptable carrier, are provided. For therapeutic use, the FN3 domains that specifically bind CD71 may be prepared as pharmaceutical compositions containing an effective amount of the domain or molecule as an active ingredient in a pharmaceutically acceptable carrier. "Carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules disclosed herein in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21st Edition, Troy, D. B. ed., Lipincott Williams and Wilkins, Philadelphia, PA 2006, Part 5, Pharmaceutical Manufacturing pp 691-1092, See especially pp. 958-989.

The mode of administration for therapeutic use of the FN3 domains disclosed herein may be any suitable route that delivers the agent to the host, such as parenteral administration, e.g., intradermal, intramuscular, intraperitoneal, intravenous or subcutaneous, pulmonary: transmucosal (oral, intranasal, intravaginal, rectal), using a formulation in a tablet, capsule, solution, powder, gel, particle; and contained in a syringe, an implanted device, osmotic pump, cartridge, micropump: or other means appreciated by the skilled artisan, as well known in the art. Site specific administration may be achieved by for example intra-articular, intrabronchial, intra-abdominal, intracapsular, intracartilaginous, intracavitary, intracelial, intracerebellar, intracerebroventricular, intracolic, intracervical, intragastric, intrahepatic, intracardial, intraosteal, intrapelvic, intraperi-cardial, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

Examples

The following examples are illustrative of the embodiments disclosed herein. These examples are provided for the purpose of illustration only and the embodiments should in no way be construed as being limited to these examples, but rather should be construed to encompass any and all variations which become evidence as a result of the teaching provided herein. Those of skill in the art will readily recognize a variety of non-critical parameters that could be changed or modified to yield essentially similar results.

EXAMPLE 1. Construction of Tencon Libraries with Randomized Loops

Tencon (SEQ ID NO: 1) is an immunoglobulin-like scaffold, fibronectin type III (FN3) domain, designed from a consensus sequence of fifteen FN3 domains from human tenascin-C(Jacobs et al., Protein Engineering, Design, and Selection, 25: 107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

Tencon:

```
                                        (SEQ ID NO 1)
LPAPKNLVVSEVTEDSLRLSWTAPDAAFDSFLIQYQESEKVGEAINLTV

PGSERSYDLTGLKPGTEYTVSIYGVKGGHRSNPLSAEFTT
```

Various libraries were generated using the Tencon scaffold and various design strategies. In general, libraries TCL 1 and TCL2 produced good binders. Generation of TCL1 and TCL2 libraries are described in detail in Int. Pat. Publ. No. WO/2014081944A2.

Construction of TCL1 Library

A library designed to randomize only the FG loop of Tencon (SEQ ID NO: 1), TCL1, was constructed for use with the cis-display system (Jacobs et al., Protein Engineering, Design, and Selection, 25:107-117, 2012). In this system, a single-strand DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves: the 5' fragment contains the promoter and Tencon sequences, while the 3' fragment contains the repA gene and the cis-and ori elements. These two halves are combined by restriction digest in order to produce the entire construct. The TCL1 library was designed to incorporate random amino acids only in the FG loop of Tencon. NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

```
TCL1 library
                                      (SEQ ID NO: 2)
LPAPKNLVVSEVTEDSLRLSWTAPDAAFDSFLIQYQESEKVGEAI

NLTVPGSERSYDLTGLKPGTEYTVSIYGVX7-12PLSAEFTT;
``` wherein $X_1$, $X_2$, $X_3$, $X_4$, $X_5$, $X_6$, $X_7$ is any amino acid; and $X_8$, $X_9$, $X_{10}$, $X_{11}$ and $X_{12}$ are any amino acid or deleted Construction of TCL2 Library TCL2 library was constructed in which both the BC and the FG loops of Tencon were randomized and the distribution of amino acids at each position was strictly controlled. Table 2 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008: Olson et al., Protein Sci 16:476-84, 2007). Towards this goal, the "designed distribution" in Table 2 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

```
TCL2 library
                                    (SEQ ID NO: 3)
LPAPKNLVVSEVTEDSLRLSWX₁X₂X₃X₄X₅X₆X₇X₈SFLIQYQES

EKVGEAINLTVPGSERSYDLTGLKPGTEYTVSIYGVX₉X₁₀X₁₁X₁₂

X₁₃SX₁₄X₁₅LSAEFTT;
``` wherein $X_1$ is Ala, Arg, Asn, Asp, Glu, Gln, Gly, His, Ile, Leu, Lys, Phe, Pro, Ser, Thr, Trp, Tyr or Val;

$X_2$ is Ala, Arg, Asn, Asp, Glu, Gln, Gly, His, Ile, Leu, Lys, Phe, Pro, Ser, Thr, Trp, Tyr or Val;

$X_3$ Ala, Arg, Asn, Asp, Glu, Gln, Gly, His, Ile, Leu, Lys, Phe, Pro, Ser, Thr, Trp, Tyr or Val;

$X_4$ is Ala, Arg, Asn, Asp, Glu, Gln, Gly, His, Ile, Leu, Lys, Phe, Pro, Ser, Thr, Trp, Tyr or Val;

$X_5$ is Ala, Arg, Asn, Asp, Glu, Gln, Gly, His, Ile, Leu, Lys, Phe, Pro, Ser, Thr, Trp, Tyr or Val;

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val; and $X_{15}$ is Ala, Arg, Asn, Asp, Glu, Gln, Gly, His, Ile, Leu, Lys, Phe, Pro, Ser, Thr, Trp, Tyr or Val.

TABLE 2

| Residue distribution in the TCL2 library | | |
|---|---|---|
| Residue Position* | WT residues | Distribution in the TCL2 library |
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO: 4) when compared to the wild type tencon as well as altering of the positions randomized in the BC and FG loops. Tencon27 is described in Int. Pat. Appl. No. WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc. Natl. Acad. Sci. USA 101:2806-2810, 2004). The details of this design are shown below:

```
Stabilized Tencon (Tencon27)
                                    (SEQ ID NO: 4)
LPAPKNLVVSRVTEDSARLSWTAPDAAFDSFLIQYQESEKVGEAIVL

TVPGSERSYDLTGLKPGTEYTVSIYGVKGGHRSNPLSAIFTT

TCL7 (randomized FG and BC loops)
                                    (SEQ ID NO: 5)
LPAPKNLVVSRVTEDSARLSWX₁X₂X₃X₄X₅X₆X₇X₈X₉FDSFLIQY

QESEKVGEAIVLTVPGSERSYDLTGLKPGTEYTVSIYGVX₁₀X₁₁X₁₂

X₁₃X₁₄X₁₅X₁₆X₁₇X₁₈X₁₉SNPLSAIFTT;
``` wherein $X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ is A, D, E, F, G, H, I, K, L, N, P, Q, R, S, T, V, W or Y; and $X_7$, $X_8$, $X_9$, $X_{17}$, $X_{18}$ and $X_{19}$, is A, D, E, F, G, H, I, K, L, N, P, Q, R, S, T, V, W, Y or deleted.

```
TCL9 (randomized FG loop)
                                    (SEQ ID NO: 6)
LPAPKNLVVSRVTEDSARLSWTAPDAAFDSFLIQYQESEKVGEAIVL

TVPGSERSYDLTGLKPGTEYTVSIYGV X₁X₂X₃X₄X₅X₆X₇X₈X₉

X₁₀X₁₁X₁₂SNPLSAIFTT;
X₁, X₂, X₃, X₄, X₅, X₆ and X₇, is A, D, E, F,
G, H, I, K, L, N, P, Q, R, S, T, V, W or Y;
and X₈, X₉, X₁₀, X₁₁ and X₁₂ is A, D, E, F, G,
H, I, K, L, N, P, Q, R, S, T, V, W, Y
or deleted.
```

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31) For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO: 9) and Sloning-Rev (SEQ ID NO: 10).

The 3' fragment of the library is a constant DNA sequence containing elements for display, including a PspOMI restriction site, the coding region of the repA gene, and the cis-and ori elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 ug) of 3' repA DNA in the presence of NotI and PspOMI enzyme and T4 ligase at 37° C. overnight. The ligated library product was amplified by using 12 cycles of PCR with oligos POP2250 (SEQ ID NO: 11) and DigLigRev (SEQ ID NO: 12). For each sub-library, the resulting DNA from 12 PCR reactions were combined and purified by Qiagen spin column. The yield for each sub-library of TCL9 ranged from 32-34 ug.

Construction of FG/BC Loop Libraries (TCL7)

The TCL7 library provides for a library with randomized Tencon BC and FG loops. In this library, BC loops of lengths 6-9 amino acids were mixed combinatorically with randomized FG loops of 7-12 amino acids in length. Synthetic Tencon fragments BC6, BC7, BC8, and BC9 (SEQ ID NOs: 13-16, respectively) were produced to include the Tencon gene encoding for the N-terminal portion of the protein up to and including residue VX such that the BC loop is replaced with either 6, 7, 8, or 9 randomized amino acids, which are represented by the string of "N" in the sequences provided for herein. These fragments were synthesized prior to the discovery of L17A, N46V and E83I mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide encoding for amino acid A17 (130mer-L17A, SEQ ID NO: 17) was produced by PCR using oligos POP2222ext (SEQ ID NO: 18) and LS1114 (SEQ ID NO: 19). This was done to include the L17A mutation in the library (CEN5243). Next, DNA fragments encoding for Tencon residues R18-V75 including randomized BC loops were amplified by PCR using BC6, BC7, BC8, or BC9 as a templates and oligos LS1115 (SEQ ID NO: 20) and LS1117 (SEQ ID NO: 21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen PCR purification kit. The purified DNA was digested with BsaI-HF and gel purified.

Fragments encoding the FG loop were amplified by PCR using FG7, FG8, FG9, FG10, FG11, and FG12 as templates with oligonucleotides SDG10 (SEQ ID NO: 22) and SDG24 (SEQ ID NO: 23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID NO: 24) and SDG28 SEQ ID NO: 25). 7.5 ug of each reaction product were then digested with NotI and cleaned up with a Qiagen PCR purification column. 5.2 ug of this DNA, was ligated to an equal molar amount of RepA DNA fragment (~14 ug) digested with PspOMI and the product amplified by PCR using oligos POP2222.

EXAMPLE 2: Generation of Tencon Libraries Having Alternative Binding Surfaces The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc. Natl. Acad. Sci. USA 104:6632-6637, 2007). In contrast, an ankyrin repeat scaffold protein that was selected to bind to MBP was found to have a much more planar interaction surface and to bind to the outer surface of MBP distant from the active (Binz et al., Nat. Biotechnol. 22:575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein.

Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO: 7), was designed into Tencon27 scaffold (SEQ ID NO: 4).

A full description of the methods used to construct this library is described in US. Pat. Publ. No. 2013/0226834.

```
TCL14 library
(SEQ ID NO: 7):
LPAPKNLVVSRVTEDSARLSWTAPDAAFDSFX₁IX₂YX₃EX₄X₅X₆X₇

GEAIVLTVPGSERSYDLTGLKPGTEYX₈VX₉IX₁₀GVKGGX₁₁X₁₂

SX₁₃PLSAIFTT;
``` wherein $X_1$, $X_2$, $X_3$, $X_4$, $X_5$, $X_6$, $X_7$, $X_8$, $X_9$, $X_{10}$, $X_{11}$, $X_{12}$ and $X_{13}$ are A, D, E, F, G, H, I, K, L, N, P, Q, R, S, T, V, W, Y, C or M.

The two beta strands forming the C-CD-F-FG surface in Tencon27 have a total of 9 surface exposed residues that could be randomized; C-strand: S30, L32, Q34, Q36; F-strand; E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 3). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J. Mol. Biol. 377:1518-1528, 2008) as described in Table 3. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and 186 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 3.

```
TCL24 Library
                            (SEQ ID NO: 8)
LPAPKNLVVSRVTEDSARLSWTAPDAAFDSFX₁IX₂YX₃EX₄X₅X₆X₇

GEAIX₈LX₉VPGSERSYDLTGLKPGTEYX₁₀VX₁₁IX₁₂GVKGGX₁₃

X₁₄SX₁₅PLX₁₆AX₁₇FTT;
``` wherein $X_1$, $X_2$, $X_3$, $X_4$, $X_5$, $X_6$, $X_{10}$, $X_{11}$, $X_{12}$, $X_{13}$, $X_{14}$, $X_{15}$, $X_{16}$ and $X_{17}$ are A, D, E, F, G, H, I, K, L, N, P, Q, R, S, T, V, Y or W.

TABLE 3

| Amino acid frequency (%) at each randomized position for TCL21, TCL23, and TCL24. | | | |
|---|---|---|---|
| Amino Acid | TCL19 | TCL21 | TCL23 | TCL24 |
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., Proc. Natl. Acad. Sci. USA 101:2806-2810, 2004) as described above for the loop libraries.

EXAMPLE 3: Selection of Fibronectin Type III (FN3) Domains that Bind CD71 Panning and Biochemical Screening FN3 domains specific for human CD71 were selected via CIS-Display (Odegrip et al 2004) using recombinant biotinylated CD71 extracellular domain (Sino Biologics) with an N-terminal 6His tag. For in vitro transcription and translation (ITT), 3 µg of DNA from FN3 domain libraries TCL18, TCL19, TCL21, TCL23, and TCL24 were used, with unbound library members removed by washing. DNA was eluted from the target protein by heating and amplified by PCR using KOD polymerase for further rounds of panning. High affinity binders were isolated by successively lowering the concentration of target CD71 during each round from 400 nM to 100 nM and increasing the washing stringency. Outputs from the fifth round panning were subjected to four additional rounds of off-rate selection. The biotinylated target antigen concentration was reduced from 25 nM in rounds 6 and 7 to 2.5 nM in rounds 8 and 9.

Following panning, genes encoding the selected FN3 domains were amplified by PCR, subcloned into a pET vector modified to include a ligase independent cloning site, and transformed into BL21 (DE3) (Stratagene) cells for soluble expression in *E. coli* using standard molecular biology techniques. A gene sequence encoding a C-terminal poly-histidine tag was added to each FN3 domain to enable purification and detection.

To screen for FN3 domains that specifically bind CD71, streptavidin-coated Maxisorp plates (Nunc catalog 436110) were blocked for 1 hour in Starting Block T20 (Pierce) and then coated with biotinylated CD71 (using same antigen as in panning) or negative controls (an unrelated Fc-fused recombinant protein and human serum albumin) for 1 hour. Plates were rinsed with TBST and diluted lysate was applied to plates for 1 hour. Following additional rinses, wells were treated with HRP-conjugated anti-V5 tag antibody (Abcam, ab1325), for 1 hour and then assayed with POD (Roche, 11582950001). The DNA from FN3 domain lysates with signals at least 10-fold ELISA signal above that of streptavidin controls were sequenced resulting in 23 unique, readable FN3 domain sequences isolated from Round 9 screening (Table 4).

TABLE 4

| Summary of Screening Hits | | | |
|---|---|---|---|
| hCD71 | HSA | huCD71/Fc | SEQ ID |
| 517840 | 11120 | 46.6 | 33 |
| 310480 | 25920 | 12.0 | 34 |
| 3244640 | 1520 | 2134.6 | 35 |
| 3297120 | 6160 | 535.2 | 36 |
| 1271360 | 2720 | 467.4 | 37 |
| 840480 | 4160 | 202.0 | 38 |
| 506800 | 4160 | 121.8 | 39 |
| 220240 | 2960 | 74.4 | 40 |
| 4267840 | 10080 | 423.4 | 41 |
| 2827520 | 5920 | 477.6 | 42 |
| 1621680 | 8160 | 198.7 | 43 |
| 175760 | 3920 | 44.8 | 44 |
| 1926160 | 2880 | 668.8 | 45 |
| 112560 | 3040 | 37.0 | 46 |
| 264800 | 5200 | 50.9 | 47 |
| 943120 | 2800 | 336.8 | 48 |
| 10915200 | 11520 | 947.5 | 49 |
| 10786240 | 2400 | 4494.3 | 50 |
| 9709680 | 4240 | 2290.0 | 51 |
| 10112800 | 1760 | 5745.9 | 52 |
| 1007840 | 9120 | 110.5 | 53 |
| 6987520 | 6160 | 1134.3 | 54 |
| 11142160 | 7760 | 1435.8 | 55 |
| 11339360 | 7520 | 1507.9 | 56 |
| 1903600 | 16880 | 112.8 | 57 |
| 301680 | 4800 | 62.9 | 58 |
| 1946880 | 3200 | 608.4 | 59 |
| 4479040 | 6480 | 691.21 | 60 |
| 4900320 | 10640 | 460.56 | 61 |

Size Exclusion Chromatography Analysis

Size exclusion chromatography was used to determine the aggregation state of anti-CD71 FN3 domains. Aliquots (10 µL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. Tencon protein was included in each run as a control. Agilent ChemStation software was used to analyze the elution profiles. Selected SEC parameters for the 18 identified FN3 domains are listed in Table 5.

TABLE 5

| Summary of Size Exclusion Chromatography Analysis | | | |
|---|---|---|---|
| SEQ ID | RT (min) | Height (mAU) | Y/N |
| 33 | 5.616 | 21578 | Y |
| 34 | 5.729 | 19210 | Y |
| 35 | 5.818 | 36983 | Y |
| 36 | 6.008 | 59654 | Y |
| 37 | 5.486 | 33495 | Y |
| 38 | 5.608 | 32759 | Y |
| 39 | 6.508 | 40533 | Y |
| 40 | 6.043 | 42995 | Y |
| 41 | 6.535 | 12055 | N |
| 42 | 6.243 | 114847 | Y |
| 43 | 6.736 | 64318 | Y |
| 44 | 6.389 | 33849 | Y |
| 45 | 6.196 | 16535 | Y |
| 46 | 5.962 | 56696 | Y |
| 47 | 6.799 | 61095 | Y |
| 48 | 5.405 | 24438 | Y |
| 49 | 6.149 | 118941 | Y |
| 50 | 6.496 | 122793 | Y |
| 51 | 7.729 | 17618 | N |
| 52 | 6.316 | 87040 | Y |
| 53 | 6.118 | 87022 | Y |
| 54 | 5.972 | 34366 | Y |
| 55 | 6.06 | 35099 | Y |
| 56 | 5.496 | 28177 | Y |
| 57 | 6.175 | 13973 | Y |
| 58 | 5.862 | 45603 | Y |
| 59 | 5.589 | 85517 | Y |
| 60 | 5.671 | 8.6 | Y |
| 61 | 5.752 | 8.9 | Y |

High-throughput Expression and Conjugation

Clones identified were grown in duplicate 5 mL cultures in 24 well deep block plates. Briefly, 5 mL/well of TB media supplemented with 50 µg/mL Kanamycin was seeded with 150 µL of overnight culture and grown for about 3 hours at 37° C., with shaking at 220 rpm (OD600 ~1). Cultures were induced with IPTG to a final concentration of 1 mM for an additional 4 hours at 37° C., 220 rpm. Bacterial pellets were recovered by centrifugation at 2250×g for 15 minutes. 600 µL/well BugBuster HT (Novagen) supplemented with lysozyme (Sigma) at 0.2 mg/mL was added to each well; pellets were dissociated by pipette and then shaken vigorously on a platform shake for about 30 minutes until pellets were lysed. Plates were spun at 2250×g for 15 minutes to clarify lysates and the 2 600-uL aliquots for each sample were combined. His-tagged FN3 domains were purified on His Trap plates (GE) according to the manufacturer's instructions followed by buffer exchange into TBS using Zeba Spin 7K desalt plates (Thermo Scientific). Protein concentrations were assessed by Nanodrop. For conjugation to GlyGly-VC-MMAF, FN3 domain (30 µM) was mixed with 150 µM Gly GlyVC-MMAF (Concortis) and 1 µM Sortase A in a total volume of 200 µL. Conjugations were allowed to proceed for 1.5 hours at room temperature and purified again using a 96 well His Multitrap HP plate from GE Healthcare according to the manufacturer's instructions. Buffer exchange into PBS was achieved using Zeba desalt plates followed by sterile filtering using Multiscreen HTS GV plates (Durapore) with centrifugation at 3000×g for 2 mins. Concentrations were assessed by Nanodrop.

Identification of SK-BR3 Binding FN3 Domains

SK-BR-3 cells are cultured in McCoy's 5a Medium+10% Fetal Bovine Serum. FN3 dilutions are prepared in FACS buffer. 50,000 SK-BR-3 cells are added to each well: media was aspirated after centrifugation and cells are resuspended in 100 μL of FACS buffer containing HiLyte labeled FN3 domains. Cells are incubated for 2 hours at 37° C., 5% CO2. Cells are rinsed 3× with FACS buffer and finally resuspended in 100 μL of FACS buffer. Fluorescence is detected by Intellictye. Cell populations are identified by the FSC-SSC dot plot followed by recording of the FL4 MFI. Data are normalized to the average of 8 unstained cells and dose response curves are fit using GraphPad.

Binding of Selected Clones by Dose-Response ELISA

Selected clones are analyzed by ELISA to determine EC50 values for binding. Briefly, Maxisorb plates are coated with streptavidin at 5 μg/ml overnight at 4C. Plates were then blocked with StartingBlock (ThermoFisher) at room temperature for 1 hour and then washed with TBS-Tween. Biotinylated CD71 (2 μg/ml) was captured onto the streptavidin plates and serially diluted Centyrins were added to appropriate wells for 1 hour at room temperature. After washing, bound Centyrin was detected with anti-V5 tag antibody, which is conjugated to HRP and POD substrate and a luminescence plate reader. Luminescence values are plotted as a function of concentration and fit to a dose response using PRISM to determine EC50 values for binding.

Identification of internalizing FN3 domains via toxin conjugates. The FN3 domains were conjugated to the cytotoxic tubulin inhibitor momomethyl auristatin F (MMAF) via an enzyme-cleavable Val-Cit linker or a non-cleavable PEG4 linker (VC-MMAF) using the methodology described for the NEM conjugation. Cell killing was assessed by measuring viability of the SKBR-3 cells following exposure to the cysteine variant-cytotoxin conjugates. Cells are plated in white-well, opaque bottomed, tissue culture-treated plates (Fisher, PI15042) at 3000/well in 50 μL/well of phenol red RPMI media (Gibco, 11875093) with 10% fetal bovine serum (Gibco). Cells are allowed to attach overnight at 37° C. in a humidified 5% CO2 atmosphere. Cells are treated with 25 μL of fresh media and 25 μL of 4× inhibitor made up in fresh media. Cell viability is determined by an endpoint assay with Cell TiterGlo (Promega) at 72 hours. IC50 values are determined by fitting data to the equation for a sigmoidal dose response with variable slope using GraphPad Prism (GraphPad Software). The results are illustrated in Table 6 and demonstrate that the FN3 domains that bind to CD71 were internalized and cytotoxic.

TABLE 6

IC50 of CD71 FN3- MMAF conjugate molecules in SKBR-3 Cells

| SEQ ID | IC50 (nM) |
|---|---|
| 33 | 3.27 |
| 34 | 0.37 |
| 35 | 2.5 |
| 36 | 7.1 |
| 37 | 0.15 |

TABLE 6-continued

IC50 of CD71 FN3- MMAF conjugate molecules in SKBR-3 Cells

| SEQ ID | IC50 (nM) |
|---|---|
| 38 | 3.82 |
| 39 | 0.52 |
| 40 | 3 |
| 41 | 4.7 |
| 42 | 0.19 |
| 43 | 0.069 |
| 44 | 2.5 |
| 45 | 8.3 |
| 46 | 2.69 |
| 47 | 5.9 |
| 48 | 0.42 |
| 49 | 3 |
| 50 | 3.1 |
| 51 | 4.9 |
| 52 | 6.3 |
| 53 | 0.07 |
| 54 | 0.4 |
| 55 | 0.026 |
| 56 | 0.24 |
| 57 | 3.13 |
| 58 | 7.7 |
| 59 | 4 |
| 60 | 0.45 |
| 61 | 1.93 |

Bivalent FN3 Protein

A bivalent FN3 protein is produced using two FN3 domains connected by a 4 repeat G/S linker. The bivalent FN3 protein is conjugated to VC-MMAF as described and assessed for cytotoxicity in SK-BR3 cells. The IC50 value for bivalent molecule is found to be better.

Competition for Transferrin Binding and Internalization

FN3 domain VCMMAF conjugates were screened for competition with human transferrin using the cytotoxicity assay described above. FN3 domains were screened in the absence or presence of 0.6 μM holo-human transferrin (T0665-100 MG). The IC50 values for FN3 domain toxin conjugates on SK-BR3 cells screened in the absence or presence of competitor are shown in Table 7.

TABLE 7

IC50 of CD71 FN3 domain - MMAF conjugate molecules on SKBR-3 cells +/− human transferrin

| SEQ ID | IC50 (nM) | |
|---|---|---|
| | huTf competitor | no competitor |
| 33 | ~200 | 4.4 |
| 34 | 195.9 | 1.3 |
| 35 | 41.5 | 0.7 |
| 37 | 142.8 | 0.7 |
| 38 | ~120 | 4 |
| 39 | 31.1 | 1.2 |
| 40 | ~100 | 2.2 |
| 41 | 0.5 | 0.01 |
| 42 | ~70 | 2.4 |
| 43 | ~80 | 0.97 |
| 45 | 0.9 | 0.05 |
| 46 | ~100 | 3 |
| 47 | ~85 | 1.6 |
| 48 | ~70 | 1.3 |
| 53 | ~90 | 3.6 |
| 54 | 5 | 0.13 |
| 55 | 5.5 | 0.15 |
| 56 | 14.7 | 0.35 |
| 57 | 5.3 | 0.38 |

TABLE 7-continued

| IC50 of CD71 FN3 domain - MMAF conjugate molecules on SKBR-3 cells +/- human transferrin | | |
|---|---|---|
| | IC50 (nM) | |
| SEQ ID | huTf competitor | no competitor |
| 60 | 14.4 | 0.21 |
| 62 | 0.60 | >0.005 |

```
SEQ ID NO: 1 = Original Tencon Sequence
LPAPKNLVVSEVTEDSLRLSWTAPDAAFDSFLIQYQESEKVGEAIN

LTVPGSERSYDLTGLKPGTEYTVSIYGVKGGHRSNPLSAEFTT

SEQ ID NO: 2 = TCL1 library
LPAPKNLVVSEVTEDSLRLSWTAPDAAFDSFLIQYQESEKVGEAINL

TVPGSERSYDLTGLKPGTEYTVSIYGV(X)7-12PLSAEFTT;
``` wherein
$X_1$, $X_2$, $X_3$, $X_4$, $X_5$, $X_6$, $X_7$ is any amino acid; and
$X_8$, $X_9$, $X_{10}$, $X_{11}$ and $X_{12}$ are any amino acid or deleted

```
SEQ ID NO: 3 = TCL2 library
LPAPKNLVVSEVTEDSLRLSWX1X2X3X4X5X6X7X8SFLIQYQESEK

VGEAINLTVPGSERSYDLTGLKPGTEYTVSIYGVX9X10X11X12X13

SX14X15LSAEFTT;
``` wherein
$X_1$ is Ala, Arg, Asn, Asp, Glu, Gln, Gly, His, Ile, Leu, Lys, Phe, Pro, Ser, Thr, Trp, Tyr or Val;
$X_2$ is Ala, Arg, Asn, Asp, Glu, Gln, Gly, His, Ile, Leu, Lys, Phe, Pro, Ser, Thr, Trp, Tyr or Val;
$X_3$ Ala, Arg, Asn, Asp, Glu, Gln, Gly, His, Ile, Leu, Lys, Phe, Pro, Ser, Thr, Trp, Tyr or Val;
$X_4$ is Ala, Arg, Asn, Asp, Glu, Gln, Gly, His, Ile, Leu, Lys, Phe, Pro, Ser, Thr, Trp, Tyr or Val;
$X_5$ is Ala, Arg, Asn, Asp, Glu, Gln, Gly, His, Ile, Leu, Lys, Phe, Pro, Ser, Thr, Trp, Tyr or Val;
$X_6$ is Ala, Arg, Asn, Asp, Glu, Gln, Gly, His, Ile, Leu, Lys, Phe, Pro, Ser, Thr, Trp, Tyr or Val;
$X_7$ is Phe, Ile, Leu, Val or Tyr;
$X_8$ is Asp, Glu or Thr;
$X_9$ is Ala, Arg, Asn, Asp, Glu, Gln, Gly, His, Ile, Leu, Lys, Phe, Pro, Ser, Thr, Trp, Tyr or Val;
$X_{10}$ is Ala, Arg, Asn, Asp, Glu, Gln, Gly, His, Ile, Leu, Lys, Phe, Pro, Ser, Thr, Trp, Tyr or Val;
$X_{11}$ is Ala, Arg, Asn, Asp, Glu, Gln, Gly, His, Ile, Leu, Lys, Phe, Pro, Ser, Thr, Trp, Tyr or Val;
$X_{12}$ is Ala, Arg, Asn, Asp, Glu, Gln, Gly, His, Ile, Leu, Lys, Phe, Pro, Ser, Thr, Trp, Tyr or Val;
$X_{13}$ is Ala, Arg, Asn, Asp, Glu, Gln, Gly, His, Ile, Leu, Lys, Phe, Pro, Ser, Thr, Trp, Tyr or Val;
$X_{14}$ is Ala, Arg, Asn, Asp, Glu, Gln, Gly, His, Ile, Leu, Lys, Phe, Pro, Ser, Thr, Trp, Tyr or Val; and
$X_{15}$ is Ala, Arg, Asn, Asp, Glu, Gln, Gly, His, Ile, Leu, Lys, Phe, Pro, Ser, Thr, Trp, Tyr or Val.

```
SEQ ID NO: 4 = Stabilized Tencon
LPAPKNLVVSRVTEDSARLSWTAPDAAFDSFLIQYQESEKVGEAIV

LTVPGSERSYDLTGLKPGTEYTVSIYGVKGGHRSNPLSAIFTT
```

-continued

```
SEQ ID NO: 5 = TCL7 (FG and BC loops)
LPAPKNLVVSRVTEDSARLSWX1X2X3X4X5X6X7X8X9FDSFLIQYQE

SEKVGEAIVLTVPGSERSYDLTGLKPGTEYTVSIYGVX10X11X12X13

X14X15X16X17X18X19SNPLSAIFTT;
``` wherein
$X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ are A, D, E, F, G, H, I, K, L, N, P, Q, R, S, T, V, W or Y; and
$X_1$, $X_8$, $X_9$, $X_{17}$, $X_{18}$ and $X_{19}$, are A, D, E, F, G, H, I, K, L, N, P, Q, R, S, T, V, W, Y or deleted

```
SEQ ID NO: 6 = TCL9 (FG loop)
LPAPKNLVVSRVTEDSARLSWTAPDAAFDSFLIQYQESEKVGEAIVL

TVPGSERSYDLTGLKPGTEYTVSIYGVX1X2X3X4X5X6X7X8X9X10X11

X12SNPLSAIFTT;
``` wherein
$X_1$, $X_2$, $X_3$, $X_4$, $X_5$, $X_6$ and $X_7$, is A, D, E, F, G, H, I, K, L, N, P, Q, R, S, T, V, W or Y; and
$X_8$, $X_9$, $X_{10}$, $X_{11}$ and $X_{12}$ is A, D, E, F, G, H, I, K, L, N, P, Q, R, S, T, V, W, Y or deleted.

```
TCL14 library
                                      (SEQ ID NO: 7)
LPAPKNLVVSRVTEDSARLSWTAPDAAFDSFX1IX2YX3EX4X5X6X7

GEAIVLTVPGSERSYDLTGLKPGTEYX8VX9IX10GVKGGX11X12S

X13PLSAIFTT;
``` wherein
$X_1$, $X_2$, $X_3$, $X_4$, $X_5$, $X_6$, $X_7$, $X_8$, $X_9$, $X_{10}$, $X_{11}$, $X_{12}$ and $X_{13}$ are A, D, E, F, G, H, I, K, L, N, P, Q, R, S, T, V, W, Y, C or M.

```
TCL24 Library
                                      (SEQ ID NO: 8)
LPAPKNLVVSRVTEDSARLSWTAPDAAFDSFX1IX2YX3EX4X5X6X7

GEAIX8LX9VPGSERSYDLTGLKPGTEYX10VX11IX12GVKGGX13

X14SX15PLX16AX17FTT;
``` wherein
$X_1$, $X_2$, $X_3$, $X_4$, $X_5$, $X_6$, $X_{10}$, $X_{11}$, $X_{12}$, $X_{13}$, $X_{14}$, $X_{15}$, $X_{16}$ and $X_{17}$ are A, D, E, F, G, H, I, K, L, N, P, Q, R, S, T, V, Y or W.

```
SEQ ID NO: 9 = Sloning-FOR
GTGACACGGCGGTTAGAAC

SEQ ID NO: 10 = Sloning-REV
GCCTTTGGGAAGCTTCTAAG

SEQ ID NO: 11 = POP2250
CGGCGGTTAGAACGCGGCTACAATTAATAC

SEQ ID NO: 12 = DigLigRev
CATGATTACGCCAAGCTCAGAA

SEQ ID NO: 13 = BC9
GTGACACGGCGGTTAGAACGCGGCTACAATTAATACATAACCCCAT

CCCCCTGTTGACAATTAATCATCGGCTCGTATAATGTGTGGAATTG
```

-continued           -continued

TGAGCGGATAACAATTTCACACAGGAAACAGGATCTACCATGCTGC

CGGCGCCGAAAAACCTGGTTGTTTCTGAAGTTACCGAAGACTCTCT

GCGTCTGTCTTGGNNNNNNNNNNNNNNNNNNNNNNNNNNNNTTYGAC

TCTTTCCTGATCCAGTACCAGGAATCTGAAAAAGTTGGTGAAGCGA

TCAACCTGACCGTTCCGGGTTCTGAACGTTCTTACGACCTGACCGG

TCTGAAACCGGGTACCGAATACACCGTTTCTATCTACGGTGTTCT

TAGAAGCTTCCCAAAGGC
(wherein N is any base)

SEQ ID NO: 14 = BC8
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTGAAGTTACCGAAGACTCTCT

GCGTCTGTCTTGGNNNNNNNNNNNNNNNNNNNNNNNNNNNNTTYGACTCT

TTCCTGATCCAGTACCAGGAATCTGAAAAAGTTGGTGAAGCGATCA

ACCTGACCGTTCCGGGTTCTGAACGTTCTTACGACCTGACCGGTCT

GAAACCGGGTACCGAATACACCGTTTCTATCTACGGTGTTCTTAG

AAGCTTCCCAAAGGC
(wherein N is any base)

SEQ ID NO: 15 = BC7
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTGAAGTTACCGAAGACTCTCT

GCGTCTGTCTTGGNNNNNNNNNNNNNNNNNNNNNNNNNNNNTTYGACTCTTTC

CTGATCCAGTACCAGGAATCTGAAAAAGTTGGTGAAGCGATCAACC

TGACCGTTCCGGGTTCTGAACGTTCTTACGACCTGACCGGTCTGAA

ACCGGGTACCGAATACACCGTTTCTATCTACGGTGTTCTTAGAAGC

TTCCCAAAGGC
(wherein N is any base)

SEQ ID NO: 16 = BC6
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTGAAGTTACCGAAGACTCTCT

GCGTCTGTCTTGGNNNNNNNNNNNNNNNNNNNNNNNTTYGACTCTTTCCTG

ATCCAGTACCAGGAATCTGAAAAAGTTGGTGAAGCGATCAACCTGA

CCGTTCCGGGTTCTGAACGTTCTTACGACCTGACCGGTCTGAAACC

GGGTACCGAATACACCGTTTCTATCTACGGTGTTCTTAGAAGCTTC

CCAAAGGC
(wherein N is any base)

SEQ ID NO: 17 = 130mer-L17A
CGGCGGTTAGAACGCGGCTACAATTAATACATAACCCCATCCCCCT

GTTGACAATTAATCATCGGCTCGTATAATGTGTGGAATTGTGAGCG

GATAACAATTTCACACAGGAAACAGGATCTACCATGCTG

SEQ ID NO: 18 = POP222ext
CGG CGG TTA GAA CGC GGC TAC AAT TAA TAC

SEQ ID NO: 19 = LS1114
CCA AGA CAG ACG GGC AGA GTC TTC GGT AAC GCG

AGA AAC   AAC CAG GTT TTT CGG CGC CGG CAG CAT

GGT AGA TCC TGT TTC

SEQ ID NO: 20 = LS1115
CCG AAG ACT CTG CCC GTC TGT CTT GG

SEQ ID NO: 21 = LS1117
CAG TGG TCT CAC GGA TTC CTG GTA CTG GAT CAG

GAA AGA GT GAA

SEQ ID NO: 22 = SDG10
CATGCGGTCTCTTCCGAAAAAGTTGGTGAAGCGATCGTCCTGACCG

TTCCGGGT

SEQ ID NO: 23 = SDG24
GGTGGTGAAGATCGCAGACAGCGGGTTAG

SEQ ID NO: 24 = POP2222
CGGCGGTTAGAACGCGGCTAC

SEQ ID NO: 25 = SDG28
AAGATCAGTTGCGGCCGCTAGACTAGAACCGCTGCCACCGCCGGTG

GTGAAGATCGCAGAC

SEQ ID NO: 26 = FG12
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNNNNNNNNNNNNTCTAACCCGCTGTCTGCGATCT

TCACCACCGGCGGTCACCATCACCATCACCATGGCAGCGGTTCTAG

TCTAGCGGCCGCAACTGATCTTGGC
(wherein N is any base)

SEQ ID NO: 27 = FG11
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNNNNNNNNNNNTCTAACCCGCTGTCTGCGATCTTCA

CCACCGGCGGTCACCATCACCATCACCATGGCAGCGGTTCTAGTCT

-continued

AGCGGCCGCAACTGATCTTGGC
(wherein N is any base)

SEQ ID NO: 28 = FG10
   GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNNNNNNTCTAACCCGCTGTCTGCGATCTTCACCA

CCGGCGGTCACCATCACCATCACCATGGCAGCGGTTCTAGTCTAGC

GGCCGCAACTGATCTTGGC
(wherein N is any base)

SEQ ID NO: 29 = FG9
   GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNNNTCTAACCCGCTGTCTGCGATCTTCACCACCG

GCGGTCACCATCACCATCACCATGGCAGCGGTTCTAGTCTAGCGGC

CGCAACTGATCTTGGC
(wherein N is any base)

SEQ ID NO: 30 = FG8
   GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNTCTAACCCGCTGTCTGCGATCTTCACCACCGGCG

GTCACCATCACCATCACCATGGCAGCGGTTCTAGTCTAGCGGCCGC

AACTGATCTTGGC
(wherein N is any base)

SEQ ID NO: 31 = FG7
   GTGACACGGCGGTTAGAACGCGGCTACAATTAATACATAACCCCAT

CCCCCTGTTGACAATTAATCATCGGCTCGTATAATGTGTGGAATTG

-continued

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNTCTAACCCGCTGTCTGCGATCTTCACCACCGGCGGTC

ACCATCACCATCACCATGGCAGCGGTTCTAGTCTAGCGGCCGCAACT

GATCTTGGC
(wherein N is any base)

SEQ ID NO: 32 = human mature CD71
MTKEYQDLQHLDNEESDHHQLRKGPPPPQPLLQRLCSGPRLLLLSL

GLSLLLLVVVCVIGSQNSQLQEELRGLRETFSNFTASTEAQVKGLS

TQGGNVGRKMKSLESQLEKQQKDLSEDHSSLLLHVKQFVSDLRSLS

CQMAALQGNGSERTCCPVNWVEHERSCYWFSRSGKAWADADNYCRL

EDAHLVVVTSWEEQKFVQHHIGPVNTWMGLHDQNGPWKWVDGTDYE

TGFKNWRPEQPDDWYGHGLGGGEDCAHFTDDGRWNDDVCQRPYRWV

CETELDKASQEPPLL

SEQ ID NO: 80 = human mature CD71
extracellular domain
QNSQLQEELRGLRETFSNFTASTEAQVKGLSTQGGNVGRKMKSLES

QLEKQQKDLSEDHSSLLLHVKQFVSDLRSLSCQMAALQGNGSERTC

CPVNWVEHERSCYWFSRSGKAWADADNYCRLEDAHLVVVTSWEEQK

FVQHHIGPVNTWMGLHDQNGPWKWVDGTDYETGFKNWRPEQPDDWY

GHGLGGGEDCAHFTDDGRWNDDVCQRPYRWVCETELDKASQEPPLL

| SEQ ID | Amino Acid sequence of FN3 domains that bind to CD71 |
| --- | --- |
| 33 | MLPAPKNLVVSRVTEDSARLSWTAPDAAFDSFTIQYEELTTVGEA IYLRVPGSERSYDLTGLKPGTEYVVVWIEGVKGGLRSNPLGAAFTT |
| 34 | MLPAPKNLVVSRVTEDSARLSWTAPDAAFDSFAITYIEWWDVGEA IGLKVPGSERSYDLTGLKPGTEYRVHIQGVKGGNNSYPLDALFTT |
| 35 | MLPAPKNLVVSRVTEDSARLSWTAPDAAFDSFEIAYFEAIWNGEA IYLTVPGSERSYDLTGLKPGTEYQVEIRGVKGGPTSRPLFAWFTT |
| 36 | MLPAPKNLVVSRVTEDSARLSWTAPDAAFDSFTITYIEWWENGEA IALSVPGSERSYDLTGLKPGTEYQVGIAGVKGGYKSYPLWALFTT |
| 37 | MLPAPKNLVVSRVTEDSARLSWTAPDAAFDSFHIIYTEEEKEGEA IYLRVPGSERSYDLTGLKPGTEYLVEIEGVKGGKRSVPLNASFTT |
| 38 | MLPAPKNLVVSRVTEDSARLSWTAPDAAFDSFHIAYEESHTTGEA IFLRVPGSERSYDLTGLKPGTEYSVSIEGVKGGHYSPPLTAKFTT |
| 39 | MLPAPKNLVVSRVTEDSARLSWTAPDAAFDSFDIDYREWWTLGEA IVLTVPGSERSYDLTGLKPGTEYYVNIQGVKGGLRSYPLSAIFTT |
| 40 | MLPAPKNLVVSRVTEDSARLSWTAPDAAFDSFVIEYWEYVGHGEA IVLTVPGSERSYDLTGLKPGTEYSVGIYGVKGGSLSRPLSAIFTT |
| 41 | MLPAPKNLVISRVTEDSARLSWTAPDAAFDSFFIYYIESYPAGEA IVLTVPGSERSYDLTGLKPGTEYWVGIDGVKGGRWSTPLSAIFTT |
| 42 | MLPAPKNLVVSRVTEDSARLSWTAPDAAFDSFTIEYYESFYGGEA IVLTVPGSERSYDLTGLKPGTEYYVSIYGVKGGWLSRPLSAIFTT |

-continued

```
SEQ   Amino Acid sequence of FN3 domains that
ID    bind to CD71

43    MLPAPKNLVVSRVTEDSARLSWTAPDAAFDSFYIEYYESYPGGEA
      IVLTVPGSERSYDLTGLKPGTEYDVYIYGVKGGYWSRPLSAIFTT

44    MLPAPKNLVVSRVTEDSARLSWTAPDAAFDSFYIEYYESLPDGEA
      IVLTVPGSERSYDLTGLKPGTEYAVYIYGVKGGYYSRPLSAIFTT

45    MLPAPKNLVVSRVTEDSARLSWTAPDAAFDSFAIYYLESYPEGEA
      IVLTVPGSERSYDLTGLKPGTEYWVGIDGVKGGTWSSPLSAIFTT

46    MLPAPKNLVVSRVTEDSARLSWTAPDAAFDSFTIEYFEFTGTGEA
      IVLTVPGSERSYDLTGLKPGTEYYVSIYGVKGGLLSAPLSAIFTT

47    MLPAPKNLVVSRVTEDSARLSWTAPDAAFDSFTIWYAEALGDGEA
      IVLTVPGSERSYDLTGLKPGTEYFVDIYGVKGGFWSLPLSAIFTT

48    MLPAPKNLVVSRVTEDSARLSWTAPDAAFDSFVIEYFEQFNLGEA
      IVLTVPGSERSYDLTGLKPGTEYWVGIYGVKGGWLSHPLSAIFTT

49    MLPAPKNLVVSRVTEDSARLSWTAPDAAFDSFGISYLEWWEDGEA
      IVLTVPGSERSYDLTGLKPGTEYWVSIAGVKGGKRSYPLSAIFTT

50    MLPAPKNLVVSRVTEDSARLSWTAPDAAFDSFVIEYREGAWYGEA
      IVLTVPGSERSYDLTGLKPGTEYFVDITGVKGGWWSDPLSAIFTT

51    MLPAPKNLVVSRVTEDSARLSWTAPDAAFDSFFIKYIEWWADGEA
      IVLTVPGSERSYDLTGLKPGTEYLVEIYGVKGGKWSWPLSAIFTT

52    MLPAPKNLVVSRVTEDSARLSWTAPDAAFDSFKISYQEWWEDGEA
      IVLTVPGSERSYDLTGLKPGTEYWVNISGVKGGVQSYPLSAIFTT

53    MLPAPKNLVVSRVTEDSARLSWTAPDAAFDSFFISYIEWWDLGEA
      IVLTVPGSERSYDLTGLKPGTEYHVEIFGVKGGTQSYPLSAIFTT

54    MLPAPKNLVVSRVTEDSARLSWTAPDAAFDSFQILYQENAFEGEA
      IVLTVPGSERSYDLTGLKPGTEYWVYIYGVKGGYPSVPLSAIFTT

55    MLPAPKNLVVSRVTEDSARLSWTAPDAAFDSFIIEYWEFVGYEAG
      IVLTVPGSERSYDLTGLKPGTEYWVAIYGVKGGDLSKPLSAIFTT

56    MLPAPKNLVVSRVTEDSARLSWTAPDAAFDSFVIEYFEALEGGEA
      IVLTVPGSERSYDLTGLKPGTEYFVGIYGVKGGPLSKPLSAIFTT

57    MLPAPKNLVVSRVTEDSARLSWTAPDAAFDSFSIKYLEWWQDGEA
      IVLTVPGSERSYDLTGLKPGTEYYVHIAGVKGGYRSYPLSAIFTT

58    MLPAPKNLVVSRVTEDSARLSWTAPDAAFDSFTIWYAEADGWGEA
      IVLTVPGSERSYDLTGLKPGTEYFVDIYGVKGGYLSVPLSAIFTT

59    MLPAPKNLVVSRVTEDSARLSWTAPDAAFDSFTIWYAEWEDEGEA
      IVLTVPGSERSYDLTGLKPGTEYRVEIYGVKGGYPSKPLSAIFTT

60    MLPAPKNLVVSRVTEDSARLSWTAPDAAFDSFTIWYAEAIGHGEA
      IVLTVPGSERSYDLTGLKPGTEYWVDIWGVKGGQQSKPLSAIFTT

61    MLPAPKNLVVSRVTEDSARLSWRVESRTFDSFLIQYQESEKVGEA
      IVLTVPGSERSYDLTGLKPGTEYTVSIYGVVWDTRDNPISNPLSA
      IFTT

62    MLPAPKNLVVSRVTEDSARLSWTAPDAAFDSFPILYLELNHHGEE
      IVLTVPGSERSYDLTGLKPGTEYWVYIFGVKGGMYSAPLSAIFTT
      GG
```

Example 4: Selection of Fibronectin Type III (FN3) Domains that Bind CD71

Panning and Biochemical Screening Methods for Identifying FN3 domains that bind to CD71 that do not inhibit transferrin binding to CD71. To screen for FN3 domains that specifically bind CD71 and do not inhibit transferring binding to CD71, streptavidin-coated Maxisorp plates (Nunc catalog 436110) are blocked for 1 hour in Starting Block T20 (Pierce) and then are coated with biotinylated CD71 (using same antigen as in panning) or negative controls (an unrelated Fc-fused recombinant protein and human serum albumin) for 1 hour in the presence of transferring or with FN3 protein that binds to the CD71 transferrin binding site. The concentration of transferrin is up to 35 μM. Without being bound to any particular theory, the inclusion of the transferrin or the FN3 protein that binds to the CD71 transferrin binding site pushes the selection of the FN3 domains to those that do not compete or inhibit with transferrin binding to CD71. Plates are rinsed with TBST and diluted lysate is applied to plates for 1 hour. Following additional rinses, wells are treated with HRP-conjugated anti-V5 tag antibody (Abcam, ab1325), for 1 hour and then are assayed with POD (Roche. 11582950001). The DNA from FN3 domain lysates with signals at least 10-fold ELISA signal above that of streptavidin controls are sequenced resulting in FN3 domain sequences isolated from the screening.

EXAMPLE 5: Selection of Fibronectin Type III (FN3) Domains that Bind CD71 and are not Competitive with Transferrin To identify CD71 binding FN3 domains that were either not competitive or minimally competitive with transferrin a biased CIS-display strategy was designed. In short, using the output recovered after 5 rounds of panning on the ECD of human CD71 (Example 3). Additional rounds of off-rate selection were performed as described in Example 3 with the addition of either 1) a wash step with human holo transferrin to elute Centyrins that bound at the same site as transferrin before the final elution step or 2) elution of FN3 domain binders with monoclonal antibody OKT9. FN3 domains recovered from the transferrin wash strategy and the OKT9 elution strategy were PCR amplified and cloned into pET vector as previously described (Example 3). 228 FN3 domains that specifically bound huCD71 were confirmed by ELISA for binding to huCD71 ECD (Table 8). A subset of the unique binders was analyzed by SEC (Table 9), conjugated to MMAF and assessed for internalization via cell viability assay in SKBR-3 cells +/–holo human transferrin (Table 10). The polypeptides were found to be internalized by the receptor. The data and sequences of the hits are identified in the following tables.

TABLE 8

| Summary of Screening Hits | | | |
|---|---|---|---|
| hCD71 | HSA | hCD71:HSA | SEQ ID NO: |
| 536550 | 28550 | 19 | 81 |
| 3525900 | 18900 | 187 | 82 |
| 1926800 | 1300 | 1482 | 83 |
| 1728500 | 3850 | 449 | 84 |
| 2912250 | 2500 | 1165 | 85 |
| 3387400 | 2250 | 1506 | 86 |
| 2833200 | 1100 | 2576 | 87 |
| 708250 | 6000 | 118 | 88 |
| 3444800 | 2000 | 1722 | 89 |
| 1093700 | 2550 | 429 | 90 |
| 1440400 | 1800 | 800 | 91 |
| 3845200 | 1300 | 2958 | 92 |
| 2162550 | 1650 | 1311 | 93 |
| 439050 | 9900 | 44 | 94 |
| 4206300 | 1900 | 2214 | 95 |
| 2714300 | 1500 | 1810 | 96 |
| 2405750 | 2200 | 1094 | 97 |
| 1159200 | 15500 | 75 | 98 |
| 853050 | 8150 | 105 | 99 |
| 2954050 | 2350 | 1257 | 100 |
| 1965650 | 9100 | 216 | 101 |

51

52

TABLE 8-continued

TABLE 8-continued

Summary of Screening Hits

Summary of Screening Hits

| hCD71 | HSA | hCD71:HSA | SEQ ID NO: |
|---|---|---|---|
| 3476400 | 13450 | 258 | 102 |
| 4828150 | 1200 | 4023 | 103 |
| 3575700 | 1700 | 2103 | 104 |
| 1758350 | 1400 | 1256 | 105 |
| 593650 | 1200 | 495 | 106 |
| 419800 | 4050 | 104 | 107 |
| 3189250 | 1300 | 2453 | 108 |
| 4831750 | 1250 | 3865 | 109 |
| 1680700 | 18850 | 89 | 110 |
| 2399600 | 7450 | 322 | 111 |
| 3652100 | 7100 | 514 | 112 |
| 2138900 | 22550 | 95 | 113 |
| 3274950 | 4200 | 780 | 114 |
| 2917250 | 3450 | 846 | 115 |
| 536350 | 1500 | 358 | 116 |
| 1498750 | 23500 | 64 | 117 |
| 2244850 | 18850 | 119 | 118 |
| 3156200 | 1850 | 1706 | 119 |
| 3636800 | 1850 | 1966 | 120 |
| 2372350 | 28600 | 83 | 121 |
| 2305100 | 29550 | 78 | 122 |
| 707200 | 3100 | 228 | 123 |
| 605100 | 3450 | 175 | 124 |
| 2329300 | 1050 | 2218 | 125 |
| 4494550 | 1750 | 2568 | 126 |
| 3556050 | 93300 | 38 | 127 |
| 663600 | 3250 | 204 | 128 |
| 2311100 | 1500 | 1541 | 129 |
| 1446000 | 6050 | 239 | 130 |
| 2183100 | 2400 | 910 | 131 |
| 2747200 | 2350 | 1169 | 132 |
| 4277350 | 5000 | 855 | 133 |
| 3080150 | 1950 | 1580 | 134 |
| 2056200 | 1500 | 1371 | 135 |
| 4026050 | 5700 | 706 | 136 |
| 484350 | 2050 | 236 | 137 |
| 4178200 | 3500 | 1194 | 138 |
| 3034550 | 2100 | 1445 | 139 |
| 4175400 | 1600 | 2610 | 140 |
| 2041000 | 3150 | 648 | 141 |
| 3413400 | 3400 | 1004 | 142 |
| 3940800 | 9250 | 426 | 143 |
| 2711900 | 2750 | 986 | 144 |
| 1615500 | 48450 | 33 | 145 |
| 3074850 | 3800 | 809 | 146 |
| 2363750 | 71250 | 33 | 147 |
| 3976550 | 2000 | 1988 | 148 |
| 2768350 | 3350 | 826 | 149 |
| 2617600 | 3500 | 748 | 150 |
| 1770200 | 54950 | 32 | 151 |
| 2831150 | 5300 | 534 | 152 |
| 956700 | 13100 | 73 | 153 |
| 2779300 | 4150 | 670 | 154 |
| 1837850 | 25950 | 71 | 155 |
| 1028500 | 5000 | 206 | 156 |
| 2657950 | 2450 | 1085 | 157 |
| 2055750 | 1350 | 1523 | 158 |
| 2581000 | 1950 | 1324 | 159 |
| 2759200 | 3300 | 836 | 160 |
| 1214400 | 5050 | 240 | 161 |
| 3876250 | 1850 | 2095 | 162 |
| 3047800 | 4400 | 693 | 163 |
| 2605000 | 1100 | 2368 | 164 |
| 2642300 | 65200 | 41 | 165 |
| 2421600 | 5050 | 480 | 166 |
| 2618650 | 3600 | 727 | 167 |
| 2896650 | 1950 | 1485 | 168 |
| 2853900 | 2700 | 1057 | 169 |
| 981650 | 16800 | 58 | 170 |
| 3720500 | 1900 | 1958 | 171 |
| 4309800 | 3700 | 1165 | 172 |
| 979050 | 20850 | 47 | 173 |
| 2422100 | 2200 | 1101 | 174 |
| 3550650 | 1600 | 2219 | 175 |
| 1336350 | 10350 | 129 | 176 |

| hCD71 | HSA | hCD71:HSA | SEQ ID NO: |
|---|---|---|---|
| 2608650 | 2450 | 1065 | 177 |
| 1447950 | 2250 | 644 | 178 |
| 2684550 | 74700 | 36 | 179 |
| 1678750 | 33500 | 50 | 180 |
| 2945100 | 6000 | 491 | 181 |
| 3116750 | 2950 | 1057 | 182 |
| 1724000 | 10700 | 161 | 183 |
| 470400 | 2000 | 235 | 184 |
| 1809500 | 9950 | 182 | 185 |
| 2024550 | 1850 | 1094 | 186 |
| 3061100 | 7250 | 422 | 187 |
| 2669350 | 3350 | 797 | 188 |
| 1962850 | 67500 | 29 | 189 |
| 3214200 | 4900 | 656 | 190 |
| 1465100 | 33950 | 43 | 191 |
| 2666650 | 4100 | 650 | 192 |
| 3872950 | 2500 | 1549 | 193 |
| 562350 | 17800 | 32 | 194 |
| 2532200 | 90200 | 28 | 195 |
| 1719750 | 34550 | 50 | 196 |
| 4566550 | 18900 | 242 | 197 |
| 3441600 | 3050 | 1128 | 198 |
| 1461350 | 14450 | 101 | 199 |
| 3626550 | 2100 | 1727 | 200 |
| 1197600 | 11350 | 106 | 201 |
| 4503050 | 2800 | 1608 | 202 |
| 3382850 | 3300 | 1025 | 203 |
| 2766650 | 24550 | 113 | 204 |
| 434050 | 3350 | 130 | 205 |
| 833350 | 2650 | 314 | 206 |
| 1596550 | 25600 | 62 | 207 |
| 2289200 | 46700 | 49 | 208 |
| 790150 | 13750 | 57 | 209 |
| 1156900 | 2250 | 514 | 210 |
| 1001850 | 3000 | 334 | 211 |
| 2490750 | 2250 | 1107 | 212 |
| 2105500 | 9800 | 215 | 213 |
| 2143100 | 2200 | 974 | 214 |
| 2125250 | 1750 | 1214 | 215 |
| 2192150 | 21800 | 101 | 216 |
| 3902700 | 11750 | 332 | 217 |
| 2388200 | 33800 | 71 | 218 |
| 3307550 | 2600 | 1272 | 219 |
| 4247800 | 9400 | 452 | 220 |
| 1959700 | 3650 | 537 | 221 |
| 1741200 | 3950 | 441 | 222 |
| 1666800 | 51950 | 32 | 223 |
| 2017650 | 16500 | 122 | 224 |
| 2962400 | 14100 | 210 | 225 |
| 4332150 | 2850 | 1520 | 226 |
| 3853700 | 2300 | 1676 | 227 |
| 2542750 | 2400 | 1059 | 228 |
| 570000 | 3700 | 154 | 229 |
| 1998400 | 1900 | 1052 | 230 |
| 2268400 | 26500 | 86 | 231 |
| 1699150 | 2700 | 629 | 232 |
| 3412150 | 2600 | 1312 | 233 |
| 680200 | 7200 | 94 | 234 |
| 3923600 | 1350 | 2906 | 235 |
| 3444750 | 1500 | 2297 | 236 |
| 4148900 | 1850 | 2243 | 237 |
| 2883800 | 4250 | 679 | 238 |
| 418900 | 5050 | 83 | 239 |
| 3033700 | 2050 | 1480 | 240 |
| 2696100 | 2200 | 1226 | 241 |
| 871750 | 4900 | 178 | 242 |
| 2402150 | 10150 | 237 | 243 |
| 545300 | 1650 | 330 | 244 |
| 2617750 | 2900 | 903 | 245 |
| 1573350 | 1400 | 1124 | 246 |
| 916150 | 53050 | 17 | 247 |
| 831650 | 15100 | 55 | 248 |
| 1047250 | 7100 | 148 | 249 |
| 1094500 | 18750 | 58 | 250 |
| 2738000 | 9650 | 284 | 251 |

53

TABLE 8-continued

Summary of Screening Hits

| hCD71 | HSA | hCD71:HSA | SEQ ID NO: |
|---|---|---|---|
| 2979550 | 2500 | 1192 | 252 |
| 2801100 | 2450 | 1143 | 253 |
| 3243550 | 90000 | 36 | 254 |
| 1835800 | 4550 | 403 | 255 |
| 1978900 | 2200 | 900 | 256 |
| 2374200 | 3950 | 601 | 257 |
| 1041700 | 10600 | 98 | 258 |
| 2443600 | 2100 | 1164 | 259 |
| 1301700 | 14450 | 90 | 260 |
| 4233400 | 5550 | 763 | 261 |
| 4380350 | 2350 | 1864 | 262 |
| 1878900 | 20400 | 92 | 263 |
| 2977200 | 2550 | 1168 | 264 |
| 3606650 | 3950 | 913 | 265 |
| 894150 | 2650 | 337 | 266 |
| 1969550 | 11900 | 166 | 267 |
| 1597000 | 2550 | 626 | 268 |
| 690150 | 4150 | 166 | 269 |
| 1809350 | 2400 | 754 | 270 |
| 2114700 | 3050 | 693 | 271 |
| 1784450 | 8950 | 199 | 272 |
| 4651050 | 9150 | 508 | 273 |
| 522300 | 11900 | 44 | 274 |
| 2245050 | 3800 | 591 | 275 |
| 720100 | 12350 | 58 | 276 |
| 3110300 | 5200 | 598 | 277 |
| 3689600 | 6500 | 568 | 278 |
| 4089350 | 3150 | 1298 | 279 |
| 445950 | 21550 | 21 | 280 |
| 1073150 | 22400 | 48 | 281 |
| 3851150 | 18650 | 206 | 282 |
| 2952800 | 6250 | 472 | 283 |
| 2901100 | 5250 | 553 | 284 |
| 2435900 | 2200 | 1107 | 285 |
| 1270750 | 10750 | 118 | 286 |
| 3882900 | 5500 | 706 | 287 |
| 658700 | 40800 | 16 | 288 |
| 2268450 | 2150 | 1055 | 289 |
| 2810350 | 11850 | 237 | 290 |
| 3829050 | 2150 | 1781 | 291 |
| 2620700 | 8850 | 296 | 292 |
| 3588450 | 6900 | 520 | 293 |
| 1436450 | 8250 | 174 | 294 |
| 3384850 | 3800 | 891 | 295 |
| 2701450 | 3200 | 844 | 296 |
| 2594250 | 52550 | 49 | 297 |
| 2514000 | 34050 | 74 | 298 |
| 4270100 | 2200 | 1941 | 299 |
| 2311150 | 4050 | 571 | 300 |
| 659800 | 12050 | 55 | 301 |
| 2672850 | 21200 | 126 | 302 |
| 3513150 | 2650 | 1326 | 303 |
| 3343900 | 2700 | 1238 | 304 |
| 1207900 | 25000 | 48 | 305 |
| 4068850 | 2250 | 1808 | 306 |
| 2185950 | 4350 | 503 | 307 |
| 608900 | 12300 | 50 | 308 |
| 3142450 | 2850 | 1103 | 309 |

TABLE 9

Summary of Size Exclusion Chromatography Analysis

| SEQ ID NO: | RT (min) | Height (mAU) |
|---|---|---|
| 81 | 5.117 | 14621 |
| 82 | 5.11 | 24062 |
| 83 | 5.114 | 91333 |
| 84 | 5.032 | 65838 |
| 85 | 5.075 | 78484 |
| 86 | 5.149 | 210493 |

54

TABLE 9-continued

Summary of Size Exclusion Chromatography Analysis

| SEQ ID NO: | RT (min) | Height (mAU) |
|---|---|---|
| 87 | 5.1 | 77812 |
| 88 | 5.14 | 194249 |
| 89 | 5.006 | 61555 |
| 90 | 5.071 | 177756 |
| 91 | 5.092 | 127220 |
| 92 | 5.217 | 179747 |
| 93 | 5.043 | 35064 |
| 94 | 6.706 | 2222 |
| 95 | 5.112 | 75615 |
| 96 | 5.066 | 71880 |
| 97 | 5.144 | 101200 |
| 98 | 4.561 | 29769 |
| 99 | 3.764 | 3242 |
| 100 | 5.158 | 163566 |
| 101 | 5.049 | 70310 |
| 102 | 5.06 | 48409 |
| 103 | 5.047 | 85919 |
| 104 | 5.04 | 67751 |
| 105 | 5.076 | 79635 |
| 106 | 5.092 | 100250 |
| 107 | 3.755 | 3878 |
| 108 | 5.131 | 109212 |
| 109 | 5.048 | 72864 |
| 110 | 5.037 | 25838 |
| 111 | 5.046 | 82613 |
| 112 | 5.037 | 69662 |
| 113 | 5.06 | 1660 |
| 114 | 5.058 | 93289 |
| 115 | 5.008 | 59386 |
| 116 | 6.701 | 78 |
| 117 | 5.001 | 16853 |
| 119 | 5.026 | 49470 |
| 120 | 5.247 | 131571 |
| 121 | 4.494 | 4134 |
| 122 | 4.576 | 20348 |
| 123 | 4.572 | 16021 |
| 124 | 5.018 | 69849 |
| 125 | 5.007 | 69810 |
| 126 | 5.075 | 64475 |
| 127 | 5.07 | 12214 |
| 128 | 5.107 | 58225 |
| 129 | 5.005 | 122592 |
| 130 | 5.051 | 116931 |
| 131 | 5.073 | 95190 |
| 132 | 5.038 | 106856 |
| 133 | 5.082 | 20172 |
| 134 | 5.118 | 97944 |
| 135 | 5.032 | 97600 |
| 136 | 5.157 | 66595 |
| 137 | 5.032 | 156482 |
| 138 | 5.181 | 124800 |
| 139 | 4.978 | 96486 |
| 140 | 5.024 | 78145 |
| 141 | 5.095 | 115919 |
| 142 | 5.067 | 52467 |
| 143 | 5.042 | 50518 |
| 144 | 5.062 | 82962 |
| 145 | 4.542 | 18503 |
| 146 | 5.031 | 88958 |
| 147 | 4.509 | 8929 |
| 148 | 5.098 | 91401 |
| 149 | 5.055 | 79364 |
| 150 | 4.976 | 57089 |
| 151 | 4.469 | 10958 |
| 152 | 5.017 | 67201 |
| 153 | 5.108 | 89015 |
| 154 | 5.083 | 73990 |
| 155 | 4.57 | 3820 |
| 156 | 5.053 | 125648 |
| 157 | 5.131 | 96835 |
| 158 | 4.964 | 86205 |
| 159 | 4.994 | 66919 |
| 160 | 5.11 | 94133 |
| 161 | 5.018 | 103592 |
| 162 | 5.157 | 96072 |

TABLE 9-continued

Summary of Size Exclusion Chromatography Analysis

| SEQ ID NO: | RT (min) | Height (mAU) |
|---|---|---|
| 163 | 5.049 | 121129 |
| 164 | 5.115 | 79403 |
| 165 | 4.547 | 6562 |
| 166 | 5.023 | 125865 |
| 167 | 4.975 | 63859 |
| 168 | 5.043 | 86853 |
| 169 | 5.017 | 95640 |
| 170 | 5.04 | 54100 |
| 171 | 5.18 | 180492 |
| 172 | 5.229 | 70453 |
| 173 | 3.662 | 17075 |
| 174 | 4.999 | 268853 |
| 175 | 5.044 | 272743 |
| 178 | 5.063 | 40232 |
| 179 | 5.11 | 233798 |
| 180 | 5.028 | 268714 |
| 181 | 5.049 | 175217 |
| 182 | 5.024 | 347191 |
| 183 | 5.161 | 269305 |
| 184 | 4.967 | 236502 |
| 185 | 5.018 | 190752 |
| 186 | 5.081 | 342318 |
| 187 | 5.038 | 127542 |
| 188 | 5.043 | 140513 |
| 189 | 5.058 | 218023 |
| 190 | 4.535 | 55627 |
| 191 | 5.026 | 199881 |
| 192 | 4.708 | 31553 |
| 193 | 5.086 | 1933389 |
| 194 | 5.046 | 253626 |
| 195 | 4.969 | 143010 |
| 196 | 4.996 | 80332 |
| 197 | 5.009 | 141197 |
| 198 | 5.1 | 139202 |
| 199 | 5.126 | 123977 |
| 200 | 5.449 | 1886 |
| 201 | 5.047 | 226703 |
| 203 | 4.955 | 172346 |
| 204 | 4.987 | 159535 |
| 205 | 5.09 | 237874 |
| 206 | 5.01 | 182142 |
| 207 | 5.144 | 190642 |
| 208 | 5.034 | 190328 |
| 209 | 5.104 | 221965 |
| 210 | 5053 | 5060 |
| 211 | 5.009 | 287859 |
| 212 | 4.969 | 187947 |
| 213 | 5.026 | 219651 |
| 214 | 4.999 | 181968 |
| 215 | 5.034 | 111935 |
| 216 | 5.158 | 401933 |
| 217 | 5.197 | 275205 |
| 218 | 4.447 | 74121 |
| 219 | 4.97 | 215336 |
| 220 | 5.051 | 260942 |
| 221 | 4.957 | 123233 |
| 222 | 5.03 | 1674429 |
| 223 | 5.012 | 145280 |
| 224 | 5.534 | 2310 |
| 225 | 5.017 | 54242 |
| 226 | 5.001 | 142955 |
| 227 | 5.024 | 212808 |
| 228 | 5.039 | 1149, 33 |
| 229 | 5.064 | 177947 |
| 230 | 4.983 | 202000 |
| 231 | 5.013 | 182975 |
| 232 | 5.121 | 223657 |
| 233 | 5.092 | 172952 |
| 234 | 3.951 | 84866 |
| 235 | 5.058 | 142138 |
| 236 | 5.063 | 367688 |
| 237 | 5.004 | 165516 |
| 238 | 5.069 | 218298 |
| 239 | 5.086 | 361567 |
| 240 | 5.127 | 252675 |

TABLE 9-continued

Summary of Size Exclusion Chromatography Analysis

| SEQ ID NO: | RT (min) | Height (mAU) |
|---|---|---|
| 241 | 5.071 | 233781 |
| 242 | 5.008 | 268637 |
| 243 | 5.092 | 168008 |
| 244 | 5.119 | 79488 |
| 245 | 5.06 | 215547 |
| 246 | 5.008 | 53653 |
| 247 | 5.075 | 250310 |
| 248 | 5.094 | 194793 |
| 249 | 3.616 | 37488 |
| 250 | 5.036 | 301239 |
| 251 | 5.101 | 297658 |
| 252 | 4.965 | 53405 |
| 253 | 4.65 | 4466 |
| 254 | 3.66 | 16463 |
| 255 | 5.032 | 253885 |
| 256 | 4.976 | 244457 |
| 257 | 5.072 | 289009 |
| 258 | 5.106 | 273939 |
| 259 | 5.041 | 166066 |
| 260 | 5.004 | 160654 |
| 261 | 4.972 | 164451 |
| 262 | 5.148 | 513577 |
| 263 | 5.089 | 208950 |
| 264 | 5.099 | 206909 |
| 265 | 5.051 | 68567 |
| 266 | 4.996 | 72025 |
| 267 | 5.085 | 106826 |
| 268 | 4.865 | 7221 |
| 269 | 5.138 | 63713 |
| 270 | 5.186 | 149808 |
| 271 | 5.019 | 85191 |
| 272 | 5.277 | 118699 |
| 273 | 5.069 | 104693 |
| 274 | 5.022 | 17776 |
| 275 | 5.055 | 138448 |
| 276 | 4.95 | 16306 |
| 277 | 5.079 | 139094 |
| 278 | 5 | 82052 |
| 279 | 5.088 | 3310 |
| 280 | 5.22 | 127670 |
| 281 | 5.039 | 157800 |
| 282 | 5.003 | 109468 |
| 283 | 5.074 | 123519 |
| 284 | 5.039 | 12331 |
| 285 | 5.223 | 148145 |
| 286 | 5.136 | 148676 |
| 287 | 3.665 | 7404 |
| 288 | 5.575 | 1112 |
| 289 | 3.696 | 9460 |
| 290 | 5.029 | 93755 |
| 291 | 5.095 | 169623 |
| 292 | 3.689 | 14445 |
| 293 | 4.634 | 36542 |
| 294 | 5.004 | 77308 |
| 295 | 4.998 | 17822 |
| 296 | 5.003 | 74551 |
| 297 | 5.085 | 68904 |
| 298 | 5.192 | 129131 |
| 299 | 4.54 | 30337 |
| 300 | 5.025 | 142111 |
| 301 | 5.028 | 84156 |
| 302 | 4.992 | 78611 |
| 303 | 4.527 | 25755 |
| 304 | 5.065 | 122824 |
| 305 | 3.668 | 7392 |
| 306 | 5.065 | 145979 |
| 307 | 5.097 | 135403 |
| 308 | 5.059 | 18037 |
| 309 | 5.198 | 111922 |

TABLE 10

IC50 of CD71 FN3 domain - MMAF conjugate molecules 5 on
SKBR-3 cells +/− human transferrin

| | IC50 (nM) | |
|---|---|---|
| SEQ ID NO: | huTf competitor | no competitor |
| 146 | 7.131 | 3.457 |
| 214 | 28.15 | 29.23 |
| 104 | 301.3 | 5.9 |
| 259 | 27.46 | N.D. |
| 134 | 164.9 | 8.543 |
| 92 | 5.489 | 1.061 |
| 302 | 164.3 | 27.81 |
| 235 | 1.755 | 10.58 |
| 237 | 28.12 | 3.762 |
| 152 | 19.56 | 5.239 |
| 238 | N.D. | 7.232 |
| 136 | 2.32 | 0.5026 |
| 197 | N.D. | 0.4675 |
| 212 | N.D. | 6.691 |
| 296 | 29.31 | 18.61 |
| 226 | N.D. | 8.32 |
| 261 | 1.235 | 31.2 |
| 307 | 47.89 | 30.75 |
| 115 | 24.22 | 10.43 |
| 112 | 27.33 | 4.549 |
| 278 | 13.24 | 3.702 |
| 297 | N.D. | N.D. |
| 96 | 79.5 | 27 |
| 222 | N.D. | 28.23 |
| 95 | 28.27 | 12.68 |
| 233 | 54.61 | 17.7 |
| 217 | 15.78 | 2.458 |
| 252 | 24.55 | 7.736 |
| 194 | N.D. | 5.091 |
| 164 | 18.7 | 55.8 |
| 168 | 32 | 7.2 |
| 174 | ND | 158 |
| 190 | 36 | 12 |
| 257 | 22 | 6.5 |
| 303 | 33 | 39 |
| 284 | 98 | 32 |
| 85 | ND | 89 |
| 149 | 9.7 | 5.5 |

SEQ
ID Amino Acid sequence of FN3 domains
NO: that bind to CD71

81 MLPAPKNLVVSRVTEDSARLSWTAPDAAFDSFVIEYREGAWYGEA
IVLTVPGSERSYDLTGLKPGTEYAVYIPGVKGGPRSFPLSAIFTT

82 MLPAPKNLVVSRVTEDSARLSWTAPDAAFDSFAIAYVEWWKLGEA
IVLTVPGSERSYDLTGLKPGTEYVVPIPGVKGGHSSPLSAIFTT

83 MLPAPKNLVVSRVTEDSARLSWTAPDAAFDSFYIYYYESSGTGEA
IVLTVPGSERSYDLTGLKPGTEYFVDIGGVKGGSYSLPLSAIFTT

84 MLPAPKNLVVSRVTEDSARLSWTAPDAAFDSFPIYYWEVFPAGEA
IELDVPGSERSYDLTGLKPGTEYFVRIEGVKGGASSYPLRAEFTT

85 MLPAPKNLVVSRVTEDSARLSWTAPDAAFDSFFIWYWEKSVDGEA
IVLTVPGSERSYDLTGLKPGTEYNVGIQGVKGGTPSDPLSAIFTT

86 MLPAPKNLVVSRVTEDSARLSWTAPDAAFDSFIIWYAEWVNDGEA
IVLTVPGSERSYDLTGLKPGTEYRVEITGVKGGTWSRPLSAIFTT

87 MLPAPKNLVVSRVTEDSARLSWTAPDAAFDSFAIEYYEPVPAGEA
IYLDVPGSERSYDLTGLKPGTEYDVTIYGVKGGYYSHPLFASFTT

88 MLPAPKNLVVSRVTEDSARLSWTAPDAAFDSFWIEYFEWTVGGEA
IVLTVPGSERSYDLTGLKPGTEYYVSIYGVKGGWLSPPLSAIFTT

89 MLPAPKNLVVSRVTEDSARLSWTAPDAAFDSFHISYEETPVVGEA
IYLRVPGSERSYDLTGLKPGTEYTVAIHGVKGGRESTPLIAPFTT

-continued

SEQ
ID Amino Acid sequence of FN3 domains
NO: that bind to CD71

90 MLPAPKNLVVSRVTEDSARLSWTAPDAAFDSFTIHYWEFDPPGEA
IVLTVPGSERSYDLTGLKPGTEYTVYIEGVKGGWWSKPLSAIFTT

91 MLPAPKNLVVSRVTEDSARLSWTAPDAAFDSFVIEYWERTQPGEA
IVLTVPGSERSYDLTGLKPGTEYDVWISGVKGGKWSEPLSAIFTT

92 MLPAPKNLVVSRVTEDSARLSWTAPDAAFDSFLIRYWEWYVLGEA
IVLTVPGSERSYDLTGLKPGTEYYVEISGVKGGWQSWPLSAIFTT

93 MLPAPKNLVVSRVTEDSARLSWTAPDAAFDSFYIGYLEPGDNGEA
IVLTVPGSERSYDLTGLKPGTEYNVSIGGVKGGLGSYPLSAIFTT

94 MLPAPKNLVVSRITEDSARLSWTAPDAAFDSFGIYYYEWWSTGEA
IVLTVPGSERSYDLTGPKPGTEYYVKISGVKGGYRSYPLSAIFTT

95 MLPAPKNLVVSRVTEDSARLSWTAPDAAFDSFRISYYEWYDLGEA
IVLTVPGSERSYDLTGLKPGTEYWVDIAGVKGGYYSYPLSAIFIT

96 MLPAPKNLVVSRVTEDSARLSWTAPDAAFDSFFIGYLEPQPPGEA
IVLTVPGSERSYDLTGLKPGTEYNVTIQGVKGGFPSMPLSAIFTT

97 MLPAPKNLVVSRVTEDSARLSWTAPDAAFDSFFISYFEGWASGEA
IHLYVPGSERSYDLTGLKPGTEYSVHIQGVKGGQPSTPLSAIFTT

98 MLPAPKNLVVSRITEDSARLSWTAPDAAFDSFDIPYGEFDTIGEA
IVLTVPGSERSYDLTGLKPGTEYDVYIEGVKGGHLSWPLSAIFTT

99 MLPAPKNLVVSRVTEDSARLSWTAPDAAFDSFGIQYNEFVFRGEA
IVLTVPGSERSYDLTGLKPGTEYFVPISGVKGGDDSRPLSAIFTT

100 MLPAPKNLVVSRVTEDSARLSWTAPDAAFDSFWIEYWEVVGFGEA
IVLTVPGSERSYDLTGLKPGTEYWVGIYGVKGGNPSVPLSAIFTT

101 MLPAPKNLVVSRVTEDSARLSWTAPDAAFDSFAIDYDEPINSGEA
IVLTVPGSERSYDLTGPKPGTEYEVEIYGVKGGYLSRPLSAIFTT

102 MLPAPKNLVVSRVTEDSARLSWTAPDAAFDSFSIDYDEPQPVGEA
IVLTVPGSERSYDLTGLKPGTEYRVDIWGVKGGPTSGPLRATFTT

103 MLLAPKNLVVSRVTEDSARLSWTAPDAAFDSFAIEYFEYTGEGEA
IVLTVPGSERSYDLTGLKPGTEYYVGIYGVKGGYLSRPLSAIFTT

104 MLPAPKNLVVSHVTEDSARLSWTAPDAAFDSFDIEYYELVGSGEA
IVLTVPGSERSYDLTGLKPGTEYYVAIYGVKGGYLSRPLSAIFTT

105 MLPAPKNLVVSRVTEDSARLSWTAPDAAFDSFGIAYYERSGAGEA
IVLTVPGSERSYDLTGLKPGTEYMVYINGVKGGFVSSPLSAIFTT

106 MLPAPKNLVVSRVTEDSARLSWTAPDAAFDSFTIAYEEHGLVGEA
IYLRVPGSERSYDLTGLKPGTEYHVGIMGVKGGVFSSPLSAIFTT

107 MLPAPKNLVVSRVTEDSARLSWTAPDAAFDSFFIQYTESHWVGEA
IVLTVPGSERSYDLTGLKPGTEYAVPIEGVKGGDSSTPLSAIFTT

108 MLPAPKNLVVSRVTEDSARLSWTAPDAAFDSFTIIYGEVNPYGEA
IVLTVPGSERSYDLTGLKPGTEYDVFIEGVKGGHLSWPLSAIFTT

109 MLPAPKNLVVSRVTEDSARLSWTAPDAAFDSFHIAYEELVTEGEA
IYLRVPGSERSYDLTGLKPGTEYLVDIEGVKGGHLSSPLSAIFTT

110 MLPAPKNLVVSRVTEDSARLSWTAPDAAFDSFFIHYHEWWEAGEA
IVLTVPGSERSYDLTGLKPGTEYLVDIPGVKGGDLSVPLSAIFTT

111 MLPAPKNLVVSRVTEDSARLSWTAPDAAFDSFWIYYYESVGTGEA
IVLTVPGSERSYDLTGLKPGTEYFVDISGVKVGTYSLPLSAIFTT

112 MLPAPKNLVVSRVTEDSARLSWTAPDAAFDSFFIAYFEFANPGEA
IVLTVPGSERSYDLTGLKPGTEYKVVIQGVKGGTPSEPLSAISTT

113 MLPAPKNLVVSRVTEDSARLSWTAPDAAFDSFDIHYKEHSWWGEA
IVLTVPGSERSYDLTGLKPGTEYIVPIPGVKGGGISRPLSAIFTT

114 MLPAPKNLVVSRVTEDSARLSWTAPDAAFDSFAIEYWEAVGSGEA
IVLTVPGSERSYDLTGLKPGTEYHVYIYGVKGGYLSLPLSAIFTT

-continued

SEQ
ID  Amino Acid sequence of FN3 domains
NO: that bind to CD71

115 MLPAPKNLVVSRVTEDSARLSWTAPDAAFDSFFIGYLEPQPPGEA
    IVLTVPGSERSYDLTGLKPGTEYNVTIQGVKGGFPSMPLSAIFTT
    T

116 MLPAPKNLVVSRVTEDSARLSWTAPDAAFDSFSIAYSEVRYDGEA
    IVLTVPGSERSYDLTGLKPGTEYVVPIGGVKGGGSSSPLSAIFTT

117 MLPAPKNLVVSRVTEDSARLSWTAPDAAFDSFTIPYGEAFNPGEA
    IVLTVPGSERSYDLTGLKPGTEYDVFIEGVKGGTLSWPLSAIFTT

118 MLPAPKNLVVSRVTEDSARLSWTAPDAAFDSFRILYGEVDPWGEA
    IVLTVPGSERSYDLTGLKPGTEYDVWIEGVKGGKLSWPLSAIFTT

119 MLPAPKNLVVSRVTEDSARLSWTAPDAAFDSFHIEYEETPQKGEA
    IFLRVPGSERSYDLTGLKPGTEYVVNIRGVKGGDLSSPLGALFTT

120 MLPAPKNLVVSRVTEDSARLSWTAPDAAFDSFRIEYIEWWVGGEA
    IVLTVPGSERSYDLTGLKPGTEYWVDIKGVKGGKRSYPLSAIFTT

121 MLPAPKNLVVSRVTEDSARLSWTAPDAAFDSFSIDYPEFPVRGEA
    IVLTVPGSERSYDLTGPKPGTEYNVTIQGVKGGFPSMPLSAIFTT

122 MLPAPKNLVVSRVTEDSARLSWTAPDAAFDSFQIPYWEQSLGGEA
    IVLTVPGSERSYDLTGLKPGTEYEVWIEGVKGGDLSFPLSAISTT

123 MLPAPKNLVVSRVTEDSARLSWTAPDAAFDSFVIPYEEYLYTGEA
    IVLTVPGSERSYDLTGLKPGTEYDVWIEGVKGGLTSWPLSAIFTT

124 MLPAPKNLVVSRVTEDSARLSWTAPDAAFDSFSIDYPEFPVRGEA
    IVLTVPGSERSYDLTGLKPGTEYAVTIWGVKGGFTSQPLSAIFTT

125 MLPAPKNLVVSRVTEDSARLSWTAPDAAFDSFVIEYFEFVGEGEA
    IVLTVPGSERSYDLTGLKPGTEYDVGIYGVKGGSLSSPLSAIFTT

126 MLPAPKNLVVSRVTEDSARLSWTAPDAAFDSFSIDYLELGESGEA
    IVLTVPGSERSYDLTGLKPGTEYWVYIFGVKGGYPSAPLSAIFTT

127 MLPAPKNLVVSRVTEDSARLSWTAPDAAFDSFPIPYGESPPSGEA
    IVLTVPGSERSYDLTGLKPGTEYVVIIRGVKGGGRSGPLSAISTT

128 MLPAPKNLVVSRVTEDSARLSWTAPDAAFDSFIINYIEIVQYGEA
    IVLTVPGSERSYDLTGLKPGTEYPESIWGVKGGGASSPLSAIFTT

129 MLPAPKNLVVSRVTEDSARLSWTAPDAAFDSFDIEYYEAVGAGEA
    IVLTVPGSERSYDLTGLKPGTEYTVGIYGVKGGWLSKPLSVIFTT

130 MLPAPKNLVVSRVTEDSARLSWTAPDAAFDSFHIPYVEAEVPGEA
    IQLHVPGSERSYDLTGLKPGTEYYVEIWGVKGGFYSPPLIAEFTT

131 MLPAPKNLVVSRVTEDSARLSWTAPDAAFDSFSIDYYEGKGYGEA
    IVLTVPGSERSYDLTGLKPGTEYQVLISGVKGGKYSLPLSAIFTT

132 MLPAPKNLVVSRVTEDSARLSWTAPDAAFDSFTIVYAEVTYDGEA
    IVLTVPGSERSYDLTGLKPGTEYDVFIEGVKGGELSWPLSAIFTT

133 MLPAPKNLVVSRVTEDSARLSWTAPDAAFDSFPIVYGEAWVTGEA
    IVLTVPGSERSYDLTGLKPGTEYDVWIEGVKGGELSWPLSAIFTT

134 MLPAPKNLVVSRVTEDSARLSWTAPDAAFDSFWIDYYERKYVGEA
    IVLTVPGSERSYDLTGLKPGTEYEVTIYGVKGGWYSDPLSAIFTT

135 MLPAPKNLVVSRVTEDSARLSWTAPDAAFDSFPISYYEMSGLGEA
    IVLTVPGSERSYDLTGLKPGTEYMVYIFGVKGGLNSLPLSAIFTT

136 MLPAPKNLVVSRVTEDSARLSWTAPDAAFDSFFIYYIESYPAGEA
    IVLTVPGSERSYDLTGLKPGTEYWMGIDGVKGGRWSTPLSAIFTT

137 MLPAPKNLVVSRVTEDSARLSWTAPDAAFDSFEIEYDEPSVAGEA
    IVLTVPGSERSYDLTGLKPGTEYRVFIWGVKGGNQSWPLSAIFTT

138 MLPAPKNLVVSRVTEDSARLSWTAPDAAFDSFFIKYIEWWADGEA
    IVLTVPGSERSYDLTGLKPGTEYLVEIYGVKGGRQSYPLSAIFTT

-continued

SEQ
ID  Amino Acid sequence of FN3 domains
NO: that bind to CD71

139 MLPAPKNLVVSRVTEDSARLSWTAPDAAFDSFDISYWESGKYGEA
    IVLTVPGSESSYDLTGLKPGTEYLVDIFGVKGGYPSEPLSAIFTT

140 MLPAPKNLVVSRVTEDSARLSWTAPDAAFDSFWISYEESDTEGEA
    IYLRVPGSERSYDLTGLKPGTEYNVTIQGVKGGFPSMPLSAIFTT

141 MLPAPKNLVVSRVTEDSARLSWTAPDAAFDSFVIEYFEQFNLGEA
    IVLTVPGSERSYDLTGLKPGTEYLVGIYGVKGGWLSHPLSAIFTT

142 MLPAPKNLVVSRVTKDSARLSWTAPDAAFDSFHIAYEEATTYGEA
    IFLRVPGSERSYDLTGLKPGTEYEVKIHGVKGGADSKPLVAPFTT

143 MLPAPKNLVVSRVTEDSARLSWTAPDAAFDSFHIAYEEADSEGEA
    IYLRVPGSERSYDLTGLKPGTEYSVNIQGVKGGIVSFPLHAEFTT

144 MLPAPKNLVVSRVTEDSARLSWTAPDAAFDSFIIPYAEVRPDGEA
    IVLTVPGSERSYDLTGLKPGTEYSVLIHGVKGGKLSLPLSAIFTT

145 MLPAPKNLVVSRVTEDSARLSWTAPDAAFDSFFIPYAEPSPTGEA
    IVLTVPGSERSYDLTGLKPGTEYDVWIEGVKGGTLSWPLSAIFTT

146 MLPAPKNLVVSRVTEDSARLSWTAPDAAFDSFYIAYAEPRPDGEA
    IVLTVPGSERSYDLTGLKPGTEYSVLIHGVKGGLLSSPLSAIFTT

147 MLPAPKNLVVSRVTEDSARLSWTAPDAAFDSFFIGYLEPQPPGEA
    IVLTVPGSERSYDLTGLKPGTEYSVLIHGVKGGRNSDPLSAISTT

148 MLPAPKNLVVSRVTEDSARLSWTAPDAAFDSFHIEYEEQYSTGEA
    IYLRVPGSERSYDLTGLKPGTEYHVDIEGVKGGRRSFPLNAFFTT

149 MLPAPKNLVVSRVTEDSARLSWTAPDAAFDSFIIPYAEVRPDGEA
    IVLTVPGSERSYDLTGLKPGTEYSVLIHGVKGGKLSEPLSAIFTT

150 MLPAPKNLVVSRVTEDSARLSWTAPDAAFDSFPIAYAEPSPTGEA
    IVLTVPGSERSYDLTGLKPGTEYSVLIHGVKGGHLSDPLSAIFTT

151 MLPAPKNLVVSRVTEDSARLSWTAPDAAFDSFFIPYAEPSPTGEA
    IVLTVPGSERSYDLTGLKPGTEYGVVILGVKGGYGSDPLSAIFTT

152 MLPAPKNLVVSRVTEDSARLSWTAPDAAFDSFFIGYLEPQPPGEA
    IVLTVPGSERSYDLTGLKPGTEYNVTIQGVKGGFPSSPLSAIFTT

153 MLPAPKNLVVSRVTEDSARLSWTAPDAALDSFRIAYTEYFVGGEA
    IVLTVPGSERSYDLTGLKPGTEYGVGIYGVKGGAGSSPLSAIFTT

154 MLPAPKNLVVSRVTEDSARLSWTAPDAAFDSFFIPYAEPRPDGEA
    IVLTVPGSERSYDLTGLKPGTEYSVLIHGVKGGLLSSPLSAIFTT

155 MLPAPKNLVVSRVTEDSARLSWTAPDAAFDSFPITYRERSQYGEA
    IVLTVPGSERSYDLTGLKPGTEYVVPIEGVKGGRGSKPLSAIFTT

156 MLPAPKNLVVSRVTEDSARLSWTAPDAAFDSFAIEYFENLGIGEA
    IVLTVPGSERSYDLTGLKPGTEYVVNIYGVKGGWLSSPLSAIFTT

157 MLPAPKNLVVSRVTEDSARLSWTAPDAAFDSFAIEYYEYVGNGEA
    IVLTVPGSERSYDLTGLKPGTEYQVGIYGVKGGYYSRPLSAIFTT

158 MLPAPKNLVVSRVTEDSARLSWTAPDAAFDSFIIDYLELDDYGEA
    IVLTVPGSERSYDLTGLKPGTEYPVYIYGVKGGLPSTPLSAIFIT

159 MLPAPKNLVVSRVTEDSARLSWTAPDAAFDSFLIPYAETSPSGEA
    IVLTVPGSERSYDLTGLKPGTEYSVLIHGVKGGRNSDPLSAIFTT

160 MLPAPKNLVVSRVTEDSARLSWTAPDAAFDSFNIAYGEWRQHGEA
    IVLTVPGSERSYDLTGLKPGTEYDVFIDGVKGGNLSWPLSAIFTT

161 MLPAPKNLVVSRVTEDSARLSWTAPDAAFDSFTIRYWEELPTGEA
    IVLTVPGSERSYDLTGLKPGTEYTVEIFGVKGGYLSRPLSAISTT

162 MLPAPKNLVVSRVTEDSARLSWTAPDAAFDSFHIAYEEATTYGEA
    IFLRVPGSERSYDLTGLKPGTEYDVWIEGVKGGTISGPLSAIFTT

163 MLPAPKNLVVSRVTEDSARLSWTAPDAAFDSFPIAYAEPRPDGEA
    IVLTVPGSERSYDLTGLKPGTEYFVDIFGVKGGILSRPLSAIFTT

SEQ
ID  Amino Acid sequence of FN3 domains
NO: that bind to CD71

164 MLPAPKNLVVSRVTEDSARLSWTAPDAAFDSFLIPYAETSPSGEA
    IVLTVPGSERSYDLTGLKPGTEYSVLIHGVKGGHLSDPLSAIFTT

165 MLPARKNLVVSRVTEDSARLSWTAPDAAFDSFFIPYAEPSPTGEA
    IVLTVPGSERSYDLTGLKPGTEYSVLIHGVKGGHLSDPLSAISTT

166 MLPAPKNLVVSRVTEDSARLSWTAPDAAFDSFTILYNEIQNVGEA
    IVLTVPGSERSYDLTGLKPGTEYDVWIEGVKGGELSWPLSAIFTT

167 MLPAPKNLVVSRVTEDSARLSWTAPDAAFDSFFIGYLEPQPPGEA
    IVLTVPGSERSYDLTGLKPGTEYNVTIQGVKGGTPSEPLSAIFTT

168 MLPAPKNLVVSRVTEDSARLSWTTPDAAFDSFFIGYLEPYPPGEA
    IVLTVPGSERSYDLTGLKPGTEYVVSIQGVKGGKPSDPLSAIFTT

169 MLPAPKNLVVSRVTEDSARLSWTAPDAAFDSFFIGYLEPQPPGEA
    IVLTVPGSERSYDLTGLKPGTEYNVTIQGVKGGFPSVPLSAIFTT

170 MLPAPKNLVVSRVTEDSARLSWTAPDAAFDSFFIGYPEYPATGEA
    IVLTVPGSERSYDLTGLKPGTEYFVDINGVKGGSLSYPLSAIFTT

171 MLPAPKNLVVSRVTEDSARLSWTAPDAAFDSFAIRYLEWWDVGEA
    IVLTVPGSERSYDLTGLKPGTEYLVEIKGVKGGKFSYPLSAIFTT

172 MLPAPKNLVVSRVTEDSARLSWTAPDAAFDSFPIEYDEWWALGEA
    ITLIVPASERSYDLTGLKPGTEYVVKIHGVKGGQRSYPLIAFFTT

173 MLPAPKNLVVSRVTEDSARLSWTAPDAAFDSFTIHYRELYVQAIV
    LTVPGSERSYDLTGLKPGTEYLVMIPGVKGGPTSVPLSAIFTT

174 MLPAPKNLVVSRVTEDSARLSWTAPDAAFDSFFIGYLEPQPPGEA
    IVLTVPGSERSYDLTGLKPGTEYKVVIQGVKGGTPSEPLSAIFTT

175 MLPAPKNLVVSRVTEDSARLSWTAPDAAFDSFFIGYLEPQPPGEA
    IVLTVPGSERSYDLTGLKPGTEYSVVIQGVKGGFPSDPLSAIFTT

176 MLPAPKNLVVSRVTEDSARLSWTAPDAAFDSFPIAYAEPRPDGEA
    IVLTVPGSERSYDLTGLKPGTEYSVGIHGVKGGHDSSPLSAIFTT

177 MLPAPKNLVVSRVTEDSARLSWTAPDAAFDSFFIGYLEPQPPGEA
    IVLTVPGSERSYDLTGLKPGTEYNVTIQGVKGGRASGPLSAIFTT

178 MLPAPKNLVVSRVTEDSARLSWTAPDAAFDSFDIAYAEPIPRGEA
    IVLTVPGSERSYDLTGLKPGTEYSVLIHGVKGGRRSVPLSAIFTT

179 MLPAPKNLVVSRVTEDSARLSWTAPDAAFDSFYIAYAEPRPDGEA
    IVLTVPGSERSYDLTGLKPGTEYPVPIPGVKGGPGSSPLSAIFTT

180 MLPAPKNLVVSRVTEDSARLSWTAPDAAFDSFEISYYEMRGYGEA
    IVLTVPGSERSYDLTGLKPGTEYSVLIHGVEGGDYSSPLSAISTT

181 MLPAPKNLVVSHVTEDSARLSWTAPDAAFDSFPIAYAEPRPDGEA
    IVLTVPGSERSYDLTGLKPGTEYSVLIHGVKGGLLSSPLSAIFTT

182 MLPAPKNLVVSRVTEDSARLSWTAPDAAFDSFFIGYLEPYPPGEA
    IVLTVPGSERSYDLTGLKPGTEYVVSIQGVKGGTPSQPLSAIFTT

183 MLPAPKNLVVSRVTEDSARLSWTAPDAAFDSFLIPYAETSPSGEA
    IVLTVPGSERSYDLTGLKPGTEYSVLIHGVKGGRPSNPLVAAFTT

184 MLPAPKNLVVSRITEDSARLSWTAPDAAFDSFGIGYYEHKRFGEA
    IQLSVPGSERSYDLTGLKPGTEYEVDIEGVKGGVLSWPLFAEFTT

185 MLPAPKNLVVSRVTEDSARLSWTAPDAAFDSFEIDYDELAIYGEA
    IVLTVPGSERSYDLTGLKPGTEYGVMIIGVKGGLPSDPLSAIFTT

186 MLPAPKNLVVSRVTEDSARLSWTAPDAAFDSFFIGYLESAEAIVL
    TVPGSERSYDLTGLKPGTEYLVTIQGVKGGIASDPLSAIFTT

187 MLPAPKNLVVSRVTEDSARLSWTAPDAAFDSFVIEYFEFVGYGEA
    IVLTVPGSERSYDLTGLKPGTEYSVGIYGVKGGKLSPPLSAIFTT

188 MLPAPKNLVVSRVTEDSARLSWTAPDAAFDSFLIPYAETSPSGEA
    IVLTVPGSERSYDLTGLKPGTEYSVLIHGVKGGKLSLPLSAIFTT

SEQ
ID  Amino Acid sequence of FN3 domains
NO: that bind to CD71

189 MLPAPKNLVVSRVTEDSARLSWTAPDAAFDSFHEWVYFGEAIVLT
    VPGSERSYDLTGLKPGTEYFVDIWGVKGGTVSKPLSAIFTT

190 MLPAPKNLVVSRVTEDSARLSWTAPDAAFDSFFIGYPEYPATGEA
    ITLFVPGSERSYDLTGLKPGTEYNVVIQGVKGGRPSNPLVVAFTT

191 MLPAPENLVVSRVTEDSARLSWTAPDAAFDSFEITYEENWRRGEA
    IVLTVPGSERSYDLTGPKPGTEYIVIIQGVKGGAESWPLSAIFTT

192 MLPAPKNLVVSRVTEDSARLSWTALDAAFDSFFIGYLEPQPPGEA
    IVLTVPGSERSYDLTGLKPGTEYNVTIQGVKGGFPSMPLSAIFTT

193 MLPAPKNLVVSRVTEDSARLSWTAPDAAFDSFTIWYAEAVGNGEA
    IVLTVPGSERSYDLTGLKPGTEYWVDIWGVKGGEFSSPLSAIFTT

194 MLPAPKNLVVSRVTEDSARLSWTAPDAAFDSFEIDYDELAIYGEA
    IVLTVPGSERSYDLTGLKPGTEYRVFIYGVKGGWTSWPLSTIFTT

195 MLPAPKNLVVSRVTEDSARLSWTAPDAAFDSFPIEYDEIPFWGEA
    IVLTVPGSERSYDLTGLKPGTEYRVWIHGVKGGNSSWPLSAIFTT

196 MLPAPKNLVVSRVTEDSARLSWTAPDAAFDSFNIHYVEWWVLGEA
    IVLTVPGSERSYDLTGLKPGTEYPVYIYGVKGGPKSIPLSAIFTT

197 MLPAPKNLVVSRVTEDSARLSWTAPDAAFDSFKIDYLEINDNGEA
    IVLTVPGSERSYDLTGLKPGTEYPVYIWGVKGGYPSSPLSAIFTT

198 MLPAPKNLVVSRVTEDSARLSWTAPDAAFDSFLIAYNEDRKFGEA
    IVLTVPGSERSYDLTGLKPGTEYDVWIEGVKGGSLSFPLSAIFTT

199 MLPAPKNLVVSRVTEDSARLSWTAPDAAFDSFGIRYFEWWDLGEA
    IVLTVPGSERSYDPTGLKPGTEYNVTIQGVKGGFPSMPLSAIFTT

200 MLPAPKNLVVSRVTEDSARLSWTAPDAAFDSFYIEYYEWMHTGEA
    IVLTVPGSERSYDLTGLKPGTEYSVYIYGVKGGYPSSPLSAIFTT

201 MLPAPKNLVVSRVTEDSARLSWTAPDAAFDSFNIDYWETWVIGEA
    IVLTVPGSERSYDLTGLKPGTEYEVIIPGVKGGTISPPLSAIFTT

202 MLPAPKNLVVSRVTEDSARLSWTAPDAAFDSFYIDYLELTYSGEA
    IVLTVPGSERSYDLTGLKPGTEYYVYIYGVKGGYPSSPLSAIFTT

203 MLPAPKNLVVSRVTEDSARLSWTAPDAALDSFRIEYYESYGHGEA
    IVLTVPGSERSYDLTGLKPGTEYDVGIYGVKGGYYSRPLSAIFTT

204 MLPAPKNLVVSRVTEDSARLPWTAPDAAFDSFWISYYESVGYGEA
    IVLTVPGSERSYDLTGLKPGTEYYVDISGVKGGVYSLPLSAIFTT

205 MLPAPKNLVVSRVTEDSARLSWTAPDAAFDSFDIDYDEPAWNGEA
    IVLTVPGSERSYDLTGLKPGTEYRVFIYGVKGGNTSWPLSAIFTT

206 MLPAPKNLVVSRVTEDSARLSWTAPDAAFDSFDIEYDELWKNGEA
    IVLTVPGSERSYDLTGLKPGTEYRVFIYGVKGGYGSFPLSAIFTT

207 MLPAPKNLVVSRVTEDSARLSWTAPDAAFDSFFIGYLEPQPPGEA
    IVLTVPGSERSYDLTGLKPGTEYNVTIQGVKGGTPSEPLSAISTT

208 MLPAPKNLVVSRVTEDSARLSWTAPDAAFDSFGIVYREPYVGGEA
    IVLTVPGSERSYDLTGLKPGTEYGVPIPGVKGGYDSGPLSAIFTT

209 MLPAPKNLVVSRVTEDSARLSWTAPDAAFDSFTIPYIEYVWWGEA
    IVLTVQGSERSYDLTGLKPGTEYPVTIGGVKGGSRSHPLHAHFTT

210 MLPAPKNLVVSRVTEDSARLSWTAPDAAFDSFSIVYGERFVNGEA
    IVLTVPGSERSYDLTGLKPGTEYHVYIDGVKGGDLSWPLSAIFTT

211 MLPAPKNLVVSRVTEDSARLSWTAPDAAFDSFWINYYEAQPDGEA
    IVLTVPGSERSYDLTGLKPGTEYDVEIAGVKGGTASLPLSAIFTT

212 MLPAPKNLVVSRVTEDSARLSWTAPDAAFDSFIIEYWEQIGVGEA
    IVLTVPGSERSYDLTGLKPGTEYWVGIYGVKGGLLSSPLSAIFTT

213 MLPAPKNLVVSRVTEDSARLSWTAPDAAFDSFWIYYWEIERAGEA
    IRLDVPGSERSYDLTGLKPGTEYRVDIWGVKGGPTSGPLRATFTT

SEQ
ID  Amino Acid sequence of FN3 domains
NO: that bind to CD71

214 MLPAPKNLVVSRVTEDSARLSWTAPDAAFDSFAIPYGERQELGEA
    IVLTVPGSERSYDLTGLKPGTEYFVVIQGVKGGQPSYPLSAIFTT

215 MLPAPKNLVVSRVTEDSARLSWTAPDAAFDSFLIPYAETSPTGEA
    IVLTVPGSERSYDLTGLKPGTEYSVLIHGVKGGYPSSPLSAIFTT

216 MLPAPKNLVVSRVTEDSARLSWTAPDAAFDSFPIAYAEPTPSGEA
    IVLTVPGSERSYDLTGLKPGTEYSVLIHGVKGGGLSLPLSAIFTT

217 MLPAPKNLVVSRVTEDSARLSWTAPDAAFDSFIIEYWEWYFAGEA
    IVLTVPGSERSYDLTGLKPGTEYTVWITGVKGGTWSEPLSAIFTT

218 MLPAPKNLVVSRVTEDSARLSWTAPDAAFDSFTILYYEMVGEGEA
    IVLTVPGSERSYDLTGPKPGTEYWVDIYGVKGGGWSRPLSAIFTT

219 MLPAPKNLVVSRVTEDSARLSWTAPDAAFDSFHIDYLELTYAGEA
    IVLTVPGSERSYDLTGLKPGTEYYVTIYGVKGGYPSSPLSAIFTT

220 MLPAPKNLVVSRVTEDSARLSWTAPDAAFDSFHIIYEEDGTEGEA
    IYLRVPGSERSYDLTGLKPGTEYEVDIEGVKGGVLSWPLFAEFTT

221 MLPAPKNLVVSRVTEDSARLSWTAPDAAFDSFHISYQEVVAEGEA
    IYLRVPGSERSYDLTGLKPGTEYYVLIHGVKGGYESKPLDASFTT

222 MLPAPKNLVVSRVTEDSARLSWTAPDAAFDSFYIEYFEWTGSGEA
    IVLTVPGSERSYDLTGLKPGTEYNVAIYGVKGGAVSYPLSAIFTT

223 MLPAPKNLVVSRVTEDSARLSWTAPDAAFDSFTIWYAEALGDGEA
    IVLTVPGSERSYDLTGLKPGTEYFVDIPGVKGGTRSSPLSAISTT

224 MLLAPKNLVVSRVTEDSARLSWTAPDAAFDSFRYLEQGLYGEAIV
    LTVPGSERSYDLTGLKPGTEYWVEIIGVKGGEYSTPLSAIFTT

225 MLPAPKNLVVSRVTEDSARLSWTAPDAAFDSFKIEYFEYVGYGEA
    IVLTVPGSERSYDLTGLKPGTEYYVAIYGVKGGWYSRPLSAIFTT

226 MLPAPKNLVVSRVTEDSARLSWTAPDAAFDSFHIIYEEVLTEGEA
    IYLRVPGSERSYDLTGLKPGTEYGVTIKGVKGGAYSIPLIATFTT

227 MLPAPKNLVVSRVTEDSARLSWTAPDAAFDSFRIRYLEWWNIGEA
    IVLTVPGSERSYDLTGLKPGTEYHVDIWGVKGGYSSYPLSAIFTT

228 MLPAPKNLVVSRVTEDSARLSWTAPDAAFDSFEIYYVEWSEAGEA
    IVLTVPGSERSYDLTGLKPGTEYRVEIRGVKGGSWSSPLSAIFTT

229 MLPAPKNLVVSRVTEDSARLSWTAPDAAFDSFSIHYDEDWRRGEA
    IVLTVPGSERSYDLTGLKPGTEYLVEIPGVKGGKASYPLSAIFTT

230 MLPAPKNLVVSRVTEDSARLSWTAPDAAFDSFQIRYPKRWISGEA
    IVLTVPGSERSYDLTGLKPGTEYEVVIRGVKGGEYSWPLSAIFTT

231 MLPAPKNLVVSRVTEDSARLSWTAPDAAFDSFEIPYIETVALGEA
    IVLTVPGSERSYDLTGLKPGTEYYVEIYGVKGGSYSYPLSAISTT

232 MLPAPKNLVVSRVTEDSARLSWTAPDAAFDSFTIAYDETLNLGEA
    IVLTVPGSERSYDLTGLKPGTEYIVGIFGVKGGTHSWPLSAIFTT

233 MLPAPKNLVVSRVTEDSARLSWTAPDAAFDSFYIVYAEPIPNGEA
    IVLTVPGSERSYDLTGLKPGTEYSVLIHGVKGGRNSDPLSAIFTT

234 MLPAPKNLVVSRVTEDSARLSWTAPDAAFDSFYITYWETWDYGEA
    IVLTVPGSERSYDLTGLKPGTEYKVPITGVKGGGPSVPLSAIFTT

235 MLPAPKNLVVSRVTEDSARLSWTAPDAAFDSFSINYREWWSDGEA
    IYLPVPGSERSYDLTGLKPGTEYAVYIQGVKGGSRSFPLHAWFTT

236 MLPAPKNLVVSRVTEDSARLSWTAPDAAFDSFWIEYYEELGSGEA
    IVLTVPGSERSYDLTGLKPGTEYRVYIYGVKGGYPSSPLSAIFTT

237 MLPAPKNLVVSRVTEDSARLSWTAPDAAFDSFTILYGEMGTTGEA
    IVLTVPGSERSYDLTGLKPGTEYDVFIEGVKGGELSWPLSAIFTT

238 MLPAPKNLVVSRVTEDSARLSWTAPDAAFDSFKIFYQEFGGEAIV
    LTVPGSERSYDLTGLKPGTEYWVDIYGVKGGYTSSPLSAIFTT

SEQ
ID  Amino Acid sequence of FN3 domains
NO: that bind to CD71

239 MLPAPKNLVVSRVTEDSARLSWTAPDAAFDSFAITYYEGRWRGEA
    IVLTVPGSERSYDLTGLKPGTEYGVPIRGVKGGTGSLPLSAIFTT

240 MLPAPKNLVVSRVTEDSARLSWTAPDAAFDSFRIKYLEWWLGGEA
    IVLTVPGSERSYDLTGLKPGTEYWVDIQGVKGGVLSWPLSAIFTT

241 MLPAPKNLVVSRVTEDSARLSWTAPDAAFDSFNIYYYEWFVSGEA
    IVLTVPGSERSYDLTGLKPGTEYFVDIDGVKGGYRSRPLSAIFTT

242 MLPAPKNLVVSRVTEDSARLSWTAPDAAFDSFPIKYLEWWSWGEA
    IVLTVPGSERSYDLTGLKPGTEYRVPISGVKGGGMSGPLSAIFIT

243 MLPAPKNLVVSRVTEDSARLSWTAPDAAFDSFAIPYYEWVNHGEA
    IVLTVPGSERSYDLTGLKPGTEYPVGIDGVKGGGPSWPLSAIFIT

244 MLPAPKNLVVSRVTEDSARLSWTAPDAAFDSFHIDYSEFHLRGEA
    IVLTVPGSERSYDLTGLKPGTEYLGIFGVKGGEQSGPLSAIFTT

245 MLPAPKNLVVSRITEDSARLSWTAPDAAFDSFGIAYNEGDHYGEA
    IVLTVPGSERSYDLTGLKPGTEYSVWIEGVKGGNLSYPLSAIFTT

246 MLPAPKNLVVSRVTEDSARLSWTAPDAAFDSFTIAYNEQNHYGEA
    IVLTVPGSERSYDLTGLKPGTEYGVWIEGVKGGTLSWPLSAIFIT

247 MLPAPKNLVVSRVTEDSARLSWTAPDAAFDSFYIEWTYKGEAIVL
    TVPGSERSYDLTGLKPGTEYFVGIPGVKGGKSSYPLSAIFTTNPK
    GDTP

248 MGSLPAPKNLVVSRVTEDSARLSWTAPDAAFDSFAIPYAEPSPTG
    EAIVLTVPGSERSYDLTGLKPGTEYPVWIQGVKGGSPSAPLSAEF
    TT

249 MLPAPKNLVVSRVTEDSARLSWTAPDAAFDSFSIDYFESVGFGEA
    IVLTVPGSERSYDLTGLKPGTEYDVQITGVKGGPHSLPLSAIFTT

250 MLPAPKNLVVSRVTEDSARLSWTAPDAAFDSFFIGYLEPYPPGEA
    IVLTVPGSERSYDLTGLKPGTEYAVEIAGVKGGLLSSPLSAISTT

251 MLPAPKNLVVSRVTEDSARLSWTAPDAAFDSFFIGYLEPQPPGEA
    IVLTVPGSERSYDLTGLKPGTEYNVTIQGVKGGFPSMPLSAIVTT

252 MLPAPKNLVVSRVTEDSARLSWTAPDAAFDSFDIGYTEYGGYGEA
    IVLTVPGSERSYDLTGLKPGTEYWVLIQGVKGGGSSVPLSAIFTT

253 MLPAPKNLVVSRVTEDSARLSWTAPDAAFDSFTIEYWETIGGGEA
    IVLTVPGSERSYDLTGLKPGTEYYVGIYGVKGGWWSRPLSAIFIT

254 MLPAPKNLVVSRVTEDSARLSWTAPDAAFDSFFIPYAEPSPTGEA
    IVLTVPGSERSYDLTGLKPGTEYSVLIHGVKGGHLSDPLSAISTT

255 MLPAPKNLVVSRVTEDSARLSWTAPDAAFDSFDIEYYELIGRGEA
    IVLTVPGSERSYDLTGLKPGTEYWVGIYGVKGGWLSRPLSAIFTT

256 MLPAPKNLVVSRVTEDSARLSWTAPDAAFDSFHIVYHEPRPSGEA
    IVLTVPGSERSYDLTGLKPGTEYEVGIVGVKGGDLSVPLSAIFTT

257 MLPAPKNLVVSRVTEDSARLSWTAPDAAFDSFHIVYHEPRPSGEA
    IVLTVPGSERSYDLTGLKPGTEYEVGIVSVKGGDLSVPLSAIFTT

258 MLPAPKNLVVSRVTEDSARLSWTAPDAAFDSFFIPYAEPSPTGEA
    IVLTVPGSERSYDLTGLKPGTEYDVWIEGVKGGVLSWPLSAIFTT

259 MLPAPKNLVVSRVTEDSARLSWTAPDAAFDSFTIEYFEFVDAGEA
    IVLTVPGSERSYDLTGLKPGTEYWVEIWGVKGGSWSKPLSAIFTT

260 MLPAPKNLVVSRVTEDSARLSWTAPDAAFDSFNISYYEYFVHGEA
    IVLTVPGSERSYDLTGLKPGTEYYVIDGVKGGDPSEPLSAIFTT

261 MLPAPKNLVVSRVTEDSARLSWTAPDAAFDSFTIVYGEWGVPGEA
    IVLTVPGSERSYDLTGLKPGTEYDVWIEGVKGGDLSWPLSAIVTT

262 MLPAPKNLVVSRVTEDSARLSWTAPDAAFDSFAIEYFEYTGEGEA
    IVLTVPGSERSYDLTGLKPGTEYYVGIYGVKGGYLSRPLSAIFTT

-continued

```
SEQ
 ID  Amino Acid sequence of FN3 domains
NO:  that bind to CD71

263  MLPAPKNLVVSRVTEDSARLSWTAPDAAFDSFFIGYLEPQPPGEA
     IVLTVPGSERSYDLTGLKPGTEYNVTIQGVKGGFPSMPLSAISTT

264  MLPAPKNLVVSRVTEDSARLSWTAPDAAFDSFRIKYQEWWVEGEA
     IVLTVPGSERSYDLTGLKPGTEYVVQIAGVKGGLSSYPLSAIFIT

265  MLPAPKNLVVSRVTEDSARLSWTAPDAAFDSFWIYYIETSHQGEA
     IVLTVPGSERSYDLTGLKPGTEYFVLIKGVKGGYDSVPLSAIFTT

266  MLPAPKNLVVSRVTEDSARLSWTAPDAAFDSFMIRYQEGTRWGEA
     IVLTVPGSERSYDLTGLKPGTEYIVMIAGVKGGQISLPLSAIFTT

267  MLPAPKNLVVSRVTEDSARLSWTAPDAAFDSFPIVYSEIHVIGEA
     IVLTVPGSERSYDLTGLKPGTEYDVWIEGVKGGHLSEPLSAIFTT

268  MLPAPKNLVVSRVTEDSARLSWTAPDAAFDSFTIVYGEAGAFGEA
     IVLTVPGSERSYDLTGLKPGTEYDVLIEGVKGGNLSWPLSAIFTT

269  MLPAPKNLVVSRVTEDSARLSWTAPDAAFDSFHINYAEVYTKGEA
     ILLTVPGSERSYDLTGLKPGTEYEVYIPGVKGGPFSRPLNAQFTT

270  MLPAPKNLVVSRVTEDSARLSWTAPDAAFDSFLIRYQEWQRWGEA
     IVLTVPGSERSYDLTGLKPGTEYTVHIAGVKGGMLSLPLSAIFTT

271  MLPAPKNLVVSRVTEDSARLSWTAPDAAFDSFYIPYAETRDDGEA
     IVLTVPGSERSYDLTGLKPGTEYSVLIHGVKGGDLSSPLSAIFTT

272  MLPAPKNLVVSRVTEDSARLSWTAPDAAFDSFGIPYAESTPTGEA
     IVLTVPGSERSYDLTGLKPGTEYSVLIHGVKGGHLSDPLSAIFTT

273  MLPAPKNLVVSRVTEDSARLSWTAPDAAFDSFTIFKDGEAIVLTV
     PGSERSYDLTGLKPGTEYYVYIYGVKGGYPSKPLSAIFTT

274  MLPAPKNLVVSRVTEDSVRLSWTAPDAAFDSFAISYEEWWVHGEA
     IVLTVPGSERSYDLTGLKPGTEYSVVIPGVKGGLYSWTLSAISTT

275  MLPAPKNLVVSRVTEDSARLSWTAPDAAFDSFLIAYAEVTLHGEA
     IVLTVPGSERSYDLTGLKPGTEYSVLIHGVKGGRNSDPLSAIFTT

276  MLPAPKNLVVSRVTEDSARLSWTAPDAAFDSFRIDYLELTSLGEA
     IVLTVPGSERSYDLTGLKPGTEYPVPILGVKGGLSSWPLSAIFTT

277  MLPAPKNLVVSRVTEDSARLSWTAPDAAFDSFWINYYEGIGEGEA
     IVLTVPGSERSYDLTGLKPGTEYYVDISGVKGGSYSLPLSAIFTT

278  MLPAPKNLVVSRVTEDSARLSWTAPDAAFDSFPIAYAEPRPDGEA
     IVLTVPGSERSYDLTGLKPGTEYSVLIHGVKGGHLSDPLSAIFTT

279  MLPAPKNLVVSRVTEDSARLSWTAPDAAFDSFSIEYYESVGLGEA
     IVLTVPGSERSYDLTGLKPGTEYDVSIYGVKGGYLSRPLSAIFIT

280  MLPAPKNLVVRXVTEDSARLSWTAPDAAFDSFEIEYDEPYRGGEA
     IVLTVPGSERSYDLTSLKPGTEYPVSIGGVKGGITSDPLSAIFTT

281  MLPAPKNLVVSRVTEDSARLSWTAPDAAFDSFYIDYDEIHDWGEA
     IVLTVPGSERSYDLTGLKPGTEYAVQIGGVKGGSFSWILSAIFTT

282  MLPAPKNLVVSRVTEDSARLSWTAPDAAFDSFAIVYHEPRPDGEA
     IVLTVPGSERSYDLTGLKPGTEYEVVILGVKGGVHSYPLSAIFTT

283  MLPAPKNLVVSRVTEDSARLSWTAPDAAFDSFPIAYAEPRPDGEA
     IVLTVPGSERSYDLTGLKPGTEYSVLIHGVKGGLLSSPLSAIFTT

284  MLPAPKNLVVSRVTEDSARLSWTAPDAAFDSFFIGYLEPQPPGEA
     IVLTVPGSERSYDLTGLKPGTEYNVTIQGVKGGFPSMPLSAIFTT

285  MLPAPKNLVVSRVTEDSARLSWTAPDAAFDSFLIPYAETSPSGEA
     IVLTVPGSERSYDLTGLKPGTEYSVLIHGVKGGDYSSPLSAIFIT

286  MLPAPKNLVVSRVTEDSARLSWTAPDAAFDSFNIYYPEFPVRGEA
     IVLTVPGSERSYDLTGLKPGTEYVVSIWGVKGGTQSWPLSAIFTT

287  MLPAPKNLVVSRVTEDSARLSWTAPDAAFDSFTIEYHESGPVGEA
     IVLTVPGSERSYDLTGLKPGTEYMVWIFGVKGGFVSRPLSAIFTT
```

-continued

```
SEQ
 ID  Amino Acid sequence of FN3 domains
NO:  that bind to CD71

288  MLPAPKNLVVSRVTEDSARLSWTAPDAAFDSFLIPYAETSPSGEA
     IVLTVPGSERSYDLTGLKPGTEYSVLIHGVKGGDYSSPLSAISTT

289  MLPAPKNLVVSRVTEDSARLSWTAPDAAFDSFAIPYYEDTNDGEA
     IVLTVPGSERSYDLTGLKPGTEYWVSIQGVKGGTVSGPLSAIFTT

290  MLPAPKNLVVSRVTEDSARLSWTAPDAAFDSFFYLEQAWGGEAIV
     LTVPGSERSYDLTGLKPGTEYWVEITGVKGGYASSPLSAIFTT

291  MLPAPKNLVVSRVTEDSARLSWTAPDAAFDSFHIEYEEPETEGEA
     IYLHVPGSERSYDLTGLKPGTEYKVLIRGVKGGSYSIPLQAPFTT

292  MLPAPKNLVVSRVTEDSARLSWTAPDAAFDSFDIAYWELTPSGEA
     IELLVPGSERSYDLTGLKPGTEYRVDIIGVKGGFISEPLGATFTT

293  MLPAPKNLVVSRVTEDSARLSWTAPDAAFDSFTIEYWEFTGSGEA
     IVLTVPGSERSYDLTGLKPGTEYDVSIYGVKGGWLSYPLSAIFTT

294  MLPAPKNLVVSRVTEDSARLSWTAPDAAFDSFSIIYSEWNVTGEA
     IVLTVPGSERSYDLTGLKPGTEYDVWIEGVKGGGMSKPLSAISTT

295  MLPAPKNLVVSRVTEDSARLSWTAPDAAFDSFFIGYLEPIPSGEA
     IVLTVPGSERSYDLTGLKPGTEYPVVIQGVKGGHPSQPLSAIFIT

296  MLPAPKNLVVSRVTEDSARLSWTAPDAAFDSFFIGYLEPQPPGEA
     IILTVPGSERSYDLTGLKPGTEYNVTIQGVKGGFPSMPLSAIFTT

297  MLPAPKNLVVSRVTEDSARLSWTAPDAAFDSFLIPYAETSPSGEA
     ITLFVPGSERSYDLTGLKPGTEYNVVIQGVKGGRPSNPLVAASTT

298  MLPAPKNLVVSRVTEDSARLSWTAPDAAFDSFPIAYAEPRPDGEA
     IVLTVPGSERSYDLTGLKPGTEYSVLIHGVKGGLLSSPLSAISTT

299  MLPAPKNLVVSRVTEDSARLSWTAPDAAFDSFLIEYWESVGYGEA
     IVLTVPGSERSYDLTGLKPGTEYWVGIYGVKGGYYSRPLSAIFTT

300  MLPAPKNLVVSRVTEDSARLSWTAPDAAFDSFFIGYLEPQPPGEA
     IVLTVPGSERSYDLTGLKPGTEYNVTIHGVKGGTPSMPLSAIFTT

301  MLPAPKNLVVSRVTEDSARLSWTAPDAAFDSFEIEYDEPYRGGEA
     IVLTVPGSERSYDLTSLKPGTEYPVSIGGVKGGITSDPLSAIFTT

302  MLPAPKNLVVSRVTEDSARLSWTAPDAAFDSFDIYYPEYYDRGEA
     IVLTVPGSERSYDLTGLKPGTEYTVYIDGVKGGGGSGPLSAIFTT

303  MLPAPKNLVVSRVTEDSARLSWTAPDAAFDSFFIAYFEFANPGEA
     IVLTVPGSERSYDLTGLKPGTEYKVVIQGVKGGTPSEPLSAIFTT

304  MLPAPKNLVVSRVTEDSARLSWTAPDAAFDSFIITYWEHVGDGEA
     IVLTVPGSERSYDLTGLKPGTEYFVEIYGVKGGYLSKPLSAIFTT

305  MLPAPKNLVVSRVTEDSARLSWTAPDAAFDSFEIDYDEPFVYGEA
     IVLTVPGSERSYDLTGLKPGTEYRVFIFGVKGGNGSWPLSAIFTT

306  MLPAPKNLVVSRVTEDSARLSWTAPDAAFDSFYIEYFETQGYGEA
     IVLTVPGSERSYDLTGLKPGTEYYVAIYGVKGGYLSRPLSAIFTT

307  MLPAPKNLVVSRVTEDSARLSWTAPDAAFDSFPITYSEPAHYGEA
     IVLTVPGSERSYDLTGLKPGTEYHVGIMGVKGGVFSSPLSAIFTT

308  MLPAPKNLVVSEVTEDSARLSWQGVARAFDSFLITYREQIFAGEV
     IVLTVPGSERSYDLTGLKPGTEYPVWIQGVKGGSPSAPLSAISTT

309  MLPAPKNLVVSRVTEDSARLSWTAPDAAFDSFIIDYLELDQEGEA
     IVLTVPGSERSYDLTGLKPGTEYAVYIFGVKGGYPSTPLSAIFTT
```

Example 6. Knockdown of mRNA in muscle cells using CD71 FN3 domain-oligonucleotide conjugates. muCD71 binding FN3 domains are conjugated to siRNA oligonucleotides or antisense oligonucleotides (ASOs) using maleimide chemistry via a cysteine that is uniquely engineered into the FN3 domain. The cysteine substitutions can be one such as those provided for herein and also as provided for in U.S. Patent Application Publication No. 20150104808, which is hereby incorporated by reference in its entirety. siRNAs or ASOs are modified with standard chemical modifications and confirmed to enable knockdown of the targeted mRNA in vitro. FN3 domain-oligonucleotide conjugates are dosed intravenously in mice at doses up to 10 mg/kg oligonucleotide payload. At various time points following dosing, mice are sacrificed; skeletal muscle, heart muscle and various other tissues will be recovered and stored in RNAlater™ (Sigma Aldrich) until needed. Target gene knockdown is assessed using standard qPCR $\Delta\Delta C_T$ methods and primers specific for the target gene and a control gene.

The target gene is found to be knock downed in the muscles and such knockdown is enhanced by conjugating the siRNA or ASO to the CD71 FN3 binding domain.

Example 7. GENERAL METHODS

Standard methods in molecular biology are described Sambrook, Fritsch and Maniatis (1982 & 1989 2nd Edition, 2001 3rd Edition) *Molecular Cloning, A Laboratory Manual*, Cold Spring Harbor Laboratory Press, Cold Spring Harbor, NY: Sambrook and Russell (2001) *Molecular Cloning.* 3rd ed., Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology, Vols.* 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17: Sigma-Aldrich, Co. (2001) *Products for*

*Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) Using Antibodies, Cold Spring Harbor Laboratory Press, Cold Spring Harbor, NY: Harlow and Lane, supra). Standard techniques for characterizing ligand/receptor interactions are available (see, e.g., Coligan, et al. (2001) *Current Protocols in Immunology, Vol.* 4, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57 (b) (1), to relate to each and every individual publication, database entry (e.g. Genbank sequences or GeneID entries), patent application, or patent, each of which is clearly identified in compliance with 37 C.F.R. § 1.57 (b) (2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications of the embodiments in addition to those described herein will become apparent to those skilled in the art from the foregoing description. Such modifications are intended to fall within the scope of the appended claims.

The foregoing written specification is considered to be sufficient to enable one skilled in the art to practice the embodiments. Various modifications of the embodiments in addition to those shown and described herein will become apparent to those skilled in the art from the foregoing description and fall within the scope of the appended claims.

```
                          SEQUENCE LISTING

Sequence total quantity: 310
SEQ ID NO: 1           moltype = AA  length = 89
FEATURE                Location/Qualifiers
source                 1..89
                       mol_type = protein
                       organism = Homo sapiens
SEQUENCE: 1
LPAPKNLVVS EVTEDSLRLS WTAPDAAFDS FLIQYQESEK VGEAINLTVP GSERSYDLTG  60
LKPGTEYTVS IYGVKGGHRS NPLSAEFTT                                    89

SEQ ID NO: 2           moltype = AA  length = 94
FEATURE                Location/Qualifiers
VARIANT                75..81
                       note = X is any amino acid
VARIANT                82..86
                       note = X is any amino acid or deleted
source                 1..94
                       mol_type = protein
                       organism = synthetic construct
SEQUENCE: 2
LPAPKNLVVS EVTEDSLRLS WTAPDAAFDS FLIQYQESEK VGEAINLTVP GSERSYDLTG  60
LKPGTEYTVS IYGVXXXXXX XXXXXXPLSA EFTT                              94
```

-continued

```
SEQ ID NO: 3            moltype = AA   length = 89
FEATURE                 Location/Qualifiers
VARIANT                 22..27
                        note = each X is Ala, Arg, Asn, Asp, Glu, Gln, Gly, His,
                        Ile, Leu, Lys, Phe, Pro, Ser, Thr, Trp, Tyr or Val
VARIANT                 28
                        note = X is Phe, Ile, Leu, Val or Tyr
VARIANT                 29
                        note = X is Asp, Glu or Thr
VARIANT                 75..79
                        note = each X is Ala, Arg, Asn, Asp, Glu, Gln, Gly, His,
                        Ile, Leu, Lys, Phe, Pro, Ser, Thr, Trp, Tyr or Val
VARIANT                 81..82
                        note = each X is Ala, Arg, Asn, Asp, Glu, Gln, Gly, His,
                        Ile, Leu, Lys, Phe, Pro, Ser, Thr, Trp, Tyr or Val
source                  1..89
                        mol_type = protein
                        organism = synthetic construct
SEQUENCE: 3
LPAPKNLVVS EVTEDSLRLS WXXXXXXXXS FLIQYQESEK VGEAINLTVP GSERSYDLTG   60
LKPGTEYTVS IYGVXXXXXS XXLSAEFTT                                     89

SEQ ID NO: 4            moltype = AA   length = 89
FEATURE                 Location/Qualifiers
source                  1..89
                        mol_type = protein
                        organism = synthetic construct
SEQUENCE: 4
LPAPKNLVVS RVTEDSARLS WTAPDAAFDS FLIQYQESEK VGEAIVLTVP GSERSYDLTG   60
LKPGTEYTVS IYGVKGGHRS NPLSAIFTT                                     89

SEQ ID NO: 5            moltype = AA   length = 97
FEATURE                 Location/Qualifiers
VARIANT                 22..27
                        note = each X is A, D, E, F, G, H, I, K, L, N, P, Q, R, S,
                        T, V, W or Y
VARIANT                 28..30
                        note = each X is A, D, E, F, G, H, I, K, L, N, P, Q, R, S,
                        T, V, W, Y or deleted
VARIANT                 78..84
                        note = each X is A, D, E, F, G, H, I, K, L, N, P, Q, R, S,
                        T, V, W or Y
VARIANT                 85..87
                        note = each X is A, D, E, F, G, H, I, K, L, N, P, Q, R, S,
                        T, V, W, Y or deleted
source                  1..97
                        mol_type = protein
                        organism = synthetic construct
SEQUENCE: 5
LPAPKNLVVS RVTEDSARLS WXXXXXXXXX FDSFLIQYQE SEKVGEAIVL TVPGSERSYD   60
LTGLKPGTEY TVSIYGVXXX XXXXXXXSNP LSAIFTT                            97

SEQ ID NO: 6            moltype = AA   length = 96
FEATURE                 Location/Qualifiers
VARIANT                 75..81
                        note = each X is A, D, E, F, G, H, I, K, L, N, P, Q, R, S,
                        T, V, W or Y
VARIANT                 82..86
                        note = each X is A, D, E, F, G, H, I, K, L, N, P, Q, R, S,
                        T, V, W, Y or deleted
source                  1..96
                        mol_type = protein
                        organism = synthetic construct
SEQUENCE: 6
LPAPKNLVVS RVTEDSARLS WTAPDAAFDS FLIQYQESEK VGEAIVLTVP GSERSYDLTG   60
LKPGTEYTVS IYGVXXXXXX XXXXXSNPL SAIFTT                              96

SEQ ID NO: 7            moltype = AA   length = 89
FEATURE                 Location/Qualifiers
VARIANT                 32
                        note = X is A, D, E, F, G, H, I, K, L, N, P, Q, R, S, T, V,
                        W,Y, C or M
VARIANT                 34
                        note = X is A, D, E, F, G, H, I, K, L, N, P, Q, R, S, T, V,
                        W,Y, C or M
VARIANT                 36
                        note = X is A, D, E, F, G, H, I, K, L, N, P, Q, R, S, T, V,
                        W,Y, C or M
VARIANT                 38..41
```

```
                        note = X is A, D, E, F, G, H, I, K, L, N, P, Q, R, S, T, V,
                        W,Y, C or M
VARIANT                 68
                        note = X is A, D, E, F, G, H, I, K, L, N, P, Q, R, S, T, V,
                        W,Y, C or M
VARIANT                 70
                        note = X is A, D, E, F, G, H, I, K, L, N, P, Q, R, S, T, V,
                        W,Y, C or M
VARIANT                 72
                        note = X is A, D, E, F, G, H, I, K, L, N, P, Q, R, S, T, V,
                        W,Y, C or M
VARIANT                 78..79
                        note = X is A, D, E, F, G, H, I, K, L, N, P, Q, R, S, T, V,
                        W,Y, C or M
VARIANT                 81
                        note = X is A, D, E, F, G, H, I, K, L, N, P, Q, R, S, T, V,
                        W,Y, C or M
source                  1..89
                        mol_type = protein
                        organism = synthetic construct
SEQUENCE: 7
LPAPKNLVVS RVTEDSARLS WTAPDAAFDS FXIXYXEXXX XGEAIVLTVP GSERSYDLTG  60
LKPGTEYXVX IXGVKGGXXS XPLSAIFTT                                   89

SEQ ID NO: 8            moltype = AA  length = 89
FEATURE                 Location/Qualifiers
VARIANT                 32
                        note = X is A, D, E, F, G, H, I, K, L, N, P, Q, R, S, T, V,
                        Y or W
VARIANT                 34
                        note = X is A, D, E, F, G, H, I, K, L, N, P, Q, R, S, T, V,
                        Y or W
VARIANT                 36
                        note = X is A, D, E, F, G, H, I, K, L, N, P, Q, R, S, T, V,
                        Y or W
VARIANT                 38..41
                        note = X is A, D, E, F, G, H, I, K, L, N, P, Q, R, S, T, V,
                        Y or W
VARIANT                 46
                        note = X is A, D, E, F, G, H, I, K, L, N, P, Q, R, S, T, V,
                        Y or W
VARIANT                 48
                        note = X is A, D, E, F, G, H, I, K, L, N, P, Q, R, S, T, V,
                        Y or W
VARIANT                 68
                        note = X is A, D, E, F, G, H, I, K, L, N, P, Q, R, S, T, V,
                        Y or W
VARIANT                 70
                        note = X is A, D, E, F, G, H, I, K, L, N, P, Q, R, S, T, V,
                        Y or W
VARIANT                 72
                        note = X is A, D, E, F, G, H, I, K, L, N, P, Q, R, S, T, V,
                        Y or W
VARIANT                 78..79
                        note = X is A, D, E, F, G, H, I, K, L, N, P, Q, R, S, T, V,
                        Y or W
VARIANT                 81
                        note = X is A, D, E, F, G, H, I, K, L, N, P, Q, R, S, T, V,
                        Y or W
VARIANT                 84
                        note = X is A, D, E, F, G, H, I, K, L, N, P, Q, R, S, T, V,
                        Y or W
VARIANT                 86
                        note = X is A, D, E, F, G, H, I, K, L, N, P, Q, R, S, T, V,
                        Y or W
source                  1..89
                        mol_type = protein
                        organism = synthetic construct
SEQUENCE: 8
LPAPKNLVVS RVTEDSARLS WTAPDAAFDS FXIXYXEXXX XGEAIXLXVP GSERSYDLTG  60
LKPGTEYXVX IXGVKGGXXS XPLXAXFTT                                   89

SEQ ID NO: 9            moltype = DNA  length = 19
FEATURE                 Location/Qualifiers
source                  1..19
                        mol_type = other DNA
                        organism = synthetic construct
SEQUENCE: 9
gtgacacggc ggttagaac                                             19
```

-continued

```
SEQ ID NO: 10            moltype = DNA   length = 20
FEATURE                  Location/Qualifiers
source                   1..20
                         mol_type = other DNA
                         organism = synthetic construct
SEQUENCE: 10
gcctttggga agcttctaag                                            20

SEQ ID NO: 11            moltype = DNA   length = 30
FEATURE                  Location/Qualifiers
source                   1..30
                         mol_type = other DNA
                         organism = synthetic construct
SEQUENCE: 11
cggcggttag aacgcggcta caattaatac                                 30

SEQ ID NO: 12            moltype = DNA   length = 22
FEATURE                  Location/Qualifiers
source                   1..22
                         mol_type = other DNA
                         organism = synthetic construct
SEQUENCE: 12
catgattacg ccaagctcag aa                                         22

SEQ ID NO: 13            moltype = DNA   length = 385
FEATURE                  Location/Qualifiers
misc_difference          198..224
                         note = n is any base
source                   1..385
                         mol_type = other DNA
                         organism = synthetic construct
SEQUENCE: 13
gtgacacggc ggttagaacg cggctacaat taatacataa ccccatcccc ctgttgacaa  60
ttaatcatcg gctcgtataa tgtgtggaat tgtgagcgga taacaatttc acacaggaaa 120
caggatctac catgctgccg gcgccgaaaa acctggttgt ttctgaagtt accgaagact 180
ctctgcgtct gtcttggnnn nnnnnnnnnn nnnnnnnnnn nnnnttygac tctttcctga 240
tccagtacca ggaatctgaa aaagttggtg aagcgatcaa cctgaccgtt ccgggttctg 300
aacgttctta cgacctgacc ggtctgaaac cgggtaccga atacaccgtt tctatctacg 360
gtgttcttag aagcttccca aaggc                                      385

SEQ ID NO: 14            moltype = DNA   length = 382
FEATURE                  Location/Qualifiers
misc_difference          198..221
                         note = n is any base
source                   1..382
                         mol_type = other DNA
                         organism = synthetic construct
SEQUENCE: 14
gtgacacggc ggttagaacg cggctacaat taatacataa ccccatcccc ctgttgacaa  60
ttaatcatcg gctcgtataa tgtgtggaat tgtgagcgga taacaatttc acacaggaaa 120
caggatctac catgctgccg gcgccgaaaa acctggttgt ttctgaagtt accgaagact 180
ctctgcgtct gtcttggnnn nnnnnnnnnn nnnnnnnnnn nttygactct ttcctgatcc 240
agtaccagga atctgaaaaa gttggtgaag cgatcaacct gaccgttccg ggttctgaac 300
gttcttacga cctgaccggt ctgaaaccgg gtaccgaata caccgtttct atctacggtg 360
ttcttagaag cttcccaaag gc                                         382

SEQ ID NO: 15            moltype = DNA   length = 379
FEATURE                  Location/Qualifiers
misc_difference          198..218
                         note = n is any base
source                   1..379
                         mol_type = other DNA
                         organism = synthetic construct
SEQUENCE: 15
gtgacacggc ggttagaacg cggctacaat taatacataa ccccatcccc ctgttgacaa  60
ttaatcatcg gctcgtataa tgtgtggaat tgtgagcgga taacaatttc acacaggaaa 120
caggatctac catgctgccg gcgccgaaaa acctggttgt ttctgaagtt accgaagact 180
ctctgcgtct gtcttggnnn nnnnnnnnnn nnnnnnnntt ygactcttct ctgatccagt 240
accaggaatc tgaaaaagtt ggtgaagcga tcaacctgac cgttccgggt tctgaacgtt 300
cttacgacct gaccggtctg aaaccgggta ccgaatacac cgtttctatc tacggtgttc 360
ttagaagctt cccaaaggc                                             379

SEQ ID NO: 16            moltype = DNA   length = 376
FEATURE                  Location/Qualifiers
misc_difference          198..215
                         note = n is any base
source                   1..376
                         mol_type = other DNA
```

```
                          organism = synthetic construct
SEQUENCE: 16
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnnn nnnnnttyga ctctttcctg atccagtacc   240
aggaatctga aaaagttggt gaagcgatca acctgaccgt tccgggttct gaacgttctt   300
acgacctgac cggtctgaaa ccgggtaccg aatacaccgt ttctatctac ggtgttctta   360
gaagcttccc aaaggc                                                   376

SEQ ID NO: 17           moltype = DNA   length = 131
FEATURE                 Location/Qualifiers
source                  1..131
                        mol_type = other DNA
                        organism = synthetic construct
SEQUENCE: 17
cggcggttag aacgcggcta caattaatac ataaccccat cccctgttg acaattaatc    60
atcggctcgt ataatgtgtg gaattgtgag cggataacaa tttcacacag gaaacaggat   120
ctaccatgct g                                                        131

SEQ ID NO: 18           moltype = DNA   length = 30
FEATURE                 Location/Qualifiers
source                  1..30
                        mol_type = other DNA
                        organism = synthetic construct
SEQUENCE: 18
cggcggttag aacgcggcta caattaatac                                     30

SEQ ID NO: 19           moltype = DNA   length = 81
FEATURE                 Location/Qualifiers
source                  1..81
                        mol_type = other DNA
                        organism = synthetic construct
SEQUENCE: 19
ccaagacaga cgggcagagt cttcggtaac gcgagaaaca accaggtttt tcggcgccgg    60
cagcatggta gatcctgttt c                                              81

SEQ ID NO: 20           moltype = DNA   length = 26
FEATURE                 Location/Qualifiers
source                  1..26
                        mol_type = other DNA
                        organism = synthetic construct
SEQUENCE: 20
ccgaagactc tgcccgtctg tcttgg                                         26

SEQ ID NO: 21           moltype = DNA   length = 45
FEATURE                 Location/Qualifiers
source                  1..45
                        mol_type = other DNA
                        organism = synthetic construct
SEQUENCE: 21
cagtggtctc acggattcct ggtactggat caggaaagag tcgaa                    45

SEQ ID NO: 22           moltype = DNA   length = 54
FEATURE                 Location/Qualifiers
source                  1..54
                        mol_type = other DNA
                        organism = synthetic construct
SEQUENCE: 22
catgcggtct cttccgaaaa agttggtgaa gcgatcgtcc tgaccgttcc gggt          54

SEQ ID NO: 23           moltype = DNA   length = 29
FEATURE                 Location/Qualifiers
source                  1..29
                        mol_type = other DNA
                        organism = synthetic construct
SEQUENCE: 23
ggtggtgaag atcgcagaca gcgggttag                                      29

SEQ ID NO: 24           moltype = DNA   length = 21
FEATURE                 Location/Qualifiers
source                  1..21
                        mol_type = other DNA
                        organism = synthetic construct
SEQUENCE: 24
cggcggttag aacgcggcta c                                              21

SEQ ID NO: 25           moltype = DNA   length = 61
FEATURE                 Location/Qualifiers
```

-continued

```
source                   1..61
                         mol_type = other DNA
                         organism = synthetic construct
SEQUENCE: 25
aagatcagtt gcggccgcta gactagaacc gctgccaccg ccggtggtga agatcgcaga   60
c                                                                   61

SEQ ID NO: 26            moltype = DNA  length = 485
FEATURE                  Location/Qualifiers
misc_difference          357..392
                         note = n is any base
source                   1..485
                         mol_type = other DNA
                         organism = synthetic construct
SEQUENCE: 26
gtgacacggc ggttagaacg cggctacaat taatacataa ccccatcccc ctgttgacaa   60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnn nnnnnnnnnn nnnnnnnnnn nntctaaccc gctgtctgcg atcttcacca  420
ccggcggtca ccatcaccat caccatggca gcggttctag tctagcggcc gcaactgatc  480
ttggc                                                              485

SEQ ID NO: 27            moltype = DNA  length = 482
FEATURE                  Location/Qualifiers
misc_difference          357..389
                         note = n is any base
source                   1..482
                         mol_type = other DNA
                         organism = synthetic construct
SEQUENCE: 27
gtgacacggc ggttagaacg cggctacaat taatacataa ccccatcccc ctgttgacaa   60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnnnnnnnnt ctaacccgct gtctgcgatc ttcaccaccg  420
gcggtcacca tcaccatcac catggcagcg gttctagtct agcggccgca actgatcttg  480
gc                                                                 482

SEQ ID NO: 28            moltype = DNA  length = 479
FEATURE                  Location/Qualifiers
misc_difference          357..386
                         note = n is any base
source                   1..479
                         mol_type = other DNA
                         organism = synthetic construct
SEQUENCE: 28
gtgacacggc ggttagaacg cggctacaat taatacataa ccccatcccc ctgttgacaa   60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnnnntcta acccgctgtc tgcgatcttc accaccggcg  420
gtcaccatca ccatcaccat ggcagcggtt ctagtctagc ggccgcaact gatcttggc  479

SEQ ID NO: 29            moltype = DNA  length = 476
FEATURE                  Location/Qualifiers
misc_difference          357..383
                         note = n is any base
source                   1..476
                         mol_type = other DNA
                         organism = synthetic construct
SEQUENCE: 29
gtgacacggc ggttagaacg cggctacaat taatacataa ccccatcccc ctgttgacaa   60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnntctaacc cgctgtctgc gatcttcacc accggcggtc  420
accatcacca tcaccatggc agcggttcta gtctagcggc cgcaactgat cttggc       476

SEQ ID NO: 30            moltype = DNA  length = 473
FEATURE                  Location/Qualifiers
```

```
misc_difference        357..380
                       note = n is any base
source                 1..473
                       mol_type = other DNA
                       organism = synthetic construct
SEQUENCE: 30
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnnnnnn tctaacccgc tgtctgcgat cttcaccacc ggcggtcacc   420
atcaccatca ccatggcagc ggttctagtc tagcggccgc aactgatctt ggc          473

SEQ ID NO: 31          moltype = DNA   length = 470
FEATURE                Location/Qualifiers
misc_difference        357..377
                       note = n is any base
source                 1..470
                       mol_type = other DNA
                       organism = synthetic construct
SEQUENCE: 31
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnnntct aacccgctgt ctgcgatctt caccaccggc ggtcaccatc   420
accatcacca tggcagcggt tctagtctag cggccgcaac tgatcttggc               470

SEQ ID NO: 32          moltype = AA   length = 291
FEATURE                Location/Qualifiers
source                 1..291
                       mol_type = protein
                       organism = Homo sapiens
SEQUENCE: 32
MTKEYQDLQH LDNEESDHHQ LRKGPPPPQP LLQRLCSGPR LLLLSLGLSL LLLVVVCVIG    60
SQNSQLQEEL RGLRETFSNF TASTEAQVKG LSTQGGNVGR KMKSLESQLE KQQKDLSEDH   120
SSLLLHVKQF VSDLRSLSCQ MAALQGNGSE RTCCPVNWVE HERSCYWFSR SGKAWADADN   180
YCRLEDAHLV VVTSWEEQKF VQHHIGPVNT WMGLHDQNGP WKWVDGTDYE TGFKNWRPEQ   240
PDDWYGHGLG GGEDCAHFTD DGRWNDDVCQ RPYRWVCETE LDKASQEPPL L            291

SEQ ID NO: 33          moltype = AA   length = 90
FEATURE                Location/Qualifiers
source                 1..90
                       mol_type = protein
                       organism = synthetic construct
SEQUENCE: 33
MLPAPKNLVV SRVTEDSARL SWTAPDAAFD SFTIQYEELT TVGEAIYLRV PGSERSYDLT    60
GLKPGTEYVV WIEGVKGGLR SNPLGAAFTT                                     90

SEQ ID NO: 34          moltype = AA   length = 90
FEATURE                Location/Qualifiers
source                 1..90
                       mol_type = protein
                       organism = synthetic construct
SEQUENCE: 34
MLPAPKNLVV SRVTEDSARL SWTAPDAAFD SFAITYIEWW DVGEAIGLKV PGSERSYDLT    60
GLKPGTEYRV HIQGVKGGNN SYPLDALFTT                                     90

SEQ ID NO: 35          moltype = AA   length = 90
FEATURE                Location/Qualifiers
source                 1..90
                       mol_type = protein
                       organism = synthetic construct
SEQUENCE: 35
MLPAPKNLVV SRVTEDSARL SWTAPDAAFD SFEIAYFEAI WNGEAIYLTV PGSERSYDLT    60
GLKPGTEYQV EIRGVKGGPT SRPLFAWFTT                                     90

SEQ ID NO: 36          moltype = AA   length = 90
FEATURE                Location/Qualifiers
source                 1..90
                       mol_type = protein
                       organism = synthetic construct
SEQUENCE: 36
MLPAPKNLVV SRVTEDSARL SWTAPDAAFD SFTITYIEWW ENGEAIALSV PGSERSYDLT    60
GLKPGTEYQV GIAGVKGGYK SYPLWALFTT                                     90
```

-continued

```
SEQ ID NO: 37              moltype = AA   length = 90
FEATURE                    Location/Qualifiers
source                     1..90
                           mol_type = protein
                           organism = synthetic construct
SEQUENCE: 37
MLPAPKNLVV SRVTEDSARL SWTAPDAAFD SFHIIYTEEE KEGEAIYLRV PGSERSYDLT    60
GLKPGTEYLV EIEGVKGGKR SVPLNASFTT                                     90

SEQ ID NO: 38              moltype = AA   length = 90
FEATURE                    Location/Qualifiers
source                     1..90
                           mol_type = protein
                           organism = synthetic construct
SEQUENCE: 38
MLPAPKNLVV SRVTEDSARL SWTAPDAAFD SFHIAYEESH TTGEAIFLRV PGSERSYDLT    60
GLKPGTEYSV SIEGVKGGHY SPPLTAKFTT                                     90

SEQ ID NO: 39              moltype = AA   length = 90
FEATURE                    Location/Qualifiers
source                     1..90
                           mol_type = protein
                           organism = synthetic construct
SEQUENCE: 39
MLPAPKNLVV SRVTEDSARL SWTAPDAAFD SFDIDYREWW TLGEAIVLTV PGSERSYDLT    60
GLKPGTEYYV NIQGVKGGLR SYPLSAIFTT                                     90

SEQ ID NO: 40              moltype = AA   length = 90
FEATURE                    Location/Qualifiers
source                     1..90
                           mol_type = protein
                           organism = synthetic construct
SEQUENCE: 40
MLPAPKNLVV SRVTEDSARL SWTAPDAAFD SFVIEYWEYV GHGEAIVLTV PGSERSYDLT    60
GLKPGTEYSV GIYGVKGGSL SRPLSAIFTT                                     90

SEQ ID NO: 41              moltype = AA   length = 90
FEATURE                    Location/Qualifiers
source                     1..90
                           mol_type = protein
                           organism = synthetic construct
SEQUENCE: 41
MLPAPKNLVI SRVTEDSARL SWTAPDAAFD SFFIYYIESY PAGEAIVLTV PGSERSYDLT    60
GLKPGTEYWV GIDGVKGGRW STPLSAIFTT                                     90

SEQ ID NO: 42              moltype = AA   length = 90
FEATURE                    Location/Qualifiers
source                     1..90
                           mol_type = protein
                           organism = synthetic construct
SEQUENCE: 42
MLPAPKNLVV SRVTEDSARL SWTAPDAAFD SFTIEYYESF YGGEAIVLTV PGSERSYDLT    60
GLKPGTEYYV SIYGVKGGWL SRPLSAIFTT                                     90

SEQ ID NO: 43              moltype = AA   length = 90
FEATURE                    Location/Qualifiers
source                     1..90
                           mol_type = protein
                           organism = synthetic construct
SEQUENCE: 43
MLPAPKNLVV SRVTEDSARL SWTAPDAAFD SFYIEYYESY PGGEAIVLTV PGSERSYDLT    60
GLKPGTEYDV YIYGVKGGYW SRPLSAIFTT                                     90

SEQ ID NO: 44              moltype = AA   length = 90
FEATURE                    Location/Qualifiers
source                     1..90
                           mol_type = protein
                           organism = synthetic construct
SEQUENCE: 44
MLPAPKNLVV SRVTEDSARL SWTAPDAAFD SFYIEYYESL PDGEAIVLTV PGSERSYDLT    60
GLKPGTEYAV YIYGVKGGYY SRPLSAIFTT                                     90

SEQ ID NO: 45              moltype = AA   length = 90
FEATURE                    Location/Qualifiers
source                     1..90
                           mol_type = protein
                           organism = synthetic construct
SEQUENCE: 45
```

```
MLPAPKNLVV SRVTEDSARL SWTAPDAAFD SFAIYYLESY PEGEAIVLTV PGSERSYDLT    60
GLKPGTEYWV GIDGVKGGTW SSPLSAIFTT                                     90

SEQ ID NO: 46            moltype = AA   length = 90
FEATURE                  Location/Qualifiers
source                   1..90
                         mol_type = protein
                         organism = synthetic construct
SEQUENCE: 46
MLPAPKNLVV SRVTEDSARL SWTAPDAAFD SFTIEYFEFT GTGEAIVLTV PGSERSYDLT    60
GLKPGTEYYV SIYGVKGGLL SAPLSAIFTT                                     90

SEQ ID NO: 47            moltype = AA   length = 90
FEATURE                  Location/Qualifiers
source                   1..90
                         mol_type = protein
                         organism = synthetic construct
SEQUENCE: 47
MLPAPKNLVV SRVTEDSARL SWTAPDAAFD SFTIWYAEAL GDGEAIVLTV PGSERSYDLT    60
GLKPGTEYFV DIYGVKGGFW SLPLSAIFTT                                     90

SEQ ID NO: 48            moltype = AA   length = 90
FEATURE                  Location/Qualifiers
source                   1..90
                         mol_type = protein
                         organism = synthetic construct
SEQUENCE: 48
MLPAPKNLVV SRVTEDSARL SWTAPDAAFD SFVIEYFEQF NLGEAIVLTV PGSERSYDLT    60
GLKPGTEYWV GIYGVKGGWL SHPLSAIFTT                                     90

SEQ ID NO: 49            moltype = AA   length = 90
FEATURE                  Location/Qualifiers
source                   1..90
                         mol_type = protein
                         organism = synthetic construct
SEQUENCE: 49
MLPAPKNLVV SRVTEDSARL SWTAPDAAFD SFGISYLEWW EDGEAIVLTV PGSERSYDLT    60
GLKPGTEYWV SIAGVKGGKR SYPLSAIFTT                                     90

SEQ ID NO: 50            moltype = AA   length = 90
FEATURE                  Location/Qualifiers
source                   1..90
                         mol_type = protein
                         organism = synthetic construct
SEQUENCE: 50
MLPAPKNLVV SRVTEDSARL SWTAPDAAFD SFVIEYREGA WYGEAIVLTV PGSERSYDLT    60
GLKPGTEYFV DITGVKGGWW SDPLSAIFTT                                     90

SEQ ID NO: 51            moltype = AA   length = 90
FEATURE                  Location/Qualifiers
source                   1..90
                         mol_type = protein
                         organism = synthetic construct
SEQUENCE: 51
MLPAPKNLVV SRVTEDSARL SWTAPDAAFD SFFIKYIEWW ADGEAIVLTV PGSERSYDLT    60
GLKPGTEYLV EIYGVKGGKW SWPLSAIFTT                                     90

SEQ ID NO: 52            moltype = AA   length = 90
FEATURE                  Location/Qualifiers
source                   1..90
                         mol_type = protein
                         organism = synthetic construct
SEQUENCE: 52
MLPAPKNLVV SRVTEDSARL SWTAPDAAFD SFKISYQEWW EDGEAIVLTV PGSERSYDLT    60
GLKPGTEYWV NISGVKGGVQ SYPLSAIFTT                                     90

SEQ ID NO: 53            moltype = AA   length = 90
FEATURE                  Location/Qualifiers
source                   1..90
                         mol_type = protein
                         organism = synthetic construct
SEQUENCE: 53
MLPAPKNLVV SRVTEDSARL SWTAPDAAFD SFFISYIEWW DLGEAIVLTV PGSERSYDLT    60
GLKPGTEYHV EIFGVKGGTQ SYPLSAIFTT                                     90

SEQ ID NO: 54            moltype = AA   length = 90
FEATURE                  Location/Qualifiers
source                   1..90
                         mol_type = protein
```

```
                          organism = synthetic construct
SEQUENCE: 54
MLPAPKNLVV SRVTEDSARL SWTAPDAAFD SFQILYQENA FEGEAIVLTV PGSERSYDLT    60
GLKPGTEYWV YIYGVKGGYP SVPLSAIFTT                                     90

SEQ ID NO: 55              moltype = AA   length = 90
FEATURE                    Location/Qualifiers
source                     1..90
                           mol_type = protein
                           organism = synthetic construct
SEQUENCE: 55
MLPAPKNLVV SRVTEDSARL SWTAPDAAFD SFIIEYWEFV GYGEAIVLTV PGSERSYDLT    60
GLKPGTEYWV AIYGVKGGDL SKPLSAIFTT                                     90

SEQ ID NO: 56              moltype = AA   length = 90
FEATURE                    Location/Qualifiers
source                     1..90
                           mol_type = protein
                           organism = synthetic construct
SEQUENCE: 56
MLPAPKNLVV SRVTEDSARL SWTAPDAAFD SFVIEYFEAL EGGEAIVLTV PGSERSYDLT    60
GLKPGTEYFV GIYGVKGGPL SKPLSAIFTT                                     90

SEQ ID NO: 57              moltype = AA   length = 90
FEATURE                    Location/Qualifiers
source                     1..90
                           mol_type = protein
                           organism = synthetic construct
SEQUENCE: 57
MLPAPKNLVV SRVTEDSARL SWTAPDAAFD SFSIKYLEWW QDGEAIVLTV PGSERSYDLT    60
GLKPGTEYYV HIAGVKGGYR SYPLSAIFTT                                     90

SEQ ID NO: 58              moltype = AA   length = 90
FEATURE                    Location/Qualifiers
source                     1..90
                           mol_type = protein
                           organism = synthetic construct
SEQUENCE: 58
MLPAPKNLVV SRVTEDSARL SWTAPDAAFD SFTIWYAEAD GWGEAIVLTV PGSERSYDLT    60
GLKPGTEYFV DIYGVKGGYL SVPLSAIFTT                                     90

SEQ ID NO: 59              moltype = AA   length = 90
FEATURE                    Location/Qualifiers
source                     1..90
                           mol_type = protein
                           organism = synthetic construct
SEQUENCE: 59
MLPAPKNLVV SRVTEDSARL SWTAPDAAFD SFTIWYAEWE DEGEAIVLTV PGSERSYDLT    60
GLKPGTEYRV EIYGVKGGYP SKPLSAIFTT                                     90

SEQ ID NO: 60              moltype = AA   length = 90
FEATURE                    Location/Qualifiers
source                     1..90
                           mol_type = protein
                           organism = synthetic construct
SEQUENCE: 60
MLPAPKNLVV SRVTEDSARL SWTAPDAAFD SFTIWYAEAI GHGEAIVLTV PGSERSYDLT    60
GLKPGTEYWV DIWGVKGGQQ SKPLSAIFTT                                     90

SEQ ID NO: 61              moltype = AA   length = 94
FEATURE                    Location/Qualifiers
source                     1..94
                           mol_type = protein
                           organism = synthetic construct
SEQUENCE: 61
MLPAPKNLVV SRVTEDSARL SWRVESRTFD SFLIQYQESE KVGEAIVLTV PGSERSYDLT    60
GLKPGTEYTV SIYGVVWDTR DNPISNPLSA IFTT                                94

SEQ ID NO: 62              moltype = AA   length = 92
FEATURE                    Location/Qualifiers
source                     1..92
                           mol_type = protein
                           organism = synthetic construct
SEQUENCE: 62
MLPAPKNLVV SRVTEDSARL SWTAPDAAFD SFPILYLELN HHGEEIVLTV PGSERSYDLT    60
GLKPGTEYWV YIFGVKGGMY SAPLSAIFTT GG                                  92

SEQ ID NO: 63              moltype = AA   length = 4
FEATURE                    Location/Qualifiers
```

-continued

```
source                   1..4
                         mol_type = protein
                         organism = synthetic construct
SEQUENCE: 63
GSGS                                                                           4

SEQ ID NO: 64            moltype = AA   length = 8
FEATURE                  Location/Qualifiers
source                   1..8
                         mol_type = protein
                         organism = synthetic construct
SEQUENCE: 64
GGGSGGGS                                                                       8

SEQ ID NO: 65            moltype = AA   length = 25
FEATURE                  Location/Qualifiers
REGION                   1..25
                         note = synthetic sequence
source                   1..25
                         mol_type = protein
                         organism = synthetic construct
SEQUENCE: 65
GGGGSGGGGS GGGGSGGGGS GGGGS                                                   25

SEQ ID NO: 66            moltype = AA   length = 4
FEATURE                  Location/Qualifiers
source                   1..4
                         mol_type = protein
                         organism = synthetic construct
SEQUENCE: 66
APAP                                                                           4

SEQ ID NO: 67            moltype = AA   length = 10
FEATURE                  Location/Qualifiers
source                   1..10
                         mol_type = protein
                         organism = synthetic construct
SEQUENCE: 67
APAPAPAPAP                                                                    10

SEQ ID NO: 68            moltype = AA   length = 20
FEATURE                  Location/Qualifiers
source                   1..20
                         mol_type = protein
                         organism = synthetic construct
SEQUENCE: 68
APAPAPAPAP APAPAPAPAP                                                         20

SEQ ID NO: 69            moltype = AA   length = 40
FEATURE                  Location/Qualifiers
REGION                   1..40
                         note = synthetic sequence
source                   1..40
                         mol_type = protein
                         organism = synthetic construct
SEQUENCE: 69
APAPAPAPAP APAPAPAPAP APAPAPAPAP APAPAPAPAP                                   40

SEQ ID NO: 70            moltype = AA   length = 29
FEATURE                  Location/Qualifiers
source                   1..29
                         mol_type = protein
                         organism = synthetic construct
SEQUENCE: 70
AEAAAKEAAA KEAAAKEAAA KEAAAKAAA                                               29

SEQ ID NO: 71            moltype =   length =
SEQUENCE: 71
000

SEQ ID NO: 72            moltype =   length =
SEQUENCE: 72
000

SEQ ID NO: 73            moltype =   length =
SEQUENCE: 73
000

SEQ ID NO: 74            moltype =   length =
```

-continued

```
SEQUENCE: 74
000

SEQ ID NO: 75              moltype =    length =
SEQUENCE: 75
000

SEQ ID NO: 76              moltype =    length =
SEQUENCE: 76
000

SEQ ID NO: 77              moltype =    length =
SEQUENCE: 77
000

SEQ ID NO: 78              moltype =    length =
SEQUENCE: 78
000

SEQ ID NO: 79              moltype =    length =
SEQUENCE: 79
000

SEQ ID NO: 80              moltype = AA  length = 230
FEATURE                    Location/Qualifiers
source                     1..230
                           mol_type = protein
                           organism = Homo sapiens
SEQUENCE: 80
QNSQLQEELR GLRETFSNFT ASTEAQVKGL STQGGNVGRK MKSLESQLEK QQKDLSEDHS  60
SLLLHVKQFV SDLRSLSCQM AALQGNGSER TCCPVNWVEH ERSCYWFSRS GKAWADADNY  120
CRLEDAHLVV VTSWEEQKFV QHHIGPVNTW MGLHDQNGPW KWVDGTDYET GFKNWRPEQP  180
DDWYGHGLGG GEDCAHFTDD GRWNDDVCQR PYRWVCETEL DKASQEPPLL             230

SEQ ID NO: 81              moltype = AA  length = 90
FEATURE                    Location/Qualifiers
source                     1..90
                           mol_type = protein
                           organism = synthetic construct
SEQUENCE: 81
MLPAPKNLVV SRVTEDSARL SWTAPDAAFD SFVIEYREGA WYGEAIVLTV PGSERSYDLT  60
GLKPGTEYAV YIPGVKGGPR SFPLSAIFTT                                   90

SEQ ID NO: 82              moltype = AA  length = 90
FEATURE                    Location/Qualifiers
source                     1..90
                           mol_type = protein
                           organism = synthetic construct
SEQUENCE: 82
MLPAPKNLVV SRVTEDSARL SWTAPDAAFD SFAIAYVEWW KLGEAIVLTV PGSERSYDLT  60
GLKPGTEYVV PIPGVKGGGH SSPLSAIFTT                                   90

SEQ ID NO: 83              moltype = AA  length = 90
FEATURE                    Location/Qualifiers
source                     1..90
                           mol_type = protein
                           organism = synthetic construct
SEQUENCE: 83
MLPAPKNLVV SRVTEDSARL SWTAPDAAFD SFYIYYYESS GTGEAIVLTV PGSERSYDLT  60
GLKPGTEYFV DIGGVKGGSY SLPLSAIFTT                                   90

SEQ ID NO: 84              moltype = AA  length = 90
FEATURE                    Location/Qualifiers
source                     1..90
                           mol_type = protein
                           organism = synthetic construct
SEQUENCE: 84
MLPAPKNLVV SRVTEDSARL SWTAPDAAFD SFPIYYWEVF PAGEAIELDV PGSERSYDLT  60
GLKPGTEYFV RIEGVKGGAS SYPLRAEFTT                                   90

SEQ ID NO: 85              moltype = AA  length = 90
FEATURE                    Location/Qualifiers
source                     1..90
                           mol_type = protein
                           organism = synthetic construct
SEQUENCE: 85
MLPAPKNLVV SRVTEDSARL SWTAPDAAFD SFFIWYWEKS VDGEAIVLTV PGSERSYDLT  60
GLKPGTEYNV GIQGVKGGTP SDPLSAIFTT                                   90
```

-continued

```
SEQ ID NO: 86          moltype = AA  length = 90
FEATURE                Location/Qualifiers
source                 1..90
                       mol_type = protein
                       organism = synthetic construct
SEQUENCE: 86
MLPAPKNLVV SRVTEDSARL SWTAPDAAFD SFIIWYAEWV NDGEAIVLTV PGSERSYDLT    60
GLKPGTEYRV EITGVKGGTW SRPLSAIFTT                                      90

SEQ ID NO: 87          moltype = AA  length = 90
FEATURE                Location/Qualifiers
source                 1..90
                       mol_type = protein
                       organism = synthetic construct
SEQUENCE: 87
MLPAPKNLVV SRVTEDSARL SWTAPDAAFD SFAIEYYEPV PAGEAIYLDV PGSERSYDLT    60
GLKPGTEYDV TIYGVKGGYY SHPLFASFTT                                      90

SEQ ID NO: 88          moltype = AA  length = 90
FEATURE                Location/Qualifiers
source                 1..90
                       mol_type = protein
                       organism = synthetic construct
SEQUENCE: 88
MLPAPKNLVV SRVTEDSARL SWTAPDAAFD SFWIEYFEWT VGGEAIVLTV PGSERSYDLT    60
GLKPGTEYYV SIYGVKGGWL SPPLSAIFTT                                      90

SEQ ID NO: 89          moltype = AA  length = 90
FEATURE                Location/Qualifiers
source                 1..90
                       mol_type = protein
                       organism = synthetic construct
SEQUENCE: 89
MLPAPKNLVV SRVTEDSARL SWTAPDAAFD SFHISYEETP VVGEAIYLRV PGSERSYDLT    60
GLKPGTEYTV AIHGVKGGRE STPLIAPFTT                                      90

SEQ ID NO: 90          moltype = AA  length = 90
FEATURE                Location/Qualifiers
source                 1..90
                       mol_type = protein
                       organism = synthetic construct
SEQUENCE: 90
MLPAPKNLVV SRVTEDSARL SWTAPDAAFD SFTIHYWEFD PPGEAIVLTV PGSERSYDLT    60
GLKPGTEYTV YIEGVKGGWW SKPLSAIFTT                                      90

SEQ ID NO: 91          moltype = AA  length = 90
FEATURE                Location/Qualifiers
source                 1..90
                       mol_type = protein
                       organism = synthetic construct
SEQUENCE: 91
MLPAPKNLVV SRVTEDSARL SWTAPDAAFD SFVIEYWERT QPGEAIVLTV PGSERSYDLT    60
GLKPGTEYDV WISGVKGGKW SEPLSAIFTT                                      90

SEQ ID NO: 92          moltype = AA  length = 90
FEATURE                Location/Qualifiers
source                 1..90
                       mol_type = protein
                       organism = synthetic construct
SEQUENCE: 92
MLPAPKNLVV SRVTEDSARL SWTAPDAAFD SFLIRYWEWY VLGEAIVLTV PGSERSYDLT    60
GLKPGTEYYV EISGVKGGWQ SWPLSAIFTT                                      90

SEQ ID NO: 93          moltype = AA  length = 90
FEATURE                Location/Qualifiers
source                 1..90
                       mol_type = protein
                       organism = synthetic construct
SEQUENCE: 93
MLPAPKNLVV SRVTEDSARL SWTAPDAAFD SFYIGYLEPG DNGEAIVLTV PGSERSYDLT    60
GLKPGTEYNV SIGGVKGGLG SYPLSAIFTT                                      90

SEQ ID NO: 94          moltype = AA  length = 90
FEATURE                Location/Qualifiers
source                 1..90
                       mol_type = protein
                       organism = synthetic construct
SEQUENCE: 94
MLPAPKNLVV SRITEDSARL SWTAPDAAFD SFGIYYYEWW STGEAIVLTV PGSERSYDLT    60
```

-continued

```
GPKPGTEYYV KISGVKGGYR SYPLSAIFTT                                    90

SEQ ID NO: 95          moltype = AA  length = 90
FEATURE                Location/Qualifiers
source                 1..90
                       mol_type = protein
                       organism = synthetic construct
SEQUENCE: 95
MLPAPKNLVV SRVTEDSARL SWTAPDAAFD SFRISYYEWY DLGEAIVLTV PGSERSYDLT   60
GLKPGTEYWV DIAGVKGGYY SYPLSAIFTT                                    90

SEQ ID NO: 96          moltype = AA  length = 90
FEATURE                Location/Qualifiers
source                 1..90
                       mol_type = protein
                       organism = synthetic construct
SEQUENCE: 96
MLPAPKNLVV SRVTEDSARL SWTAPDAAFD SFFIGYLEPQ PPGEAIVLTV PGSERSYDLT   60
GLKPGTEYNV TIQGVKGGFP SMPLSAIFTT                                    90

SEQ ID NO: 97          moltype = AA  length = 90
FEATURE                Location/Qualifiers
source                 1..90
                       mol_type = protein
                       organism = synthetic construct
SEQUENCE: 97
MLPAPKNLVV SRVTEDSARL SWTAPDAAFD SFFISYFEGW ASGEAIHLYV PGSERSYDLT   60
GLKPGTEYSV HIQGVKGGQP STPLSAIFTT                                    90

SEQ ID NO: 98          moltype = AA  length = 90
FEATURE                Location/Qualifiers
source                 1..90
                       mol_type = protein
                       organism = synthetic construct
SEQUENCE: 98
MLPAPKNLVV SRITEDSARL SWTAPDAAFD SFDIPYGEFD TIGEAIVLTV PGSERSYDLT   60
GLKPGTEYDV YIEGVKGGHL SWPLSAIFTT                                    90

SEQ ID NO: 99          moltype = AA  length = 90
FEATURE                Location/Qualifiers
source                 1..90
                       mol_type = protein
                       organism = synthetic construct
SEQUENCE: 99
MLPAPKNLVV SRVTEDSARL SWTAPDAAFD SFGIQYNEFV FRGEAIVLTV PGSERSYDLT   60
GLKPGTEYFV PISGVKGGDD SRPLSAIFTT                                    90

SEQ ID NO: 100         moltype = AA  length = 90
FEATURE                Location/Qualifiers
source                 1..90
                       mol_type = protein
                       organism = synthetic construct
SEQUENCE: 100
MLPAPKNLVV SRVTEDSARL SWTAPDAAFD SFWIEYWEVV GFGEAIVLTV PGSERSYDLT   60
GLKPGTEYWV GIYGVKGGNP SVPLSAIFTT                                    90

SEQ ID NO: 101         moltype = AA  length = 90
FEATURE                Location/Qualifiers
source                 1..90
                       mol_type = protein
                       organism = synthetic construct
SEQUENCE: 101
MLPAPKNLVV SRVTEDSARL SWTAPDAAFD SFAIDYDEPI NSGEAIVLTV PGSERSYDLT   60
GPKPGTEYEV EIYGVKGGYL SRPLSAIFTT                                    90

SEQ ID NO: 102         moltype = AA  length = 90
FEATURE                Location/Qualifiers
source                 1..90
                       mol_type = protein
                       organism = synthetic construct
SEQUENCE: 102
MLPAPKNLVV SRVTEDSARL SWTAPDAAFD SFSIDYDEPQ PVGEAIVLTV PGSERSYDLT   60
GLKPGTEYRV DIWGVKGGPT SGPLRATFTT                                    90

SEQ ID NO: 103         moltype = AA  length = 90
FEATURE                Location/Qualifiers
source                 1..90
                       mol_type = protein
                       organism = synthetic construct
```

```
SEQUENCE: 103
MLLAPKNLVV SRVTEDSARL SWTAPDAAFD SFAIEYFEYT GEGEAIVLTV PGSERSYDLT   60
GLKPGTEYYV GIYGVKGGYL SRPLSAIFTT                                    90

SEQ ID NO: 104          moltype = AA   length = 90
FEATURE                 Location/Qualifiers
source                  1..90
                        mol_type = protein
                        organism = synthetic construct
SEQUENCE: 104
MLPAPKNLVV SHVTEDSARL SWTAPDAAFD SFDIEYYELV GSGEAIVLTV PGSERSYDLT   60
GLKPGTEYYV AIYGVKGGYL SRPLSAIFTT                                    90

SEQ ID NO: 105          moltype = AA   length = 90
FEATURE                 Location/Qualifiers
source                  1..90
                        mol_type = protein
                        organism = synthetic construct
SEQUENCE: 105
MLPAPKNLVV SRVTEDSARL SWTAPDAAFD SFGIAYYERS GAGEAIVLTV PGSERSYDLT   60
GLKPGTEYMV YINGVKGGFV SSPLSAIFTT                                    90

SEQ ID NO: 106          moltype = AA   length = 90
FEATURE                 Location/Qualifiers
source                  1..90
                        mol_type = protein
                        organism = synthetic construct
SEQUENCE: 106
MLPAPKNLVV SRVTEDSARL SWTAPDAAFD SFTIAYEEHG LVGEAIYLRV PGSERSYDLT   60
GLKPGTEYHV GIMGVKGGVF SSPLSAIFTT                                    90

SEQ ID NO: 107          moltype = AA   length = 90
FEATURE                 Location/Qualifiers
source                  1..90
                        mol_type = protein
                        organism = synthetic construct
SEQUENCE: 107
MLPAPKNLVV SRVTEDSARL SWTAPDAAFD SFFIQYTESH WVGEAIVLTV PGSERSYDLT   60
GLKPGTEYAV PIEGVKGGDS STPLSAIFTT                                    90

SEQ ID NO: 108          moltype = AA   length = 90
FEATURE                 Location/Qualifiers
source                  1..90
                        mol_type = protein
                        organism = synthetic construct
SEQUENCE: 108
MLPAPKNLVV SRVTEDSARL SWTAPDAAFD SFTIIYGEVN PYGEAIVLTV PGSERSYDLT   60
GLKPGTEYDV FIEGVKGGHL SWPLSAIFTT                                    90

SEQ ID NO: 109          moltype = AA   length = 90
FEATURE                 Location/Qualifiers
source                  1..90
                        mol_type = protein
                        organism = synthetic construct
SEQUENCE: 109
MLPAPKNLVV SRVTEDSARL SWTAPDAAFD SFHIAYEELV TEGEAIYLRV PGSERSYDLT   60
GLKPGTEYLV DIEGVKGGHL SSPLSAIFTT                                    90

SEQ ID NO: 110          moltype = AA   length = 90
FEATURE                 Location/Qualifiers
source                  1..90
                        mol_type = protein
                        organism = synthetic construct
SEQUENCE: 110
MLPAPKNLVV SRVTEDSARL SWTAPDAAFD SFFIHYHEWW EAGEAIVLTV PGSERSYDLT   60
GLKPGTEYLV DIPGVKGGDL SVPLSAIFTT                                    90

SEQ ID NO: 111          moltype = AA   length = 90
FEATURE                 Location/Qualifiers
source                  1..90
                        mol_type = protein
                        organism = synthetic construct
SEQUENCE: 111
MLPAPKNLVV SRVTEDSARL SWTAPDAAFD SFWIYYYESV GTGEAIVLTV PGSERSYDLT   60
GLKPGTEYFV DISGVKVGTY SLPLSAIFTT                                    90

SEQ ID NO: 112          moltype = AA   length = 90
FEATURE                 Location/Qualifiers
source                  1..90
```

```
                              mol_type = protein
                              organism = synthetic construct
SEQUENCE: 112
MLPAPKNLVV SRVTEDSARL SWTAPDAAFD SFFIAYFEFA NPGEAIVLTV PGSERSYDLT   60
GLKPGTEYKV VIQGVKGGTP SEPLSAISTT                                    90

SEQ ID NO: 113            moltype = AA   length = 90
FEATURE                   Location/Qualifiers
source                    1..90
                          mol_type = protein
                          organism = synthetic construct
SEQUENCE: 113
MLPAPKNLVV SRVTEDSARL SWTAPDAAFD SFDIHYKEHS WWGEAIVLTV PGSERSYDLT   60
GLKPGTEYIV PIPGVKGGGI SRPLSAIFTT                                    90

SEQ ID NO: 114            moltype = AA   length = 90
FEATURE                   Location/Qualifiers
source                    1..90
                          mol_type = protein
                          organism = synthetic construct
SEQUENCE: 114
MLPAPKNLVV SRVTEDSARL SWTAPDAAFD SFAIEYWEAV GSGEAIVLTV PGSERSYDLT   60
GLKPGTEYHV YIYGVKGGYL SLPLSAIFTT                                    90

SEQ ID NO: 115            moltype = AA   length = 91
FEATURE                   Location/Qualifiers
source                    1..91
                          mol_type = protein
                          organism = synthetic construct
SEQUENCE: 115
MLPAPKNLVV SRVTEDSARL SWTAPDAAFD SFFIGYLEPQ PPGEAIVLTV PGSERSYDLT   60
GLKPGTEYNV TIQGVKGGFP SMPLSAIFTT T                                  91

SEQ ID NO: 116            moltype = AA   length = 90
FEATURE                   Location/Qualifiers
source                    1..90
                          mol_type = protein
                          organism = synthetic construct
SEQUENCE: 116
MLPAPKNLVV SRVTEDSARL SWTAPDAAFD SFSIAYSEVR YDGEAIVLTV PGSERSYDLT   60
GLKPGTEYVV PIGGVKGGGS SSPLSAIFTT                                    90

SEQ ID NO: 117            moltype = AA   length = 90
FEATURE                   Location/Qualifiers
source                    1..90
                          mol_type = protein
                          organism = synthetic construct
SEQUENCE: 117
MLPAPKNLVV SRVTEDSARL SWTAPDAAFD SFTIPYGEAF NPGEAIVLTV PGSERSYDLT   60
GLKPGTEYDV FIEGVKGGTL SWPLSAIFTT                                    90

SEQ ID NO: 118            moltype = AA   length = 90
FEATURE                   Location/Qualifiers
source                    1..90
                          mol_type = protein
                          organism = synthetic construct
SEQUENCE: 118
MLPAPKNLVV SRVTEDSARL SWTAPDAAFD SFRILYGEVD PWGEAIVLTV PGSERSYDLT   60
GLKPGTEYDV WIEGVKGGKL SWPLSAIFTT                                    90

SEQ ID NO: 119            moltype = AA   length = 90
FEATURE                   Location/Qualifiers
source                    1..90
                          mol_type = protein
                          organism = synthetic construct
SEQUENCE: 119
MLPAPKNLVV SRVTEDSARL SWTAPDAAFD SFHIEYEETP QKGEAIFLRV PGSERSYDLT   60
GLKPGTEYVV NIRGVKGGDL SSPLGALFTT                                    90

SEQ ID NO: 120            moltype = AA   length = 90
FEATURE                   Location/Qualifiers
source                    1..90
                          mol_type = protein
                          organism = synthetic construct
SEQUENCE: 120
MLPAPKNLVV SRVTEDSARL SWTAPDAAFD SFRIEYIEWW VGGEAIVLTV PGSERSYDLT   60
GLKPGTEYWV DIKGVKGGKR SYPLSAIFTT                                    90

SEQ ID NO: 121            moltype = AA   length = 90
```

```
FEATURE                Location/Qualifiers
source                 1..90
                       mol_type = protein
                       organism = synthetic construct
SEQUENCE: 121
MLPAPKNLVV SRVTEDSARL SWTAPDAAFD SFSIDYPEFP VRGEAIVLTV PGSERSYDLT   60
GPKPGTEYNV TIQGVKGGFP SMPLSAIFTT                                    90

SEQ ID NO: 122         moltype = AA   length = 90
FEATURE                Location/Qualifiers
source                 1..90
                       mol_type = protein
                       organism = synthetic construct
SEQUENCE: 122
MLPAPKNLVV SRVTEDSARL SWTAPDAAFD SFQIPYWEQS LGGEAIVLTV PGSERSYDLT   60
GLKPGTEYEV WIEGVKGGDL SFPLSAISTT                                    90

SEQ ID NO: 123         moltype = AA   length = 90
FEATURE                Location/Qualifiers
source                 1..90
                       mol_type = protein
                       organism = synthetic construct
SEQUENCE: 123
MLPAPKNLVV SRVTEDSARL SWTAPDAAFD SFVIPYEEYL YTGEAIVLTV PGSERSYDLT   60
GLKPGTEYDV WIEGVKGGLT SWPLSAIFTT                                    90

SEQ ID NO: 124         moltype = AA   length = 90
FEATURE                Location/Qualifiers
source                 1..90
                       mol_type = protein
                       organism = synthetic construct
SEQUENCE: 124
MLPAPKNLVV SRVTEDSARL SWTAPDAAFD SFSIDYPEFP VRGEAIVLTV PGSERSYDLT   60
GLKPGTEYAV TIWGVKGGFT SQPLSAIFTT                                    90

SEQ ID NO: 125         moltype = AA   length = 90
FEATURE                Location/Qualifiers
source                 1..90
                       mol_type = protein
                       organism = synthetic construct
SEQUENCE: 125
MLPAPKNLVV SRVTEDSARL SWTAPDAAFD SFVIEYFEFV GEGEAIVLTV PGSERSYDLT   60
GLKPGTEYDV GIYGVKGGSL SSPLSAIFTT                                    90

SEQ ID NO: 126         moltype = AA   length = 90
FEATURE                Location/Qualifiers
source                 1..90
                       mol_type = protein
                       organism = synthetic construct
SEQUENCE: 126
MLPAPKNLVV SRVTEDSARL SWTAPDAAFD SFSIDYLELG ESGEAIVLTV PGSERSYDLT   60
GLKPGTEYWV YIFGVKGGYP SAPLSAIFTT                                    90

SEQ ID NO: 127         moltype = AA   length = 90
FEATURE                Location/Qualifiers
source                 1..90
                       mol_type = protein
                       organism = synthetic construct
SEQUENCE: 127
MLPAPKNLVV SRVTEDSARL SWTAPDAAFD SFPIPYGESP PSGEAIVLTV PGSERSYDLT   60
GLKPGTEYVV IIRGVKGGGR SGPLSAISTT                                    90

SEQ ID NO: 128         moltype = AA   length = 90
FEATURE                Location/Qualifiers
source                 1..90
                       mol_type = protein
                       organism = synthetic construct
SEQUENCE: 128
MLPAPKNLVV SRVTEDSARL SWTAPDAAFD SFIINYIEIV QYGEAIVLTV PGSERSYDLT   60
GLKPGTEYPE SIWGVKGGGA SSPLSAIFTT                                    90

SEQ ID NO: 129         moltype = AA   length = 90
FEATURE                Location/Qualifiers
source                 1..90
                       mol_type = protein
                       organism = synthetic construct
SEQUENCE: 129
MLPAPKNLVV SRVTEDSARL SWTAPDAAFD SFDIEYYEAV GAGEAIVLTV PGSERSYDLT   60
GLKPGTEYTV GIYGVKGGWL SKPLSVIFTT                                    90
```

```
SEQ ID NO: 130          moltype = AA  length = 90
FEATURE                 Location/Qualifiers
source                  1..90
                        mol_type = protein
                        organism = synthetic construct
SEQUENCE: 130
MLPAPKNLVV SRVTEDSARL SWTAPDAAFD SFHIPYVEAE VPGEAIQLHV PGSERSYDLT    60
GLKPGTEYYV EIWGVKGGFY SPPLIAEFTT                                     90

SEQ ID NO: 131          moltype = AA  length = 90
FEATURE                 Location/Qualifiers
source                  1..90
                        mol_type = protein
                        organism = synthetic construct
SEQUENCE: 131
MLPAPKNLVV SRVTEDSARL SWTAPDAAFD SFSIDYYEGK GYGEAIVLTV PGSERSYDLT    60
GLKPGTEYQV LISGVKGGKY SLPLSAIFTT                                     90

SEQ ID NO: 132          moltype = AA  length = 90
FEATURE                 Location/Qualifiers
source                  1..90
                        mol_type = protein
                        organism = synthetic construct
SEQUENCE: 132
MLPAPKNLVV SRVTEDSARL SWTAPDAAFD SFTIVYAEVT YDGEAIVLTV PGSERSYDLT    60
GLKPGTEYDV FIEGVKGGEL SWPLSAIFTT                                     90

SEQ ID NO: 133          moltype = AA  length = 90
FEATURE                 Location/Qualifiers
source                  1..90
                        mol_type = protein
                        organism = synthetic construct
SEQUENCE: 133
MLPAPKNLVV SRVTEDSARL SWTAPDAAFD SFPIVYGEAW VTGEAIVLTV PGSERSYDLT    60
GLKPGTEYDV WIEGVKGGEL SWPLSAIFTT                                     90

SEQ ID NO: 134          moltype = AA  length = 90
FEATURE                 Location/Qualifiers
source                  1..90
                        mol_type = protein
                        organism = synthetic construct
SEQUENCE: 134
MLPAPKNLVV SRVTEDSARL SWTAPDAAFD SFWIDYYERK YVGEAIVLTV PGSERSYDLT    60
GLKPGTEYEV TIYGVKGGWY SDPLSAIFTT                                     90

SEQ ID NO: 135          moltype = AA  length = 90
FEATURE                 Location/Qualifiers
source                  1..90
                        mol_type = protein
                        organism = synthetic construct
SEQUENCE: 135
MLPAPKNLVV SRVTEDSARL SWTAPDAAFD SFPISYYEMS GLGEAIVLTV PGSERSYDLT    60
GLKPGTEYMV YIFGVKGGLN SLPLSAIFTT                                     90

SEQ ID NO: 136          moltype = AA  length = 90
FEATURE                 Location/Qualifiers
source                  1..90
                        mol_type = protein
                        organism = synthetic construct
SEQUENCE: 136
MLPAPKNLVV SRVTEDSARL SWTAPDAAFD SFFIYYIESY PAGEAIVLTV PGSERSYDLT    60
GLKPGTEYWM GIDGVKGGRW STPLSAIFTT                                     90

SEQ ID NO: 137          moltype = AA  length = 90
FEATURE                 Location/Qualifiers
source                  1..90
                        mol_type = protein
                        organism = synthetic construct
SEQUENCE: 137
MLPAPKNLVV SRVTEDSARL SWTAPDAAFD SFEIEYDEPS VAGEAIVLTV PGSERSYDLT    60
GLKPGTEYRV FIWGVKGGNQ SWPLSAIFTT                                     90

SEQ ID NO: 138          moltype = AA  length = 90
FEATURE                 Location/Qualifiers
source                  1..90
                        mol_type = protein
                        organism = synthetic construct
SEQUENCE: 138
```

```
MLPAPKNLVV SRVTEDSARL SWTAPDAAFD SFFIKYIEWW ADGEAIVLTV PGSERSYDLT   60
GLKPGTEYLV EIYGVKGGRQ SYPLSAIFTT                                     90

SEQ ID NO: 139              moltype = AA  length = 90
FEATURE                     Location/Qualifiers
source                      1..90
                            mol_type = protein
                            organism = synthetic construct
SEQUENCE: 139
MLPAPKNLVV SRVTEDSARL SWTAPDAAFD SFDISYWESG KYGEAIVLTV PGSESSYDLT   60
GLKPGTEYLV DIFGVKGGYP SEPLSAIFTT                                     90

SEQ ID NO: 140              moltype = AA  length = 90
FEATURE                     Location/Qualifiers
source                      1..90
                            mol_type = protein
                            organism = synthetic construct
SEQUENCE: 140
MLPAPKNLVV SRVTEDSARL SWTAPDAAFD SFWISYEESD TEGEAIYLRV PGSERSYDLT   60
GLKPGTEYNV TIQGVKGGFP SMPLSAIFTT                                     90

SEQ ID NO: 141              moltype = AA  length = 90
FEATURE                     Location/Qualifiers
source                      1..90
                            mol_type = protein
                            organism = synthetic construct
SEQUENCE: 141
MLPAPKNLVV SRVTEDSARL SWTAPDAAFD SFVIEYFEQF NLGEAIVLTV PGSERSYDLT   60
GLKPGTEYLV GIYGVKGGWL SHPLSAIFTT                                     90

SEQ ID NO: 142              moltype = AA  length = 90
FEATURE                     Location/Qualifiers
source                      1..90
                            mol_type = protein
                            organism = synthetic construct
SEQUENCE: 142
MLPAPKNLVV SRVTKDSARL SWTAPDAAFD SFHIAYEEAT TYGEAIFLRV PGSERSYDLT   60
GLKPGTEYEV KIHGVKGGAD SKPLVAPFTT                                     90

SEQ ID NO: 143              moltype = AA  length = 90
FEATURE                     Location/Qualifiers
source                      1..90
                            mol_type = protein
                            organism = synthetic construct
SEQUENCE: 143
MLPAPKNLVV SRVTEDSARL SWTAPDAAFD SFHIAYEEAD SEGEAIYLRV PGSERSYDLT   60
GLKPGTEYSV NIQGVKGGIV SFPLHAEFTT                                     90

SEQ ID NO: 144              moltype = AA  length = 90
FEATURE                     Location/Qualifiers
source                      1..90
                            mol_type = protein
                            organism = synthetic construct
SEQUENCE: 144
MLPAPKNLVV SRVTEDSARL SWTAPDAAFD SFIIPYAEVR PDGEAIVLTV PGSERSYDLT   60
GLKPGTEYSV LIHGVKGGKL SLPLSAIFTT                                     90

SEQ ID NO: 145              moltype = AA  length = 90
FEATURE                     Location/Qualifiers
source                      1..90
                            mol_type = protein
                            organism = synthetic construct
SEQUENCE: 145
MLPAPKNLVV SRVTEDSARL SWTAPDAAFD SFFIPYAEPS PTGEAIVLTV PGSERSYDLT   60
GLKPGTEYDV WIEGVKGGTL SWPLSAIFTT                                     90

SEQ ID NO: 146              moltype = AA  length = 90
FEATURE                     Location/Qualifiers
source                      1..90
                            mol_type = protein
                            organism = synthetic construct
SEQUENCE: 146
MLPAPKNLVV SRVTEDSARL SWTAPDAAFD SFYIAYAEPR PDGEAIVLTV PGSERSYDLT   60
GLKPGTEYSV LIHGVKGGLL SSPLSAIFTT                                     90

SEQ ID NO: 147              moltype = AA  length = 90
FEATURE                     Location/Qualifiers
source                      1..90
                            mol_type = protein
```

```
                              organism = synthetic construct
SEQUENCE: 147
MLPAPKNLVV SRVTEDSARL SWTAPDAAFD SFFIGYLEPQ PPGEAIVLTV PGSERSYDLT    60
GLKPGTEYSV LIHGVKGGRN SDPLSAISTT                                     90

SEQ ID NO: 148             moltype = AA  length = 90
FEATURE                    Location/Qualifiers
source                     1..90
                           mol_type = protein
                           organism = synthetic construct
SEQUENCE: 148
MLPAPKNLVV SRVTEDSARL SWTAPDAAFD SFHIEYEEQY STGEAIYLRV PGSERSYDLT    60
GLKPGTEYHV DIEGVKGGRR SFPLNAFFTT                                     90

SEQ ID NO: 149             moltype = AA  length = 90
FEATURE                    Location/Qualifiers
source                     1..90
                           mol_type = protein
                           organism = synthetic construct
SEQUENCE: 149
MLPAPKNLVV SRVTEDSARL SWTAPDAAFD SFIIPYAEVR PDGEAIVLTV PGSERSYDLT    60
GLKPGTEYSV LIHGVKGGKL SEPLSAIFTT                                     90

SEQ ID NO: 150             moltype = AA  length = 90
FEATURE                    Location/Qualifiers
source                     1..90
                           mol_type = protein
                           organism = synthetic construct
SEQUENCE: 150
MLPAPKNLVV SRVTEDSARL SWTAPDAAFD SFPIAYAEPS PTGEAIVLTV PGSERSYDLT    60
GLKPGTEYSV LIHGVKGGHL SDPLSAIFTT                                     90

SEQ ID NO: 151             moltype = AA  length = 90
FEATURE                    Location/Qualifiers
source                     1..90
                           mol_type = protein
                           organism = synthetic construct
SEQUENCE: 151
MLPAPKNLVV SRVTEDSARL SWTAPDAAFD SFFIPYAEPS PTGEAIVLTV PGSERSYDLT    60
GLKPGTEYGV VILGVKGGYG SDPLSAIFTT                                     90

SEQ ID NO: 152             moltype = AA  length = 90
FEATURE                    Location/Qualifiers
source                     1..90
                           mol_type = protein
                           organism = synthetic construct
SEQUENCE: 152
MLPAPKNLVV SRVTEDSARL SWTAPDAAFD SFFIGYLEPQ PPGEAIVLTV PGSERSYDLT    60
GLKPGTEYNV TIQGVKGGFP SSPLSAIFTT                                     90

SEQ ID NO: 153             moltype = AA  length = 90
FEATURE                    Location/Qualifiers
source                     1..90
                           mol_type = protein
                           organism = synthetic construct
SEQUENCE: 153
MLPAPKNLVV SRVTEDSARL SWTAPDAALD SFRIAYTEYF VGGEAIVLTV PGSERSYDLT    60
GLKPGTEYGV GIYGVKGGAG SSPLSAIFTT                                     90

SEQ ID NO: 154             moltype = AA  length = 90
FEATURE                    Location/Qualifiers
source                     1..90
                           mol_type = protein
                           organism = synthetic construct
SEQUENCE: 154
MLPAPKNLVV SRVTEDSARL SWTAPDAAFD SFFIPYAEPR PDGEAIVLTV PGSERSYDLT    60
GLKPGTEYSV LIHGVKGGLL SSPLSAIFTT                                     90

SEQ ID NO: 155             moltype = AA  length = 90
FEATURE                    Location/Qualifiers
source                     1..90
                           mol_type = protein
                           organism = synthetic construct
SEQUENCE: 155
MLPAPKNLVV SRVTEDSARL SWTAPDAAFD SFPITYRERS QYGEAIVLTV PGSERSYDLT    60
GLKPGTEYVV PIEGVKGGRG SKPLSAIFTT                                     90

SEQ ID NO: 156             moltype = AA  length = 90
FEATURE                    Location/Qualifiers
```

-continued

```
source                    1..90
                          mol_type = protein
                          organism = synthetic construct
SEQUENCE: 156
MLPAPKNLVV SRVTEDSARL SWTAPDAAFD SFAIEYFENL GIGEAIVLTV PGSERSYDLT   60
GLKPGTEYVV NIYGVKGGWL SSPLSAIFTT                                     90

SEQ ID NO: 157           moltype = AA  length = 90
FEATURE                  Location/Qualifiers
source                   1..90
                         mol_type = protein
                         organism = synthetic construct
SEQUENCE: 157
MLPAPKNLVV SRVTEDSARL SWTAPDAAFD SFAIEYYEYV GNGEAIVLTV PGSERSYDLT   60
GLKPGTEYQV GIYGVKGGYY SRPLSAIFTT                                     90

SEQ ID NO: 158           moltype = AA  length = 90
FEATURE                  Location/Qualifiers
source                   1..90
                         mol_type = protein
                         organism = synthetic construct
SEQUENCE: 158
MLPAPKNLVV SRVTEDSARL SWTAPDAAFD SFIIDYLELD DYGEAIVLTV PGSERSYDLT   60
GLKPGTEYPV YIYGVKGGLP STPLSAIFTT                                     90

SEQ ID NO: 159           moltype = AA  length = 90
FEATURE                  Location/Qualifiers
source                   1..90
                         mol_type = protein
                         organism = synthetic construct
SEQUENCE: 159
MLPAPKNLVV SRVTEDSARL SWTAPDAAFD SFLIPYAETS PSGEAIVLTV PGSERSYDLT   60
GLKPGTEYSV LIHGVKGGRN SDPLSAIFTT                                     90

SEQ ID NO: 160           moltype = AA  length = 90
FEATURE                  Location/Qualifiers
source                   1..90
                         mol_type = protein
                         organism = synthetic construct
SEQUENCE: 160
MLPAPKNLVV SRVTEDSARL SWTAPDAAFD SFNIAYGEWR QHGEAIVLTV PGSERSYDLT   60
GLKPGTEYDV FIDGVKGGNL SWPLSAIFTT                                     90

SEQ ID NO: 161           moltype = AA  length = 90
FEATURE                  Location/Qualifiers
source                   1..90
                         mol_type = protein
                         organism = synthetic construct
SEQUENCE: 161
MLPAPKNLVV SRVTEDSARL SWTAPDAAFD SFTIRYWEEL PTGEAIVLTV PGSERSYDLT   60
GLKPGTEYTV EIFGVKGGYL SRPLSAISTT                                     90

SEQ ID NO: 162           moltype = AA  length = 90
FEATURE                  Location/Qualifiers
source                   1..90
                         mol_type = protein
                         organism = synthetic construct
SEQUENCE: 162
MLPAPKNLVV SRVTEDSARL SWTAPDAAFD SFHIAYEEAT TYGEAIFLRV PGSERSYDLT   60
GLKPGTEYDV WIEGVKGGTI SGPLSAIFTT                                     90

SEQ ID NO: 163           moltype = AA  length = 90
FEATURE                  Location/Qualifiers
source                   1..90
                         mol_type = protein
                         organism = synthetic construct
SEQUENCE: 163
MLPAPKNLVV SRVTEDSARL SWTAPDAAFD SFPIAYAEPR PDGEAIVLTV PGSERSYDLT   60
GLKPGTEYFV DIFGVKGGTL SRPLSAIFTT                                     90

SEQ ID NO: 164           moltype = AA  length = 90
FEATURE                  Location/Qualifiers
source                   1..90
                         mol_type = protein
                         organism = synthetic construct
SEQUENCE: 164
MLPAPKNLVV SRVTEDSARL SWTAPDAAFD SFLIPYAETS PSGEAIVLTV PGSERSYDLT   60
GLKPGTEYSV LIHGVKGGHL SDPLSAIFTT                                     90
```

```
SEQ ID NO: 165           moltype = AA  length = 90
FEATURE                  Location/Qualifiers
source                   1..90
                         mol_type = protein
                         organism = synthetic construct
SEQUENCE: 165
MLPARKNLVV SRVTEDSARL SWTAPDAAFD SFFIPYAEPS PTGEAIVLTV PGSERSYDLT   60
GLKPGTEYSV LIHGVKGGHL SDPLSAISTT                                    90

SEQ ID NO: 166           moltype = AA  length = 90
FEATURE                  Location/Qualifiers
source                   1..90
                         mol_type = protein
                         organism = synthetic construct
SEQUENCE: 166
MLPAPKNLVV SRVTEDSARL SWTAPDAAFD SFTILYNEIQ NVGEAIVLTV PGSERSYDLT   60
GLKPGTEYDV WIEGVKGGEL SWPLSAIFTT                                    90

SEQ ID NO: 167           moltype = AA  length = 90
FEATURE                  Location/Qualifiers
source                   1..90
                         mol_type = protein
                         organism = synthetic construct
SEQUENCE: 167
MLPAPKNLVV SRVTEDSARL SWTAPDAAFD SFFIGYLEPQ PPGEAIVLTV PGSERSYDLT   60
GLKPGTEYNV TIQGVKGGTP SEPLSAIFTT                                    90

SEQ ID NO: 168           moltype = AA  length = 90
FEATURE                  Location/Qualifiers
source                   1..90
                         mol_type = protein
                         organism = synthetic construct
SEQUENCE: 168
MLPAPKNLVV SRVTEDSARL SWTTPDAAFD SFFIGYLEPY PPGEAIVLTV PGSERSYDLT   60
GLKPGTEYVV SIQGVKGGKP SDPLSAIFTT                                    90

SEQ ID NO: 169           moltype = AA  length = 90
FEATURE                  Location/Qualifiers
source                   1..90
                         mol_type = protein
                         organism = synthetic construct
SEQUENCE: 169
MLPAPKNLVV SRVTEDSARL SWTAPDAAFD SFFIGYLEPQ PPGEAIVLTV PGSERSYDLT   60
GLKPGTEYNV TIQGVKGGFP SVPLSAIFTT                                    90

SEQ ID NO: 170           moltype = AA  length = 90
FEATURE                  Location/Qualifiers
source                   1..90
                         mol_type = protein
                         organism = synthetic construct
SEQUENCE: 170
MLPAPKNLVV SRVTEDSARL SWTAPDAAFD SFFIGYPEYP ATGEAIVLTV PGSERSYDLT   60
GLKPGTEYFV DINGVKGGSL SYPLSAIFTT                                    90

SEQ ID NO: 171           moltype = AA  length = 90
FEATURE                  Location/Qualifiers
source                   1..90
                         mol_type = protein
                         organism = synthetic construct
SEQUENCE: 171
MLPAPKNLVV SRVTEDSARL SWTAPDAAFD SFAIRYLEWW DVGEAIVLTV PGSERSYDLT   60
GLKPGTEYLV EIKGVKGGKF SYPLSAIFTT                                    90

SEQ ID NO: 172           moltype = AA  length = 90
FEATURE                  Location/Qualifiers
source                   1..90
                         mol_type = protein
                         organism = synthetic construct
SEQUENCE: 172
MLPAPKNLVV SRVTEDSARL SWTAPDAAFD SFPIEYDEWW ALGEAITLIV PASERSYDLT   60
GLKPGTEYVV KIHGVKGGQR SYPLIAFFTT                                    90

SEQ ID NO: 173           moltype = AA  length = 88
FEATURE                  Location/Qualifiers
source                   1..88
                         mol_type = protein
                         organism = synthetic construct
SEQUENCE: 173
MLPAPKNLVV SRVTEDSARL SWTAPDAAFD SFTIHYRELY VQAIVLTVPG SERSYDLTGL   60
```

-continued

```
KPGTEYLVMI PGVKGGPTSV PLSAIFTT                                         88

SEQ ID NO: 174          moltype = AA  length = 90
FEATURE                 Location/Qualifiers
source                  1..90
                        mol_type = protein
                        organism = synthetic construct
SEQUENCE: 174
MLPAPKNLVV SRVTEDSARL SWTAPDAAFD SFFIGYLEPQ PPGEAIVLTV PGSERSYDLT      60
GLKPGTEYKV VIQGVKGGTP SEPLSAIFTT                                       90

SEQ ID NO: 175          moltype = AA  length = 90
FEATURE                 Location/Qualifiers
source                  1..90
                        mol_type = protein
                        organism = synthetic construct
SEQUENCE: 175
MLPAPKNLVV SRVTEDSARL SWTAPDAAFD SFFIGYLEPQ PPGEAIVLTV PGSERSYDLT      60
GLKPGTEYSV VIQGVKGGFP SDPLSAIFTT                                       90

SEQ ID NO: 176          moltype = AA  length = 90
FEATURE                 Location/Qualifiers
source                  1..90
                        mol_type = protein
                        organism = synthetic construct
SEQUENCE: 176
MLPAPKNLVV SRVTEDSARL SWTAPDAAFD SFPIAYAEPR PDGEAIVLTV PGSERSYDLT      60
GLKPGTEYSV GIHGVKGGHD SSPLSAIFTT                                       90

SEQ ID NO: 177          moltype = AA  length = 90
FEATURE                 Location/Qualifiers
source                  1..90
                        mol_type = protein
                        organism = synthetic construct
SEQUENCE: 177
MLPAPKNLVV SRVTEDSARL SWTAPDAAFD SFFIGYLEPQ PPGEAIVLTV PGSERSYDLT      60
GLKPGTEYNV TIQGVKGGRA SGPLSAIFTT                                       90

SEQ ID NO: 178          moltype = AA  length = 90
FEATURE                 Location/Qualifiers
source                  1..90
                        mol_type = protein
                        organism = synthetic construct
SEQUENCE: 178
MLPAPKNLVV SRVTEDSARL SWTAPDAAFD SFDIAYAEPI PRGEAIVLTV PGSERSYDLT      60
GLKPGTEYSV LIHGVKGGRR SVPLSAIFTT                                       90

SEQ ID NO: 179          moltype = AA  length = 90
FEATURE                 Location/Qualifiers
source                  1..90
                        mol_type = protein
                        organism = synthetic construct
SEQUENCE: 179
MLPAPKNLVV SRVTEDSARL SWTAPDAAFD SFYIAYAEPR PDGEAIVLTV PGSERSYDLT      60
GLKPGTEYPV PIPGVKGGPG SSPLSAIFTT                                       90

SEQ ID NO: 180          moltype = AA  length = 90
FEATURE                 Location/Qualifiers
source                  1..90
                        mol_type = protein
                        organism = synthetic construct
SEQUENCE: 180
MLPAPKNLVV SRVTEDSARL SWTAPDAAFD SFEISYYEMR GYGEAIVLTV PGSERSYDLT      60
GLKPGTEYSV LIHGVEGGDY SSPLSAISTT                                       90

SEQ ID NO: 181          moltype = AA  length = 90
FEATURE                 Location/Qualifiers
source                  1..90
                        mol_type = protein
                        organism = synthetic construct
SEQUENCE: 181
MLPAPKNLVV SHVTEDSARL SWTAPDAAFD SFPIAYAEPR PDGEAIVLTV PGSERSYDLT      60
GLKPGTEYSV LIHGVKGGLL SSPLSAIFTT                                       90

SEQ ID NO: 182          moltype = AA  length = 90
FEATURE                 Location/Qualifiers
source                  1..90
                        mol_type = protein
                        organism = synthetic construct
```

```
SEQUENCE: 182
MLPAPKNLVV SRVTEDSARL SWTAPDAAFD SFFIGYLEPY PPGEAIVLTV PGSERSYDLT    60
GLKPGTEYVV SIQGVKGGTP SQPLSAIFTT                                     90

SEQ ID NO: 183            moltype = AA   length = 90
FEATURE                   Location/Qualifiers
source                    1..90
                          mol_type = protein
                          organism = synthetic construct
SEQUENCE: 183
MLPAPKNLVV SRVTEDSARL SWTAPDAAFD SFLIPYAETS PSGEAIVLTV PGSERSYDLT    60
GLKPGTEYSV LIHGVKGGRP SNPLVAAFTT                                     90

SEQ ID NO: 184            moltype = AA   length = 90
FEATURE                   Location/Qualifiers
source                    1..90
                          mol_type = protein
                          organism = synthetic construct
SEQUENCE: 184
MLPAPKNLVV SRITEDSARL SWTAPDAAFD SFGIGYYEHK RFGEAIQLSV PGSERSYDLT    60
GLKPGTEYEV DIEGVKGGVL SWPLFAEFTT                                     90

SEQ ID NO: 185            moltype = AA   length = 90
FEATURE                   Location/Qualifiers
source                    1..90
                          mol_type = protein
                          organism = synthetic construct
SEQUENCE: 185
MLPAPKNLVV SRVTEDSARL SWTAPDAAFD SFEIDYDELA IYGEAIVLTV PGSERSYDLT    60
GLKPGTEYGV MIIGVKGGLP SDPLSAIFTT                                     90

SEQ ID NO: 186            moltype = AA   length = 87
FEATURE                   Location/Qualifiers
source                    1..87
                          mol_type = protein
                          organism = synthetic construct
SEQUENCE: 186
MLPAPKNLVV SRVTEDSARL SWTAPDAAFD SFFIGYLESA EAIVLTVPGS ERSYDLTGLK    60
PGTEYLVTIQ GVKGGIASDP LSAIFTT                                        87

SEQ ID NO: 187            moltype = AA   length = 90
FEATURE                   Location/Qualifiers
source                    1..90
                          mol_type = protein
                          organism = synthetic construct
SEQUENCE: 187
MLPAPKNLVV SRVTEDSARL SWTAPDAAFD SFVIEYFEFV GYGEAIVLTV PGSERSYDLT    60
GLKPGTEYSV GIYGVKGGKL SPPLSAIFTT                                     90

SEQ ID NO: 188            moltype = AA   length = 90
FEATURE                   Location/Qualifiers
source                    1..90
                          mol_type = protein
                          organism = synthetic construct
SEQUENCE: 188
MLPAPKNLVV SRVTEDSARL SWTAPDAAFD SFLIPYAETS PSGEAIVLTV PGSERSYDLT    60
GLKPGTEYSV LIHGVKGGKL SLPLSAIFTT                                     90

SEQ ID NO: 189            moltype = AA   length = 86
FEATURE                   Location/Qualifiers
source                    1..86
                          mol_type = protein
                          organism = synthetic construct
SEQUENCE: 189
MLPAPKNLVV SRVTEDSARL SWTAPDAAFD SFHEWVYFGE AIVLTVPGSE RSYDLTGLKP    60
GTEYFVDIWG VKGGTVSKPL SAIFTT                                         86

SEQ ID NO: 190            moltype = AA   length = 90
FEATURE                   Location/Qualifiers
source                    1..90
                          mol_type = protein
                          organism = synthetic construct
SEQUENCE: 190
MLPAPKNLVV SRVTEDSARL SWTAPDAAFD SFFIGYPEYP ATGEAITLFV PGSERSYDLT    60
GLKPGTEYNV VIQGVKGGRP SNPLVVAFTT                                     90

SEQ ID NO: 191            moltype = AA   length = 90
FEATURE                   Location/Qualifiers
source                    1..90
```

-continued

```
                              mol_type = protein
                              organism = synthetic construct
SEQUENCE: 191
MLPAPENLVV SRVTEDSARL SWTAPDAAFD SFEITYEENW RRGEAIVLTV PGSERSYDLT    60
GPKPGTEYIV IIQGVKGGAE SWPLSAIFTT                                     90

SEQ ID NO: 192        moltype = AA   length = 90
FEATURE               Location/Qualifiers
source                1..90
                      mol_type = protein
                      organism = synthetic construct
SEQUENCE: 192
MLPAPKNLVV SRVTEDSARL SWTALDAAFD SFFIGYLEPQ PPGEAIVLTV PGSERSYDLT    60
GLKPGTEYNV TIQGVKGGFP SMPLSAIFTT                                     90

SEQ ID NO: 193        moltype = AA   length = 90
FEATURE               Location/Qualifiers
source                1..90
                      mol_type = protein
                      organism = synthetic construct
SEQUENCE: 193
MLPAPKNLVV SRVTEDSARL SWTAPDAAFD SFTIWYAEAV GNGEAIVLTV PGSERSYDLT    60
GLKPGTEYWV DIWGVKGGEF SSPLSAIFTT                                     90

SEQ ID NO: 194        moltype = AA   length = 90
FEATURE               Location/Qualifiers
source                1..90
                      mol_type = protein
                      organism = synthetic construct
SEQUENCE: 194
MLPAPKNLVV SRVTEDSARL SWTAPDAAFD SFEIDYDELA IYGEAIVLTV PGSERSYDLT    60
GLKPGTEYRV FIYGVKGGWT SWPLSTIFTT                                     90

SEQ ID NO: 195        moltype = AA   length = 90
FEATURE               Location/Qualifiers
source                1..90
                      mol_type = protein
                      organism = synthetic construct
SEQUENCE: 195
MLPAPKNLVV SRVTEDSARL SWTAPDAAFD SFPIEYDEIP FWGEAIVLTV PGSERSYDLT    60
GLKPGTEYRV WIHGVKGGNS SWPLSAIFTT                                     90

SEQ ID NO: 196        moltype = AA   length = 90
FEATURE               Location/Qualifiers
source                1..90
                      mol_type = protein
                      organism = synthetic construct
SEQUENCE: 196
MLPAPKNLVV SRVTEDSARL SWTAPDAAFD SFNIHYVEWW VLGEAIVLTV PGSERSYDLT    60
GLKPGTEYPV YIYGVKGGPK SIPLSAIFTT                                     90

SEQ ID NO: 197        moltype = AA   length = 90
FEATURE               Location/Qualifiers
source                1..90
                      mol_type = protein
                      organism = synthetic construct
SEQUENCE: 197
MLPAPKNLVV SRVTEDSARL SWTAPDAAFD SFKIDYLEIN DNGEAIVLTV PGSERSYDLT    60
GLKPGTEYPV YIWGVKGGYP SSPLSAIFTT                                     90

SEQ ID NO: 198        moltype = AA   length = 90
FEATURE               Location/Qualifiers
source                1..90
                      mol_type = protein
                      organism = synthetic construct
SEQUENCE: 198
MLPAPKNLVV SRVTEDSARL SWTAPDAAFD SFLIAYNEDR KFGEAIVLTV PGSERSYDLT    60
GLKPGTEYDV WIEGVKGGSL SFPLSAIFTT                                     90

SEQ ID NO: 199        moltype = AA   length = 90
FEATURE               Location/Qualifiers
source                1..90
                      mol_type = protein
                      organism = synthetic construct
SEQUENCE: 199
MLPAPKNLVV SRVTEDSARL SWTAPDAAFD SFGIRYFEWW DLGEAIVLTV PGSERSYDPT    60
GLKPGTEYNV TIQGVKGGFP SMPLSAIFTT                                     90

SEQ ID NO: 200        moltype = AA   length = 90
```

-continued

```
FEATURE                  Location/Qualifiers
source                   1..90
                         mol_type = protein
                         organism = synthetic construct
SEQUENCE: 200
MLPAPKNLVV SRVTEDSARL SWTAPDAAFD SFYIEYYEWM HTGEAIVLTV PGSERSYDLT   60
GLKPGTEYSV YIYGVKGGYP SSPLSAIFTT                                   90

SEQ ID NO: 201           moltype = AA  length = 90
FEATURE                  Location/Qualifiers
source                   1..90
                         mol_type = protein
                         organism = synthetic construct
SEQUENCE: 201
MLPAPKNLVV SRVTEDSARL SWTAPDAAFD SFNIDYWETW VIGEAIVLTV PGSERSYDLT   60
GLKPGTEYEV IIPGVKGGTI SPPLSAIFTT                                   90

SEQ ID NO: 202           moltype = AA  length = 90
FEATURE                  Location/Qualifiers
source                   1..90
                         mol_type = protein
                         organism = synthetic construct
SEQUENCE: 202
MLPAPKNLVV SRVTEDSARL SWTAPDAAFD SFYIDYLELT YSGEAIVLTV PGSERSYDLT   60
GLKPGTEYYV YIYGVKGGYP SSPLSAIFTT                                   90

SEQ ID NO: 203           moltype = AA  length = 90
FEATURE                  Location/Qualifiers
source                   1..90
                         mol_type = protein
                         organism = synthetic construct
SEQUENCE: 203
MLPAPKNLVV SRVTEDSARL SWTAPDAALD SFRIEYYESY GHGEAIVLTV PGSERSYDLT   60
GLKPGTEYDV GIYGVKGGYY SRPLSAIFTT                                   90

SEQ ID NO: 204           moltype = AA  length = 90
FEATURE                  Location/Qualifiers
source                   1..90
                         mol_type = protein
                         organism = synthetic construct
SEQUENCE: 204
MLPAPKNLVV SRVTEDSARL PWTAPDAAFD SFWISYYESV GYGEAIVLTV PGSERSYDLT   60
GLKPGTEYYV DISGVKGGVY SLPLSAIFTT                                   90

SEQ ID NO: 205           moltype = AA  length = 90
FEATURE                  Location/Qualifiers
source                   1..90
                         mol_type = protein
                         organism = synthetic construct
SEQUENCE: 205
MLPAPKNLVV SRVTEDSARL SWTAPDAAFD SFDIDYDEPA WNGEAIVLTV PGSERSYDLT   60
GLKPGTEYRV FIYGVKGGNT SWPLSAIFTT                                   90

SEQ ID NO: 206           moltype = AA  length = 90
FEATURE                  Location/Qualifiers
source                   1..90
                         mol_type = protein
                         organism = synthetic construct
SEQUENCE: 206
MLPAPKNLVV SRVTEDSARL SWTAPDAAFD SFDIEYDELW KNGEAIVLTV PGSERSYDLT   60
GLKPGTEYRV FIYGVKGGYG SFPLSAIFTT                                   90

SEQ ID NO: 207           moltype = AA  length = 90
FEATURE                  Location/Qualifiers
source                   1..90
                         mol_type = protein
                         organism = synthetic construct
SEQUENCE: 207
MLPAPKNLVV SRVTEDSARL SWTAPDAAFD SFFIGYLEPQ PPGEAIVLTV PGSERSYDLT   60
GLKPGTEYNV TIQGVKGGTP SEPLSAISTT                                   90

SEQ ID NO: 208           moltype = AA  length = 90
FEATURE                  Location/Qualifiers
source                   1..90
                         mol_type = protein
                         organism = synthetic construct
SEQUENCE: 208
MLPAPKNLVV SRVTEDSARL SWTAPDAAFD SFGIVYREPY VGGEAIVLTV PGSERSYDLT   60
GLKPGTEYGV PIPGVKGGYD SGPLSAIFTT                                   90
```

-continued

```
SEQ ID NO: 209              moltype = AA   length = 90
FEATURE                     Location/Qualifiers
source                      1..90
                            mol_type = protein
                            organism = synthetic construct
SEQUENCE: 209
MLPAPKNLVV SRVTEDSARL SWTAPDAAFD SFTIPYIEYV WWGEAIVLTV QGSERSYDLT    60
GLKPGTEYPV TIGGVKGGSR SHPLHAHFTT                                     90

SEQ ID NO: 210              moltype = AA   length = 90
FEATURE                     Location/Qualifiers
source                      1..90
                            mol_type = protein
                            organism = synthetic construct
SEQUENCE: 210
MLPAPKNLVV SRVTEDSARL SWTAPDAAFD SFSIVYGERF VNGEAIVLTV PGSERSYDLT    60
GLKPGTEYHV YIDGVKGGDL SWPLSAIFTT                                     90

SEQ ID NO: 211              moltype = AA   length = 90
FEATURE                     Location/Qualifiers
source                      1..90
                            mol_type = protein
                            organism = synthetic construct
SEQUENCE: 211
MLPAPKNLVV SRVTEDSARL SWTAPDAAFD SFWINYYEAQ PDGEAIVLTV PGSERSYDLT    60
GLKPGTEYDV EIAGVKGGTA SLPLSAIFTT                                     90

SEQ ID NO: 212              moltype = AA   length = 90
FEATURE                     Location/Qualifiers
source                      1..90
                            mol_type = protein
                            organism = synthetic construct
SEQUENCE: 212
MLPAPKNLVV SRVTEDSARL SWTAPDAAFD SFIIEYWEQI GVGEAIVLTV PGSERSYDLT    60
GLKPGTEYWV GIYGVKGGLL SSPLSAIFTT                                     90

SEQ ID NO: 213              moltype = AA   length = 90
FEATURE                     Location/Qualifiers
source                      1..90
                            mol_type = protein
                            organism = synthetic construct
SEQUENCE: 213
MLPAPKNLVV SRVTEDSARL SWTAPDAAFD SFWIYYWEIE RAGEAIRLDV PGSERSYDLT    60
GLKPGTEYRV DIWGVKGGPT SGPLRATFTT                                     90

SEQ ID NO: 214              moltype = AA   length = 90
FEATURE                     Location/Qualifiers
source                      1..90
                            mol_type = protein
                            organism = synthetic construct
SEQUENCE: 214
MLPAPKNLVV SRVTEDSARL SWTAPDAAFD SFAIPYGERQ ELGEAIVLTV PGSERSYDLT    60
GLKPGTEYFV VIQGVKGGQP SYPLSAIFTT                                     90

SEQ ID NO: 215              moltype = AA   length = 90
FEATURE                     Location/Qualifiers
source                      1..90
                            mol_type = protein
                            organism = synthetic construct
SEQUENCE: 215
MLPAPKNLVV SRVTEDSARL SWTAPDAAFD SFLIPYAETS PTGEAIVLTV PGSERSYDLT    60
GLKPGTEYSV LIHGVKGGYP SSPLSAIFTT                                     90

SEQ ID NO: 216              moltype = AA   length = 90
FEATURE                     Location/Qualifiers
source                      1..90
                            mol_type = protein
                            organism = synthetic construct
SEQUENCE: 216
MLPAPKNLVV SRVTEDSARL SWTAPDAAFD SFPIAYAEPT PSGEAIVLTV PGSERSYDLT    60
GLKPGTEYSV LIHGVKGGGL SLPLSAIFTT                                     90

SEQ ID NO: 217              moltype = AA   length = 90
FEATURE                     Location/Qualifiers
source                      1..90
                            mol_type = protein
                            organism = synthetic construct
SEQUENCE: 217
```

-continued

```
MLPAPKNLVV SRVTEDSARL SWTAPDAAFD SFIIEYWEWY FAGEAIVLTV PGSERSYDLT   60
GLKPGTEYTV WITGVKGGTW SEPLSAIFTT                                   90

SEQ ID NO: 218          moltype = AA  length = 90
FEATURE                 Location/Qualifiers
source                  1..90
                        mol_type = protein
                        organism = synthetic construct
SEQUENCE: 218
MLPAPKNLVV SRVTEDSARL SWTAPDAAFD SFTILYYEMV GEGEAIVLTV PGSERSYDLT   60
GPKPGTEYWV DIYGVKGGGW SRPLSAIFTT                                   90

SEQ ID NO: 219          moltype = AA  length = 90
FEATURE                 Location/Qualifiers
source                  1..90
                        mol_type = protein
                        organism = synthetic construct
SEQUENCE: 219
MLPAPKNLVV SRVTEDSARL SWTAPDAAFD SFHIDYLELT YAGEAIVLTV PGSERSYDLT   60
GLKPGTEYYV TIYGVKGGYP SSPLSAIFTT                                   90

SEQ ID NO: 220          moltype = AA  length = 90
FEATURE                 Location/Qualifiers
source                  1..90
                        mol_type = protein
                        organism = synthetic construct
SEQUENCE: 220
MLPAPKNLVV SRVTEDSARL SWTAPDAAFD SFHIIYEEDG TEGEAIYLRV PGSERSYDLT   60
GLKPGTEYEV DIEGVKGGVL SWPLFAEFTT                                   90

SEQ ID NO: 221          moltype = AA  length = 90
FEATURE                 Location/Qualifiers
source                  1..90
                        mol_type = protein
                        organism = synthetic construct
SEQUENCE: 221
MLPAPKNLVV SRVTEDSARL SWTAPDAAFD SFHISYQEVV AEGEAIYLRV PGSERSYDLT   60
GLKPGTEYYV LIHGVKGGYE SKPLDASFTT                                   90

SEQ ID NO: 222          moltype = AA  length = 90
FEATURE                 Location/Qualifiers
source                  1..90
                        mol_type = protein
                        organism = synthetic construct
SEQUENCE: 222
MLPAPKNLVV SRVTEDSARL SWTAPDAAFD SFYIEYFEWT GSGEAIVLTV PGSERSYDLT   60
GLKPGTEYNV AIYGVKGGAV SYPLSAIFTT                                   90

SEQ ID NO: 223          moltype = AA  length = 90
FEATURE                 Location/Qualifiers
source                  1..90
                        mol_type = protein
                        organism = synthetic construct
SEQUENCE: 223
MLPAPKNLVV SRVTEDSARL SWTAPDAAFD SFTIWYAEAL GDGEAIVLTV PGSERSYDLT   60
GLKPGTEYFV DIPGVKGGTR SSPLSAISTT                                   90

SEQ ID NO: 224          moltype = AA  length = 88
FEATURE                 Location/Qualifiers
source                  1..88
                        mol_type = protein
                        organism = synthetic construct
SEQUENCE: 224
MLLAPKNLVV SRVTEDSARL SWTAPDAAFD SFRYLEQGLY GEAIVLTVPG SERSYDLTGL   60
KPGTEYWVEI IGVKGGEYST PLSAIFTT                                     88

SEQ ID NO: 225          moltype = AA  length = 90
FEATURE                 Location/Qualifiers
source                  1..90
                        mol_type = protein
                        organism = synthetic construct
SEQUENCE: 225
MLPAPKNLVV SRVTEDSARL SWTAPDAAFD SFKIEYFEYV GYGEAIVLTV PGSERSYDLT   60
GLKPGTEYYV AIYGVKGGWY SRPLSAIFTT                                   90

SEQ ID NO: 226          moltype = AA  length = 90
FEATURE                 Location/Qualifiers
source                  1..90
                        mol_type = protein
```

-continued

```
                              organism = synthetic construct
SEQUENCE: 226
MLPAPKNLVV SRVTEDSARL SWTAPDAAFD SFHIIYEEVL TEGEAIYLRV PGSERSYDLT   60
GLKPGTEYGV TIKGVKGGAY SIPLIATFTT                                    90

SEQ ID NO: 227              moltype = AA  length = 90
FEATURE                     Location/Qualifiers
source                      1..90
                            mol_type = protein
                            organism = synthetic construct
SEQUENCE: 227
MLPAPKNLVV SRVTEDSARL SWTAPDAAFD SFRIRYLEWW NIGEAIVLTV PGSERSYDLT   60
GLKPGTEYHV DIWGVKGGYS SYPLSAIFTT                                    90

SEQ ID NO: 228              moltype = AA  length = 90
FEATURE                     Location/Qualifiers
source                      1..90
                            mol_type = protein
                            organism = synthetic construct
SEQUENCE: 228
MLPAPKNLVV SRVTEDSARL SWTAPDAAFD SFEIYYVEWS EAGEAIVLTV PGSERSYDLT   60
GLKPGTEYRV EIRGVKGGSW SSPLSAIFTT                                    90

SEQ ID NO: 229              moltype = AA  length = 90
FEATURE                     Location/Qualifiers
source                      1..90
                            mol_type = protein
                            organism = synthetic construct
SEQUENCE: 229
MLPAPKNLVV SRVTEDSARL SWTAPDAAFD SFSIHYDEDW RRGEAIVLTV PGSERSYDLT   60
GLKPGTEYLV EIPGVKGGKA SYPLSAIFTT                                    90

SEQ ID NO: 230              moltype = AA  length = 90
FEATURE                     Location/Qualifiers
source                      1..90
                            mol_type = protein
                            organism = synthetic construct
SEQUENCE: 230
MLPAPKNLVV SRVTEDSARL SWTAPDAAFD SFQIRYPKRW ISGEAIVLTV PGSERSYDLT   60
GLKPGTEYEV VIRGVKGGEY SWPLSAIFTT                                    90

SEQ ID NO: 231              moltype = AA  length = 90
FEATURE                     Location/Qualifiers
source                      1..90
                            mol_type = protein
                            organism = synthetic construct
SEQUENCE: 231
MLPAPKNLVV SRVTEDSARL SWTAPDAAFD SFEIPYIETV ALGEAIVLTV PGSERSYDLT   60
GLKPGTEYYV EIYGVKGGSY SYPLSAISTT                                    90

SEQ ID NO: 232              moltype = AA  length = 90
FEATURE                     Location/Qualifiers
source                      1..90
                            mol_type = protein
                            organism = synthetic construct
SEQUENCE: 232
MLPAPKNLVV SRVTEDSARL SWTAPDAAFD SFTIAYDETL NLGEAIVLTV PGSERSYDLT   60
GLKPGTEYIV GIFGVKGGTH SWPLSAIFTT                                    90

SEQ ID NO: 233              moltype = AA  length = 90
FEATURE                     Location/Qualifiers
source                      1..90
                            mol_type = protein
                            organism = synthetic construct
SEQUENCE: 233
MLPAPKNLVV SRVTEDSARL SWTAPDAAFD SFYIVYAEPI PNGEAIVLTV PGSERSYDLT   60
GLKPGTEYSV LIHGVKGGRN SDPLSAIFTT                                    90

SEQ ID NO: 234              moltype = AA  length = 90
FEATURE                     Location/Qualifiers
source                      1..90
                            mol_type = protein
                            organism = synthetic construct
SEQUENCE: 234
MLPAPKNLVV SRVTEDSARL SWTAPDAAFD SFYITYWETW DYGEAIVLTV PGSERSYDLT   60
GLKPGTEYKV PITGVKGGGP SVPLSAIFTT                                    90

SEQ ID NO: 235              moltype = AA  length = 90
FEATURE                     Location/Qualifiers
```

-continued

```
source                     1..90
                           mol_type = protein
                           organism = synthetic construct
SEQUENCE: 235
MLPAPKNLVV SRVTEDSARL SWTAPDAAFD SFSINYREWW SDGEAIYLPV PGSERSYDLT   60
GLKPGTEYAV YIQGVKGGSR SFPLHAWFTT                                    90

SEQ ID NO: 236             moltype = AA  length = 90
FEATURE                    Location/Qualifiers
source                     1..90
                           mol_type = protein
                           organism = synthetic construct
SEQUENCE: 236
MLPAPKNLVV SRVTEDSARL SWTAPDAAFD SFWIEYYEEL GSGEAIVLTV PGSERSYDLT   60
GLKPGTEYRV YIYGVKGGYP SSPLSAIFTT                                    90

SEQ ID NO: 237             moltype = AA  length = 90
FEATURE                    Location/Qualifiers
source                     1..90
                           mol_type = protein
                           organism = synthetic construct
SEQUENCE: 237
MLPAPKNLVV SRVTEDSARL SWTAPDAAFD SFTILYGEMG TTGEAIVLTV PGSERSYDLT   60
GLKPGTEYDV FIEGVKGGEL SWPLSAIFTT                                    90

SEQ ID NO: 238             moltype = AA  length = 88
FEATURE                    Location/Qualifiers
source                     1..88
                           mol_type = protein
                           organism = synthetic construct
SEQUENCE: 238
MLPAPKNLVV SRVTEDSARL SWTAPDAAFD SFKIFYQEFG GEAIVLTVPG SERSYDLTGL   60
KPGTEYWVDI YGVKGGYTSS PLSAIFTT                                      88

SEQ ID NO: 239             moltype = AA  length = 90
FEATURE                    Location/Qualifiers
source                     1..90
                           mol_type = protein
                           organism = synthetic construct
SEQUENCE: 239
MLPAPKNLVV SRVTEDSARL SWTAPDAAFD SFAITYYEGR WRGEAIVLTV PGSERSYDLT   60
GLKPGTEYGV PIRGVKGGTG SLPLSAIFTT                                    90

SEQ ID NO: 240             moltype = AA  length = 90
FEATURE                    Location/Qualifiers
source                     1..90
                           mol_type = protein
                           organism = synthetic construct
SEQUENCE: 240
MLPAPKNLVV SRVTEDSARL SWTAPDAAFD SFRIKYLEWW LGGEAIVLTV PGSERSYDLT   60
GLKPGTEYWV DIQGVKGGVL SWPLSAIFTT                                    90

SEQ ID NO: 241             moltype = AA  length = 90
FEATURE                    Location/Qualifiers
source                     1..90
                           mol_type = protein
                           organism = synthetic construct
SEQUENCE: 241
MLPAPKNLVV SRVTEDSARL SWTAPDAAFD SFNIYYYEWF VSGEAIVLTV PGSERSYDLT   60
GLKPGTEYFV DIDGVKGGYR SRPLSAIFTT                                    90

SEQ ID NO: 242             moltype = AA  length = 90
FEATURE                    Location/Qualifiers
source                     1..90
                           mol_type = protein
                           organism = synthetic construct
SEQUENCE: 242
MLPAPKNLVV SRVTEDSARL SWTAPDAAFD SFPIKYLEWW SWGEAIVLTV PGSERSYDLT   60
GLKPGTEYRV PISGVKGGGM SGPLSAIFTT                                    90

SEQ ID NO: 243             moltype = AA  length = 90
FEATURE                    Location/Qualifiers
source                     1..90
                           mol_type = protein
                           organism = synthetic construct
SEQUENCE: 243
MLPAPKNLVV SRVTEDSARL SWTAPDAAFD SFAIPYYEWV NHGEAIVLTV PGSERSYDLT   60
GLKPGTEYPV GIDGVKGGGP SWPLSAIFTT                                    90
```

-continued

```
SEQ ID NO: 244            moltype = AA  length = 89
FEATURE                   Location/Qualifiers
source                    1..89
                          mol_type = protein
                          organism = synthetic construct
SEQUENCE: 244
MLPAPKNLVV SRVTEDSARL SWTAPDAAFD SFHIDYSEFH LRGEAIVLTV PGSERSYDLT  60
GLKPGTEYLG IFGVKGGEQS GPLSAIFTT                                    89

SEQ ID NO: 245            moltype = AA  length = 90
FEATURE                   Location/Qualifiers
source                    1..90
                          mol_type = protein
                          organism = synthetic construct
SEQUENCE: 245
MLPAPKNLVV SRITEDSARL SWTAPDAAFD SFGIAYNEGD HYGEAIVLTV PGSERSYDLT  60
GLKPGTEYSV WIEGVKGGNL SYPLSAIFTT                                   90

SEQ ID NO: 246            moltype = AA  length = 90
FEATURE                   Location/Qualifiers
source                    1..90
                          mol_type = protein
                          organism = synthetic construct
SEQUENCE: 246
MLPAPKNLVV SRVTEDSARL SWTAPDAAFD SFTIAYNEQN HYGEAIVLTV PGSERSYDLT  60
GLKPGTEYGV WIEGVKGGTL SWPLSAIFTT                                   90

SEQ ID NO: 247            moltype = AA  length = 87
FEATURE                   Location/Qualifiers
source                    1..87
                          mol_type = protein
                          organism = synthetic construct
SEQUENCE: 247
MLPAPKNLVV SRVTEDSARL SWTAPDAAFD SFYIEWTYKG EAIVLTVPGS ERSYDLTGLK  60
PGTEYFVGIP GVKGGKSSYP LSAIFTT                                      87

SEQ ID NO: 248            moltype = AA  length = 92
FEATURE                   Location/Qualifiers
source                    1..92
                          mol_type = protein
                          organism = synthetic construct
SEQUENCE: 248
MGSLPAPKNL VVSRVTEDSA RLSWTAPDAA FDSFAIPYAE PSPTGEAIVL TVPGSERSYD  60
LTGLKPGTEY PVWIQGVKGG SPSAPLSAEF TT                                92

SEQ ID NO: 249            moltype = AA  length = 90
FEATURE                   Location/Qualifiers
source                    1..90
                          mol_type = protein
                          organism = synthetic construct
SEQUENCE: 249
MLPAPKNLVV SRVTEDSARL SWTAPDAAFD SFSIDYFESV GFGEAIVLTV PGSERSYDLT  60
GLKPGTEYDV QITGVKGGPH SLPLSAIFTT                                   90

SEQ ID NO: 250            moltype = AA  length = 90
FEATURE                   Location/Qualifiers
source                    1..90
                          mol_type = protein
                          organism = synthetic construct
SEQUENCE: 250
MLPAPKNLVV SRVTEDSARL SWTAPDAAFD SFFIGYLEPY PPGEAIVLTV PGSERSYDLT  60
GLKPGTEYAV EIAGVKGGLL SSPLSAISTT                                   90

SEQ ID NO: 251            moltype = AA  length = 90
FEATURE                   Location/Qualifiers
source                    1..90
                          mol_type = protein
                          organism = synthetic construct
SEQUENCE: 251
MLPAPKNLVV SRVTEDSARL SWTAPDAAFD SFFIGYLEPQ PPGEAIVLTV PGSERSYDLT  60
GLKPGTEYNV TIQGVKGGFP SMPLSAIVTT                                   90

SEQ ID NO: 252            moltype = AA  length = 90
FEATURE                   Location/Qualifiers
source                    1..90
                          mol_type = protein
                          organism = synthetic construct
SEQUENCE: 252
MLPAPKNLVV SRVTEDSARL SWTAPDAAFD SFDIGYTEYG GYGEAIVLTV PGSERSYDLT  60
```

-continued

```
GLKPGTEYWV LIQGVKGGGS SVPLSAIFTT                                        90

SEQ ID NO: 253          moltype = AA  length = 90
FEATURE                 Location/Qualifiers
source                  1..90
                        mol_type = protein
                        organism = synthetic construct
SEQUENCE: 253
MLPAPKNLVV SRVTEDSARL SWTAPDAAFD SFTIEYWETI GGGEAIVLTV PGSERSYDLT       60
GLKPGTEYYV GIYGVKGGWW SRPLSAIFTT                                        90

SEQ ID NO: 254          moltype = AA  length = 90
FEATURE                 Location/Qualifiers
source                  1..90
                        mol_type = protein
                        organism = synthetic construct
SEQUENCE: 254
MLPAPKNLVV SRVTEDSARL SWTAPDAAFD SFFIPYAEPS PTGEAIVLTV PGSERSYDLT       60
GLKPGTEYSV LIHGVKGGHL SDPLSAISTT                                        90

SEQ ID NO: 255          moltype = AA  length = 90
FEATURE                 Location/Qualifiers
source                  1..90
                        mol_type = protein
                        organism = synthetic construct
SEQUENCE: 255
MLPAPKNLVV SRVTEDSARL SWTAPDAAFD SFDIEYYELI GRGEAIVLTV PGSERSYDLT       60
GLKPGTEYWV GIYGVKGGWL SRPLSAIFTT                                        90

SEQ ID NO: 256          moltype = AA  length = 90
FEATURE                 Location/Qualifiers
source                  1..90
                        mol_type = protein
                        organism = synthetic construct
SEQUENCE: 256
MLPAPKNLVV SRVTEDSARL SWTAPDAAFD SFHIVYHEPR PSGEAIVLTV PGSERSYDLT       60
GLKPGTEYEV GIVGVKGGDL SVPLSAIFTT                                        90

SEQ ID NO: 257          moltype = AA  length = 90
FEATURE                 Location/Qualifiers
source                  1..90
                        mol_type = protein
                        organism = synthetic construct
SEQUENCE: 257
MLPAPKNLVV SRVTEDSARL SWTAPDAAFD SFHIVYHEPR PSGEAIVLTV PGSERSYDLT       60
GLKPGTEYEV GIVSVKGGDL SVPLSAIFTT                                        90

SEQ ID NO: 258          moltype = AA  length = 90
FEATURE                 Location/Qualifiers
source                  1..90
                        mol_type = protein
                        organism = synthetic construct
SEQUENCE: 258
MLPAPKNLVV SRVTEDSARL SWTAPDAAFD SFFIPYAEPS PTGEAIVLTV PGSERSYDLT       60
GLKPGTEYDV WIEGVKGGVL SWPLSAIFTT                                        90

SEQ ID NO: 259          moltype = AA  length = 90
FEATURE                 Location/Qualifiers
source                  1..90
                        mol_type = protein
                        organism = synthetic construct
SEQUENCE: 259
MLPAPKNLVV SRVTEDSARL SWTAPDAAFD SFTIEYFEFV DAGEAIVLTV PGSERSYDLT       60
GLKPGTEYWV EIWGVKGGSW SKPLSAIFTT                                        90

SEQ ID NO: 260          moltype = AA  length = 89
FEATURE                 Location/Qualifiers
source                  1..89
                        mol_type = protein
                        organism = synthetic construct
SEQUENCE: 260
MLPAPKNLVV SRVTEDSARL SWTAPDAAFD SFNISYYEYF VHGEAIVLTV PGSERSYDLT       60
GLKPGTEYYV IDGVKGGDPS EPLSAIFTT                                         89

SEQ ID NO: 261          moltype = AA  length = 90
FEATURE                 Location/Qualifiers
source                  1..90
                        mol_type = protein
                        organism = synthetic construct
```

-continued

```
SEQUENCE: 261
MLPAPKNLVV SRVTEDSARL SWTAPDAAFD SFTIVYGEWG VPGEAIVLTV PGSERSYDLT    60
GLKPGTEYDV WIEGVKGGDL SWPLSAIVTT                                     90

SEQ ID NO: 262            moltype = AA   length = 90
FEATURE                   Location/Qualifiers
source                    1..90
                          mol_type = protein
                          organism = synthetic construct
SEQUENCE: 262
MLPAPKNLVV SRVTEDSARL SWTAPDAAFD SFAIEYFEYT GEGEAIVLTV PGSERSYDLT    60
GLKPGTEYYV GIYGVKGGYL SRPLSAIFTT                                     90

SEQ ID NO: 263            moltype = AA   length = 90
FEATURE                   Location/Qualifiers
source                    1..90
                          mol_type = protein
                          organism = synthetic construct
SEQUENCE: 263
MLPAPKNLVV SRVTEDSARL SWTAPDAAFD SFFIGYLEPQ PPGEAIVLTV PGSERSYDLT    60
GLKPGTEYNV TIQGVKGGFP SMPLSAISTT                                     90

SEQ ID NO: 264            moltype = AA   length = 90
FEATURE                   Location/Qualifiers
source                    1..90
                          mol_type = protein
                          organism = synthetic construct
SEQUENCE: 264
MLPAPKNLVV SRVTEDSARL SWTAPDAAFD SFRIKYQEWW VEGEAIVLTV PGSERSYDLT    60
GLKPGTEYVV QIAGVKGGLS SYPLSAIFTT                                     90

SEQ ID NO: 265            moltype = AA   length = 90
FEATURE                   Location/Qualifiers
source                    1..90
                          mol_type = protein
                          organism = synthetic construct
SEQUENCE: 265
MLPAPKNLVV SRVTEDSARL SWTAPDAAFD SFWIYYIETS HQGEAIVLTV PGSERSYDLT    60
GLKPGTEYFV LIKGVKGGYD SVPLSAIFTT                                     90

SEQ ID NO: 266            moltype = AA   length = 90
FEATURE                   Location/Qualifiers
source                    1..90
                          mol_type = protein
                          organism = synthetic construct
SEQUENCE: 266
MLPAPKNLVV SRVTEDSARL SWTAPDAAFD SFMIRYQEGT RWGEAIVLTV PGSERSYDLT    60
GLKPGTEYIV MIAGVKGGQI SLPLSAIFTT                                     90

SEQ ID NO: 267            moltype = AA   length = 90
FEATURE                   Location/Qualifiers
source                    1..90
                          mol_type = protein
                          organism = synthetic construct
SEQUENCE: 267
MLPAPKNLVV SRVTEDSARL SWTAPDAAFD SFPIVYSEIH VIGEAIVLTV PGSERSYDLT    60
GLKPGTEYDV WIEGVKGGHL SEPLSAIFTT                                     90

SEQ ID NO: 268            moltype = AA   length = 90
FEATURE                   Location/Qualifiers
source                    1..90
                          mol_type = protein
                          organism = synthetic construct
SEQUENCE: 268
MLPAPKNLVV SRVTEDSARL SWTAPDAAFD SFTIVYGEAG AFGEAIVLTV PGSERSYDLT    60
GLKPGTEYDV LIEGVKGGNL SWPLSAIFTT                                     90

SEQ ID NO: 269            moltype = AA   length = 90
FEATURE                   Location/Qualifiers
source                    1..90
                          mol_type = protein
                          organism = synthetic construct
SEQUENCE: 269
MLPAPKNLVV SRVTEDSARL SWTAPDAAFD SFHINYAEVY TKGEAILLTV PGSERSYDLT    60
GLKPGTEYEV YIPGVKGGPF SRPLNAQFTT                                     90

SEQ ID NO: 270            moltype = AA   length = 90
FEATURE                   Location/Qualifiers
source                    1..90
```

-continued

```
                                 mol_type = protein
                                 organism = synthetic construct
SEQUENCE: 270
MLPAPKNLVV SRVTEDSARL SWTAPDAAFD SFLIRYQEWQ RWGEAIVLTV PGSERSYDLT   60
GLKPGTEYTV HIAGVKGGML SLPLSAIFTT                                    90

SEQ ID NO: 271          moltype = AA   length = 90
FEATURE                 Location/Qualifiers
source                  1..90
                        mol_type = protein
                        organism = synthetic construct
SEQUENCE: 271
MLPAPKNLVV SRVTEDSARL SWTAPDAAFD SFYIPYAETR DDGEAIVLTV PGSERSYDLT   60
GLKPGTEYSV LIHGVKGGDL SSPLSAIFTT                                    90

SEQ ID NO: 272          moltype = AA   length = 90
FEATURE                 Location/Qualifiers
source                  1..90
                        mol_type = protein
                        organism = synthetic construct
SEQUENCE: 272
MLPAPKNLVV SRVTEDSARL SWTAPDAAFD SFGIPYAEST PTGEAIVLTV PGSERSYDLT   60
GLKPGTEYSV LIHGVKGGHL SDPLSAIFTT                                    90

SEQ ID NO: 273          moltype = AA   length = 85
FEATURE                 Location/Qualifiers
source                  1..85
                        mol_type = protein
                        organism = synthetic construct
SEQUENCE: 273
MLPAPKNLVV SRVTEDSARL SWTAPDAAFD SFTIFKDGEA IVLTVPGSER SYDLTGLKPG   60
TEYYVYIYGV KGGYPSKPLS AIFTT                                         85

SEQ ID NO: 274          moltype = AA   length = 90
FEATURE                 Location/Qualifiers
source                  1..90
                        mol_type = protein
                        organism = synthetic construct
SEQUENCE: 274
MLPAPKNLVV SRVTEDSVRL SWTAPDAAFD SFAISYEEWW VHGEAIVLTV PGSERSYDLT   60
GLKPGTEYSV VIPGVKGGLY SWTLSAISTT                                    90

SEQ ID NO: 275          moltype = AA   length = 90
FEATURE                 Location/Qualifiers
source                  1..90
                        mol_type = protein
                        organism = synthetic construct
SEQUENCE: 275
MLPAPKNLVV SRVTEDSARL SWTAPDAAFD SFLIAYAEVT LHGEAIVLTV PGSERSYDLT   60
GLKPGTEYSV LIHGVKGGRN SDPLSAIFTT                                    90

SEQ ID NO: 276          moltype = AA   length = 90
FEATURE                 Location/Qualifiers
source                  1..90
                        mol_type = protein
                        organism = synthetic construct
SEQUENCE: 276
MLPAPKNLVV SRVTEDSARL SWTAPDAAFD SFRIDYLELT SLGEAIVLTV PGSERSYDLT   60
GLKPGTEYPV PILGVKGGLS SWPLSAIFTT                                    90

SEQ ID NO: 277          moltype = AA   length = 90
FEATURE                 Location/Qualifiers
source                  1..90
                        mol_type = protein
                        organism = synthetic construct
SEQUENCE: 277
MLPAPKNLVV SRVTEDSARL SWTAPDAAFD SFWINYYEGI GEGEAIVLTV PGSERSYDLT   60
GLKPGTEYYV DISGVKGGSY SLPLSAIFTT                                    90

SEQ ID NO: 278          moltype = AA   length = 90
FEATURE                 Location/Qualifiers
source                  1..90
                        mol_type = protein
                        organism = synthetic construct
SEQUENCE: 278
MLPAPKNLVV SRVTEDSARL SWTAPDAAFD SFPIAYAEPR PDGEAIVLTV PGSERSYDLT   60
GLKPGTEYSV LIHGVKGGHL SDPLSAIFTT                                    90

SEQ ID NO: 279          moltype = AA   length = 90
```

-continued

```
FEATURE                 Location/Qualifiers
source                  1..90
                        mol_type = protein
                        organism = synthetic construct
SEQUENCE: 279
MLPAPKNLVV SRVTEDSARL SWTAPDAAFD SFSIEYYESV GLGEAIVLTV PGSERSYDLT    60
GLKPGTEYDV SIYGVKGGYL SRPLSAIFTT                                      90

SEQ ID NO: 280          moltype = AA  length = 90
FEATURE                 Location/Qualifiers
VARIANT                 12
                        note = Xaa can be any naturally occurring amino acid
source                  1..90
                        mol_type = protein
                        organism = synthetic construct
SEQUENCE: 280
MLPAPKNLVV RXVTEDSARL SWTAPDAAFD SFEIEYDEPY RGGEAIVLTV PGSERSYDLT    60
SLKPGTEYPV SIGGVKGGIT SDPLSAIFTT                                      90

SEQ ID NO: 281          moltype = AA  length = 90
FEATURE                 Location/Qualifiers
source                  1..90
                        mol_type = protein
                        organism = synthetic construct
SEQUENCE: 281
MLPAPKNLVV SRVTEDSARL SWTAPDAAFD SFYIDYDEIH DWGEAIVLTV PGSERSYDLT    60
GLKPGTEYAV QIGGVKGGSF SWTLSAIFTT                                      90

SEQ ID NO: 282          moltype = AA  length = 90
FEATURE                 Location/Qualifiers
source                  1..90
                        mol_type = protein
                        organism = synthetic construct
SEQUENCE: 282
MLPAPKNLVV SRVTEDSARL SWTAPDAAFD SFAIVYHEPR PDGEAIVLTV PGSERSYDLT    60
GLKPGTEYEV VILGVKGGVH SYPLSAIFTT                                      90

SEQ ID NO: 283          moltype = AA  length = 90
FEATURE                 Location/Qualifiers
source                  1..90
                        mol_type = protein
                        organism = synthetic construct
SEQUENCE: 283
MLPAPKNLVV SRVTEDSARL SWTAPDAAFD SFPIAYAEPR PDGEAIVLTV PGSERSYDLT    60
GLKPGTEYSV LIHGVKGGLL SSPLSAIFTT                                      90

SEQ ID NO: 284          moltype = AA  length = 90
FEATURE                 Location/Qualifiers
source                  1..90
                        mol_type = protein
                        organism = synthetic construct
SEQUENCE: 284
MLPAPKNLVV SRVTEDSARL SWTAPDAAFD SFFIGYLEPQ PPGEAIVLTV PGSERSYDLT    60
GLKPGTEYNV TIQGVKGGFP SMPLSAIFTT                                      90

SEQ ID NO: 285          moltype = AA  length = 90
FEATURE                 Location/Qualifiers
source                  1..90
                        mol_type = protein
                        organism = synthetic construct
SEQUENCE: 285
MLPAPKNLVV SRVTEDSARL SWTAPDAAFD SFLIPYAETS PSGEAIVLTV PGSERSYDLT    60
GLKPGTEYSV LIHGVKGGDY SSPLSAIFTT                                      90

SEQ ID NO: 286          moltype = AA  length = 90
FEATURE                 Location/Qualifiers
source                  1..90
                        mol_type = protein
                        organism = synthetic construct
SEQUENCE: 286
MLPAPKNLVV SRVTEDSARL SWTAPDAAFD SFNIYYPEFP VRGEAIVLTV PGSERSYDLT    60
GLKPGTEYVV SIWGVKGGTQ SWPLSAIFTT                                      90

SEQ ID NO: 287          moltype = AA  length = 90
FEATURE                 Location/Qualifiers
source                  1..90
                        mol_type = protein
                        organism = synthetic construct
SEQUENCE: 287
```

-continued

```
MLPAPKNLVV SRVTEDSARL SWTAPDAAFD SFTIEYHESG PVGEAIVLTV PGSERSYDLT    60
GLKPGTEYMV WIFGVKGGFV SRPLSAIFTT                                       90

SEQ ID NO: 288            moltype = AA  length = 90
FEATURE                   Location/Qualifiers
source                    1..90
                          mol_type = protein
                          organism = synthetic construct
SEQUENCE: 288
MLPAPKNLVV SRVTEDSARL SWTAPDAAFD SFLIPYAETS PSGEAIVLTV PGSERSYDLT    60
GLKPGTEYSV LIHGVKGGDY SSPLSAISTT                                       90

SEQ ID NO: 289            moltype = AA  length = 90
FEATURE                   Location/Qualifiers
source                    1..90
                          mol_type = protein
                          organism = synthetic construct
SEQUENCE: 289
MLPAPKNLVV SRVTEDSARL SWTAPDAAFD SFAIPYYEDT NDGEAIVLTV PGSERSYDLT    60
GLKPGTEYWV SIQGVKGGTV SGPLSAIFTT                                       90

SEQ ID NO: 290            moltype = AA  length = 88
FEATURE                   Location/Qualifiers
source                    1..88
                          mol_type = protein
                          organism = synthetic construct
SEQUENCE: 290
MLPAPKNLVV SRVTEDSARL SWTAPDAAFD SFFYLEQAWG GEAIVLTVPG SERSYDLTGL    60
KPGTEYWVEI TGVKGGYASS PLSAIFTT                                         88

SEQ ID NO: 291            moltype = AA  length = 90
FEATURE                   Location/Qualifiers
source                    1..90
                          mol_type = protein
                          organism = synthetic construct
SEQUENCE: 291
MLPAPKNLVV SRVTEDSARL SWTAPDAAFD SFHIEYEEPE TEGEAIYLHV PGSERSYDLT    60
GLKPGTEYKV LIRGVKGGSY SIPLQAPFTT                                       90

SEQ ID NO: 292            moltype = AA  length = 90
FEATURE                   Location/Qualifiers
source                    1..90
                          mol_type = protein
                          organism = synthetic construct
SEQUENCE: 292
MLPAPKNLVV SRVTEDSARL SWTAPDAAFD SFDIAYWELT PSGEAIELLV PGSERSYDLT    60
GLKPGTEYRV DIIGVKGGFI SEPLGATFTT                                       90

SEQ ID NO: 293            moltype = AA  length = 90
FEATURE                   Location/Qualifiers
source                    1..90
                          mol_type = protein
                          organism = synthetic construct
SEQUENCE: 293
MLPAPKNLVV SRVTEDSARL SWTAPDAAFD SFTIEYWEFT GSGEAIVLTV PGSERSYDLT    60
GLKPGTEYDV SIYGVKGGWL SYPLSAIFTT                                       90

SEQ ID NO: 294            moltype = AA  length = 90
FEATURE                   Location/Qualifiers
source                    1..90
                          mol_type = protein
                          organism = synthetic construct
SEQUENCE: 294
MLPAPKNLVV SRVTEDSARL SWTAPDAAFD SFSIIYSEWN VTGEAIVLTV PGSERSYDLT    60
GLKPGTEYDV WIEGVKGGGM SKPLSAISTT                                       90

SEQ ID NO: 295            moltype = AA  length = 90
FEATURE                   Location/Qualifiers
source                    1..90
                          mol_type = protein
                          organism = synthetic construct
SEQUENCE: 295
MLPAPKNLVV SRVTEDSARL SWTAPDAAFD SFFIGYLEPI PSGEAIVLTV PGSERSYDLT    60
GLKPGTEYPV VIQGVKGGHP SQPLSAIFTT                                       90

SEQ ID NO: 296            moltype = AA  length = 90
FEATURE                   Location/Qualifiers
source                    1..90
                          mol_type = protein
```

-continued

```
                           organism = synthetic construct
SEQUENCE: 296
MLPAPKNLVV SRVTEDSARL SWTAPDAAFD SFFIGYLEPQ PPGEAIILTV PGSERSYDLT   60
GLKPGTEYNV TIQGVKGGFP SMPLSAIFTT                                     90

SEQ ID NO: 297          moltype = AA  length = 90
FEATURE                 Location/Qualifiers
source                  1..90
                        mol_type = protein
                        organism = synthetic construct
SEQUENCE: 297
MLPAPKNLVV SRVTEDSARL SWTAPDAAFD SFLIPYAETS PSGEAITLFV PGSERSYDLT   60
GLKPGTEYNV VIQGVKGGRP SNPLVAASTT                                     90

SEQ ID NO: 298          moltype = AA  length = 90
FEATURE                 Location/Qualifiers
source                  1..90
                        mol_type = protein
                        organism = synthetic construct
SEQUENCE: 298
MLPAPKNLVV SRVTEDSARL SWTAPDAAFD SFPIAYAEPR PDGEAIVLTV PGSERSYDLT   60
GLKPGTEYSV LIHGVKGGLL SSPLSAISTT                                     90

SEQ ID NO: 299          moltype = AA  length = 90
FEATURE                 Location/Qualifiers
source                  1..90
                        mol_type = protein
                        organism = synthetic construct
SEQUENCE: 299
MLPAPKNLVV SRVTEDSARL SWTAPDAAFD SFLIEYWESV GYGEAIVLTV PGSERSYDLT   60
GLKPGTEYWV GIYGVKGGYY SRPLSAIFTT                                     90

SEQ ID NO: 300          moltype = AA  length = 90
FEATURE                 Location/Qualifiers
source                  1..90
                        mol_type = protein
                        organism = synthetic construct
SEQUENCE: 300
MLPAPKNLVV SRVTEDSARL SWTAPDAAFD SFFIGYLEPQ PPGEAIVLTV PGSERSYDLT   60
GLKPGTEYNV TIHGVKGGTP SMPLSAIFTT                                     90

SEQ ID NO: 301          moltype = AA  length = 90
FEATURE                 Location/Qualifiers
source                  1..90
                        mol_type = protein
                        organism = synthetic construct
SEQUENCE: 301
MLPAPKNLVV SRVTEDSARL SWTAPDAAFD SFEIEYDEPY RGGEAIVLTV PGSERSYDLT   60
SLKPGTEYPV SIGGVKGGIT SDPLSAIFTT                                     90

SEQ ID NO: 302          moltype = AA  length = 90
FEATURE                 Location/Qualifiers
source                  1..90
                        mol_type = protein
                        organism = synthetic construct
SEQUENCE: 302
MLPAPKNLVV SRVTEDSARL SWTAPDAAFD SFDIYYPEYY DRGEAIVLTV PGSERSYDLT   60
GLKPGTEYTV YIDGVKGGGG SGPLSAIFTT                                     90

SEQ ID NO: 303          moltype = AA  length = 90
FEATURE                 Location/Qualifiers
source                  1..90
                        mol_type = protein
                        organism = synthetic construct
SEQUENCE: 303
MLPAPKNLVV SRVTEDSARL SWTAPDAAFD SFFIAYFEFA NPGEAIVLTV PGSERSYDLT   60
GLKPGTEYKV VIQGVKGGTP SEPLSAIFTT                                     90

SEQ ID NO: 304          moltype = AA  length = 90
FEATURE                 Location/Qualifiers
source                  1..90
                        mol_type = protein
                        organism = synthetic construct
SEQUENCE: 304
MLPAPKNLVV SRVTEDSARL SWTAPDAAFD SFIITYWEHV GDGEAIVLTV PGSERSYDLT   60
GLKPGTEYFV EIYGVKGGYL SKPLSAIFTT                                     90

SEQ ID NO: 305          moltype = AA  length = 90
FEATURE                 Location/Qualifiers
```

-continued

```
source               1..90
                     mol_type = protein
                     organism = synthetic construct
SEQUENCE: 305
MLPAPKNLVV SRVTEDSARL SWTAPDAAFD SFEIDYDEPF VYGEAIVLTV PGSERSYDLT    60
GLKPGTEYRV FIFGVKGGNG SWPLSAIFTT                                     90

SEQ ID NO: 306       moltype = AA  length = 90
FEATURE              Location/Qualifiers
source               1..90
                     mol_type = protein
                     organism = synthetic construct
SEQUENCE: 306
MLPAPKNLVV SRVTEDSARL SWTAPDAAFD SFYIEYFETQ GYGEAIVLTV PGSERSYDLT    60
GLKPGTEYYV AIYGVKGGYL SRPLSAIFTT                                     90

SEQ ID NO: 307       moltype = AA  length = 90
FEATURE              Location/Qualifiers
source               1..90
                     mol_type = protein
                     organism = synthetic construct
SEQUENCE: 307
MLPAPKNLVV SRVTEDSARL SWTAPDAAFD SFPITYSEPA HYGEAIVLTV PGSERSYDLT    60
GLKPGTEYHV GIMGVKGGVF SSPLSAIFTT                                     90

SEQ ID NO: 308       moltype = AA  length = 90
FEATURE              Location/Qualifiers
source               1..90
                     mol_type = protein
                     organism = synthetic construct
SEQUENCE: 308
MLPAPKNLVV SEVTEDSARL SWQGVARAFD SFLITYREQI FAGEVIVLTV PGSERSYDLT    60
GLKPGTEYPV WIQGVKGGSP SAPLSAISTT                                     90

SEQ ID NO: 309       moltype = AA  length = 90
FEATURE              Location/Qualifiers
source               1..90
                     mol_type = protein
                     organism = synthetic construct
SEQUENCE: 309
MLPAPKNLVV SRVTEDSARL SWTAPDAAFD SFIIDYLELD QEGEAIVLTV PGSERSYDLT    60
GLKPGTEYAV YIFGVKGGYP STPLSAIFTT                                     90

SEQ ID NO: 310       moltype = AA  length = 5
FEATURE              Location/Qualifiers
source               1..5
                     mol_type = protein
                     organism = synthetic construct
SEQUENCE: 310
GGGGS                                                                5
```

What is claimed:

1. A method of delivering a polynucleotide to a muscle cell, wherein the method comprises contacting the muscle cell with the polynucleotide conjugated to a polypeptide that binds to cluster of differentiation 71 (CD71) and comprises the amino acid sequence that is at least 95% identical to the amino acid sequence of SEQ ID NO: 146.

2. The method of claim 1, wherein the polynucleotide is a double-stranded short interfering ribonucleic acid (siRNA) molecule.

3. The method of claim 1, wherein the polynucleotide is an antisense molecule.

4. The method of claim 1, wherein the N-terminus of the polypeptide is a methionine.

5. The method of claim 1, wherein the amino acid at position 54 of SEQ ID NO: 146 of the polypeptide is substituted with a cysteine.

6. The method of claim 1, wherein the polypeptide further comprises a half-life extending moiety.

7. The method of claim 6, wherein the half-life extending moiety is an albumin-binding molecule.

8. The method of claim 7, wherein the albumin-binding molecule is a polypeptide that binds albumin or an albumin variant.

9. The method of claim 6, wherein the half-life extending moiety is a polyethylene glycol, albumin, an albumin variant, or a portion of an Fc region of an immunoglobulin.

10. The method of claim 1, wherein the polypeptide comprises the amino acid sequence of SEQ ID NO:.

11. The method of claim 1, wherein the polypeptide binds CD71 and is linked to another polypeptide that binds CD71 or another target protein.

12. The method of claim 1, wherein the polypeptide comprises the amino acid sequence of SEQ ID NO: 146.

13. The method of claim 1, wherein the polypeptide comprises the amino acid sequence of SEQ ID NO: 283.

14. The method of claim 1, wherein the polypeptide comprises the amino acid sequence of SEQ ID NO: 181.

15. The method of claim 1, wherein the polypeptide comprises the amino acid sequence of SEQ ID NO: 298.

16. The method of claim 1, wherein the polypeptide comprises the amino acid sequence of SEQ ID NO: 278.

17. The method of claim 1, wherein the polypeptide comprises the amino acid sequence of SEQ ID NO: 176.

18. The method of claim 1, wherein the polypeptide comprises the amino acid sequence of SEQ ID NO: 271.

* * * * *